(12) United States Patent
Mahurkar

(10) Patent No.: US 7,918,821 B2
(45) Date of Patent: Apr. 5, 2011

(54) UNIVERSAL SAFETY SYRINGE

(76) Inventor: Sakharam D. Mahurkar, Aurora, IL (US)

( * ) Notice: Subject to any disclaimer, the term of this patent is extended or adjusted under 35 U.S.C. 154(b) by 30 days.

(21) Appl. No.: 12/435,652

(22) Filed: May 5, 2009

(65) Prior Publication Data

US 2010/0286609 A1   Nov. 11, 2010

(51) Int. Cl.
*A61M 5/00* (2006.01)
(52) U.S. Cl. .......................... 604/110; 604/11; 604/218
(58) Field of Classification Search .................. 604/110, 604/111, 218, 11
See application file for complete search history.

(56) References Cited

U.S. PATENT DOCUMENTS

| | | | |
|---|---|---|---|
| 2,888,923 A | 6/1959 | Da Cunha Reis | 128/218 |
| 2,925,083 A | 2/1960 | Craig | 128/218 |
| 3,610,240 A | 10/1971 | Harautuneian | 128/214 |
| 3,658,061 A | 4/1972 | Hall | 128/214 |
| 4,068,659 A | 1/1978 | Moorehead | 128/214 |
| 4,134,402 A | 1/1979 | Mahurkar | 128/214 |
| 4,233,982 A | 11/1980 | Bauer et al. | 128/347 |
| 4,245,635 A | 1/1981 | Kontos | 128/214 |
| 4,261,357 A | 4/1981 | Kontos | 128/214 |
| 4,274,408 A | 6/1981 | Nimrod | 128/214 |
| 4,274,836 A | 6/1981 | Ban et al. | 44/6 |
| 4,417,886 A | 11/1983 | Frankhouser et al. | 604/53 |
| 4,424,833 A | 1/1984 | Spector et al. | 137/849 |
| 4,425,120 A | 1/1984 | Sampson et al. | 604/198 |
| D272,651 S | 2/1984 | Mahurkar | D24/54 |
| 4,443,333 A | 4/1984 | Mahurkar | 210/87 |
| 4,468,224 A | 8/1984 | Enzmann et al. | 604/247 |
| 4,529,399 A | 7/1985 | Groshong et al. | 604/53 |
| 4,568,329 A | 2/1986 | Mahurkar | 604/43 |
| 4,583,968 A | 4/1986 | Mahurkar | 604/43 |
| 4,623,327 A | 11/1986 | Mahurkar | 604/4 |
| 4,631,057 A | 12/1986 | Mitchell | 604/198 |
| 4,659,330 A | 4/1987 | Nelson et al. | 604/192 |

(Continued)

FOREIGN PATENT DOCUMENTS

AU       752319       1/2003

(Continued)

OTHER PUBLICATIONS

"Prefilled Syringes—Part 4: Glass Barrels for Injectables," International Standard, ISO 110404, Second Edition, 14 pages (Feb. 1, 2007).

(Continued)

*Primary Examiner* — Nicholas D Lucchesi
*Assistant Examiner* — Leah Stohr
(74) *Attorney, Agent, or Firm* — Nixon Peabody LLP

(57) ABSTRACT

A syringe comprises a generally-cylindrical, hollow barrel with a hollow nozzle at a distal end thereof. A plunger with an open channel is slidably mounted in the barrel. A needle holder with a needle mounted at one end thereof is arranged in the plunger channel, and movable between an advanced position, whereat the needle projects from a distal end of the nozzle for injection, and a retracted position, whereat the needle is enclosed within the barrel when the injection is complete. A spring retainer is arranged in the barrel. A spring is positioned within the spring retainer, urging the needle holder toward the retracted position. A latch latches the needle holder to the spring retainer thereby maintaining the spring in compression. The latch is releasable in response to the plunger moving to its fully advanced position, whereby the needle holder is released, allowing the spring to expand and thereby move the needle holder to the retracted position.

34 Claims, 34 Drawing Sheets

U.S. PATENT DOCUMENTS

| | | | |
|---|---|---|---|
| 4,664,654 A | 5/1987 | Strauss | 604/198 |
| 4,666,435 A | 5/1987 | Braginetz | 604/198 |
| 4,692,141 A | 9/1987 | Mahurkar | 604/43 |
| 4,693,708 A | 9/1987 | Wanderer et al. | 604/198 |
| 4,699,199 A | 10/1987 | Hunter | |
| 4,702,738 A | 10/1987 | Spencer | 604/198 |
| 4,710,170 A | 12/1987 | Haber et al. | 604/110 |
| 4,731,059 A | 3/1988 | Wanderer et al. | 604/192 |
| 4,731,068 A | 3/1988 | Hesse | 604/110 |
| 4,732,162 A | 3/1988 | Martell | 128/765 |
| 4,735,617 A | 4/1988 | Nelson et al. | 604/192 |
| 4,735,618 A | 4/1988 | Hagen | 604/192 |
| 4,742,910 A | 5/1988 | Staebler | 206/365 |
| 4,746,017 A | 5/1988 | Howard et al. | 206/438 |
| 4,747,831 A | 5/1988 | Kulli | 604/110 |
| 4,747,835 A | 5/1988 | Sandhaus | 604/192 |
| 4,747,836 A | 5/1988 | Luther | 604/198 |
| 4,752,290 A | 6/1988 | Schramm | 604/198 |
| 4,762,516 A | 8/1988 | Luther et al. | 604/164 |
| 4,767,412 A | 8/1988 | Hymanson | 604/192 |
| 4,767,413 A | 8/1988 | Haber et al. | 604/110 |
| 4,770,652 A | 9/1988 | Mahurkar | 604/4 |
| 4,778,453 A | 10/1988 | Lopez | 604/110 |
| D298,352 S | 11/1988 | Raines | D24/25 |
| 4,782,841 A | 11/1988 | Lopez | 128/164 |
| 4,790,822 A | 12/1988 | Haining | 604/110 |
| 4,799,926 A | 1/1989 | Haber | 604/187 |
| 4,801,295 A | 1/1989 | Spencer | 604/198 |
| 4,808,155 A | 2/1989 | Mahurkar | 604/43 |
| 4,808,169 A | 2/1989 | Haber et al. | 604/43 |
| 4,813,426 A | 3/1989 | Haber et al. | 128/763 |
| 4,813,938 A | 3/1989 | Raulerson | 604/167 |
| 4,816,811 A | 3/1989 | Bogatin et al. | 340/712 |
| 4,819,659 A | 4/1989 | Sitar | 128/764 |
| 4,826,488 A | 5/1989 | Nelson et al. | 604/192 |
| 4,826,489 A | 5/1989 | Haber et al. | 604/195 |
| 4,826,491 A | 5/1989 | Schramm | 604/198 |
| 4,828,107 A | 5/1989 | Spencer | 209/366 |
| 4,828,548 A | 5/1989 | Walter | 604/164 |
| 4,832,696 A | 5/1989 | Luther et al. | 604/164 |
| 4,834,717 A | 5/1989 | Haber et al. | 604/193 |
| 4,838,863 A | 6/1989 | Allard et al. | 604/110 |
| 4,838,871 A | 6/1989 | Luther | 604/192 |
| 4,842,582 A | 6/1989 | Mahurkar | 604/43 |
| 4,842,591 A | 6/1989 | Luther | 604/283 |
| 4,850,961 A | 7/1989 | Wanderer et al. | 604/53 |
| 4,850,976 A | 7/1989 | Heinrich et al. | 604/192 |
| 4,852,584 A | 8/1989 | Selby | 128/760 |
| 4,860,742 A | 8/1989 | Park et al. | 128/303 |
| 4,863,435 A | 9/1989 | Sturman et al. | 604/198 |
| 4,863,436 A | 9/1989 | Glick | 604/198 |
| 4,872,552 A | 10/1989 | Unger | 206/365 |
| 4,874,382 A | 10/1989 | Lindemann et al. | 604/195 |
| 4,874,384 A | 10/1989 | Nunez | 604/198 |
| 4,883,469 A | 11/1989 | Glazier | 604/192 |
| 4,887,998 A | 12/1989 | Martin et al. | 604/110 |
| 4,892,525 A | 1/1990 | Hermann, Jr. et al. | 604/263 |
| 4,894,055 A | 1/1990 | Sudnak | 604/198 |
| 4,895,561 A | 1/1990 | Mahurkar | 604/43 |
| 4,897,083 A | 1/1990 | Martell | 604/192 |
| 4,898,588 A | 2/1990 | Roberts | 604/187 |
| 4,900,307 A | 2/1990 | Kulli | 604/110 |
| 4,900,311 A | 2/1990 | Stern et al. | 604/198 |
| 4,903,832 A | 2/1990 | Stewart | 206/366 |
| 4,906,235 A | 3/1990 | Roberts | 604/192 |
| 4,909,794 A | 3/1990 | Haber et al. | 604/195 |
| 4,911,693 A | 3/1990 | Paris | 604/192 |
| 4,915,697 A | 4/1990 | DuPont | 604/192 |
| 4,927,019 A | 5/1990 | Haber et al. | 206/365 |
| 4,927,414 A | 5/1990 | Kulli | 604/110 |
| 4,927,417 A | 5/1990 | Moncada et al. | 604/198 |
| 4,928,824 A | 5/1990 | Barasch | 206/365 |
| 4,929,237 A | 5/1990 | Medway | 604/198 |
| 4,929,241 A | 5/1990 | Kulli | 604/263 |
| 4,931,040 A | 6/1990 | Haber et al. | 604/110 |
| 4,931,048 A | 6/1990 | Lopez | 604/110 |
| 4,932,940 A | 6/1990 | Walker et al. | 604/110 |
| 4,932,946 A | 6/1990 | Shields | 604/198 |
| 4,935,015 A | 6/1990 | Hall | 604/195 |
| 4,944,723 A | 7/1990 | Haber et al. | 604/110 |
| 4,944,728 A | 7/1990 | Carrell et al. | 604/164 |
| 4,944,731 A | 7/1990 | Cole | 604/192 |
| 4,946,447 A | 8/1990 | Hardcastle et al. | 604/198 |
| 4,950,241 A | 8/1990 | Ranford | 604/110 |
| 4,950,252 A | 8/1990 | Luther et al. | 604/198 |
| 4,958,622 A | 9/1990 | Selenke | 128/765 |
| 4,964,854 A | 10/1990 | Luther | 604/166 |
| 4,973,316 A | 11/1990 | Dysarz | 604/195 |
| 4,976,702 A | 12/1990 | Andrews et al. | 604/198 |
| 4,978,343 A | 12/1990 | Deysarz et al. | 604/195 |
| 4,986,813 A | 1/1991 | Blake, III et al. | 604/110 |
| 4,986,819 A | 1/1991 | Sobel | 604/198 |
| 4,988,339 A | 1/1991 | Vadher | 604/197 |
| 4,994,034 A * | 2/1991 | Botich et al. | 604/110 |
| 4,994,042 A | 2/1991 | Vadher | 604/165 |
| 4,994,044 A | 2/1991 | Lo Duca | 604/192 |
| 4,997,422 A | 3/1991 | Chow et al. | 604/198 |
| 5,000,167 A | 3/1991 | Sunderland | 128/763 |
| 5,002,536 A | 3/1991 | Thompson et al. | 604/192 |
| 5,013,304 A | 5/1991 | Russell et al. | 604/167 |
| 5,015,241 A | 5/1991 | Feimer | 604/198 |
| 5,019,044 A | 5/1991 | Tsao | 604/110 |
| 5,019,045 A | 5/1991 | Lee | 604/110 |
| 5,019,051 A | 5/1991 | Hake | 604/198 |
| 5,024,326 A | 6/1991 | Sandel et al. | 206/366 |
| 5,024,660 A | 6/1991 | McNaughton | 604/110 |
| 5,026,345 A | 6/1991 | Teringo | 604/110 |
| 5,026,354 A | 6/1991 | Kocses | 604/195 |
| 5,030,209 A | 7/1991 | Wanderer et al. | 604/198 |
| 5,030,212 A | 7/1991 | Rose | 604/263 |
| 5,037,400 A | 8/1991 | Curry | 604/192 |
| 5,037,401 A | 8/1991 | DeCamp | 604/192 |
| 5,045,062 A | 9/1991 | Henson | 604/110 |
| 5,046,508 A | 9/1991 | Weissler | 128/763 |
| 5,049,136 A | 9/1991 | Johnson | 604/198 |
| 5,051,109 A | 9/1991 | Simon | 604/263 |
| 5,053,017 A | 10/1991 | Chamuel | 604/192 |
| 5,057,088 A | 10/1991 | Narayanan | 604/198 |
| 5,057,089 A | 10/1991 | Greco | 604/198 |
| 5,059,180 A | 10/1991 | McLees | 604/110 |
| 5,061,249 A | 10/1991 | Campbell | 604/195 |
| 5,066,279 A | 11/1991 | Russell | 604/110 |
| 5,066,281 A | 11/1991 | Stevenson-Michener | 604/110 |
| 5,067,942 A | 11/1991 | Jaffe et al. | 604/110 |
| 5,067,944 A | 11/1991 | Nichols | 604/192 |
| 5,067,946 A | 11/1991 | Zhadanov | 604/198 |
| 5,067,949 A | 11/1991 | Freundlich et al. | 604/263 |
| 5,069,669 A | 12/1991 | Kole | 604/198 |
| 5,078,693 A | 1/1992 | Shine | 604/192 |
| 5,084,019 A | 1/1992 | Gartz | 604/110 |
| 5,084,029 A | 1/1992 | Nacci nee Tagliaferri et al. | 604/195 |
| 5,086,780 A | 2/1992 | Schmitt | 128/763 |
| 5,088,987 A | 2/1992 | Noonan, Jr. | 604/195 |
| 5,088,988 A | 2/1992 | Talonn et al. | 604/198 |
| 5,092,853 A | 3/1992 | Couvertier, II | 604/195 |
| 5,098,394 A | 3/1992 | Luther | 604/167 |
| 5,098,402 A | 3/1992 | Davis | 604/195 |
| 5,098,405 A | 3/1992 | Peterson et al. | 604/247 |
| 5,106,379 A | 4/1992 | Leap | 604/198 |
| 5,106,380 A | 4/1992 | Lobello | 604/198 |
| 5,108,378 A | 4/1992 | Firth | 604/192 |
| 5,112,307 A | 5/1992 | Haber et al. | 604/110 |
| 5,112,315 A | 5/1992 | Gloyer et al. | 604/195 |
| 5,112,316 A | 5/1992 | Venturini | 604/195 |
| 5,114,404 A | 5/1992 | Paxton et al. | 604/110 |
| 5,116,319 A | 5/1992 | van den Haak | 604/110 |
| 5,116,325 A | 5/1992 | Paterson | 604/192 |
| 5,120,309 A | 6/1992 | Watts | 604/110 |
| 5,122,118 A | 6/1992 | Haber et al. | 604/110 |
| 5,125,898 A | 6/1992 | Kaufhold, Jr. et al. | 604/110 |
| 5,127,910 A | 7/1992 | Talonn et al. | 604/198 |
| 5,135,504 A | 8/1992 | McLees | 604/164 |
| 5,135,505 A | 8/1992 | Kaufman | 604/165 |
| 5,135,510 A | 8/1992 | Maszkiewicz et al. | 604/195 |
| 5,147,303 A | 9/1992 | Martin | 604/110 |
| 5,147,326 A | 9/1992 | Talonn et al. | 604/198 |

| | | | |
|---|---|---|---|
| 5,160,326 A | 11/1992 | Taolonn et al. | 604/198 |
| 5,163,908 A | 11/1992 | Lambert | 604/110 |
| 5,163,917 A | 11/1992 | Huefner et al. | 604/198 |
| 5,171,300 A | 12/1992 | Blake, III et al. | 604/110 |
| 5,171,303 A | 12/1992 | DeCamp | 604/192 |
| 5,176,640 A | 1/1993 | Nacci et al. | 604/110 |
| 5,176,655 A | 1/1993 | McCormick et al. | 604/198 |
| 5,181,524 A | 1/1993 | Wanderer et al. | 128/764 |
| 5,183,468 A | 2/1993 | McLees | 604/164 |
| 5,188,119 A | 2/1993 | Sunderland | 128/763 |
| 5,188,611 A | 2/1993 | Orgain | 604/192 |
| 5,188,613 A | 2/1993 | Shaw | 604/195 |
| 5,190,526 A | 3/1993 | Murray et al. | 604/110 |
| 5,190,532 A | 3/1993 | Yu | 604/192 |
| 5,195,973 A | 3/1993 | Novick | 604/110 |
| 5,195,975 A | 3/1993 | Castagna | 604/110 |
| 5,195,982 A | 3/1993 | Hoenig | 604/192 |
| 5,195,983 A | 3/1993 | Boese | 604/192 |
| 5,195,992 A | 3/1993 | Dudar et al. | 604/283 |
| 5,195,993 A | 3/1993 | Gianakos | 604/283 |
| 5,197,951 A | 3/1993 | Mahurkar | 604/283 |
| 5,197,953 A | 3/1993 | Colonna | 604/110 |
| 5,197,954 A | 3/1993 | Cameron | 604/110 |
| 5,201,718 A | 4/1993 | Whisson | 604/194 |
| 5,215,524 A | 6/1993 | Vallelunga et al. | 604/110 |
| 5,215,525 A | 6/1993 | Sturman | 604/164 |
| 5,215,528 A | 6/1993 | Purdy et al. | 604/164 |
| 5,215,529 A | 6/1993 | Fields et al. | 604/168 |
| 5,215,533 A | 6/1993 | Robb | 604/195 |
| 5,215,534 A | 6/1993 | De Harde et al. | 604/198 |
| 5,215,535 A | 6/1993 | Gettig et al. | 604/198 |
| 5,217,436 A | 6/1993 | Farkas | 604/187 |
| 5,217,437 A | 6/1993 | Talonn et al. | 604/198 |
| 5,218,965 A | 6/1993 | Ring | 128/673 |
| 5,219,333 A | 6/1993 | Sagstetter et al. | 604/110 |
| 5,219,338 A | 6/1993 | Haworth | 664/198 |
| 5,221,255 A | 6/1993 | Mahurkar et al. | 604/43 |
| 5,221,256 A | 6/1993 | Mahurkar | 604/43 |
| 5,221,262 A | 6/1993 | Kite | 604/110 |
| 5,222,942 A | 6/1993 | Bader | 604/110 |
| 5,222,943 A | 6/1993 | Mazzara | 604/110 |
| 5,222,944 A | 6/1993 | Harris | 604/110 |
| 5,222,945 A | 6/1993 | Basnight | 604/110 |
| 5,222,947 A | 6/1993 | D'Amico | 604/198 |
| 5,267,961 A | 12/1993 | Shaw | |
| 5,273,541 A | 12/1993 | Malenchek | 604/110 |
| 5,324,265 A | 6/1994 | Murray et al. | 604/110 |
| 5,330,440 A | 7/1994 | Stanners et al. | 604/110 |
| 5,338,311 A | 8/1994 | Mahurkar | 604/195 |
| 5,342,308 A | 8/1994 | Boschetti | 604/110 |
| 5,374,245 A | 12/1994 | Mahurkar | 604/43 |
| 5,378,230 A | 1/1995 | Mahurkar | 604/43 |
| 5,380,296 A | 1/1995 | Smedley et al. | 604/193 |
| 5,385,551 A | 1/1995 | Shaw | |
| 5,395,337 A | 3/1995 | Clemens et al. | 604/110 |
| 5,486,159 A | 1/1996 | Mahurkar | 604/4 |
| 5,514,100 A | 5/1996 | Mahurkar | 604/195 |
| 5,531,694 A * | 7/1996 | Clemens et al. | 604/110 |
| 5,562,624 A | 10/1996 | Righi et al. | 604/110 |
| 5,562,626 A | 10/1996 | Sanpietro | 604/110 |
| 5,613,952 A | 3/1997 | Pressly, Sr. et al. | 604/110 |
| 5,643,222 A | 7/1997 | Mahurkar | 604/195 |
| 5,685,862 A | 11/1997 | Mahurkar | 604/194 |
| 5,695,475 A | 12/1997 | Best, Jr. et al. | 604/198 |
| 5,836,921 A | 11/1998 | Mahurkar | 604/195 |
| 5,876,382 A | 3/1999 | Erickson | |
| 5,879,338 A | 3/1999 | Mahurkar | |
| 5,885,257 A | 3/1999 | Badger | 604/195 |
| 5,891,105 A | 4/1999 | Mahurkar | 604/195 |
| 5,911,705 A | 6/1999 | Howell | |
| 6,106,500 A | 8/2000 | Mahurkar | 604/195 |
| 6,117,112 A | 9/2000 | Mahurkar | |
| 6,156,013 A | 12/2000 | Mahurkar | |
| 6,179,812 B1 | 1/2001 | Botich et al. | |
| 6,206,856 B1 | 3/2001 | Mahurkar | |
| D470,234 S | 2/2003 | Mahurkar | |
| D474,838 S | 5/2003 | Mahurkar | |
| 7,481,797 B2 | 1/2009 | Mahurkar | |

FOREIGN PATENT DOCUMENTS

| | | |
|---|---|---|
| AU | 2002300144 | 11/2007 |
| AU | 2007229397 | 2/2009 |
| CA | 2229550 | 2/1997 |
| CA | 2288461 | 5/2000 |
| CA | 2384597 | 5/2003 |
| CN | 1067385 | 12/1992 |
| CN | 1288391 | 3/2001 |
| CN | ZL02121626.6 | 10/2008 |
| DE | 2415196 | 10/1975 |
| DE | 2507119 | 9/1976 |
| DE | 3042229 | 5/1982 |
| DE | 3833138 | 4/1990 |
| DE | 60213054 | 11/2006 |
| EP | 0824932 A2 | 8/1987 |
| EP | 0360313 A1 | 3/1990 |
| EP | 0360313 B1 | 7/1993 |
| EP | 0566882 A1 | 10/1993 |
| EP | 0677298 A1 | 10/1995 |
| EP | 0754469 A2 | 6/1996 |
| EP | 0998953 | 5/2000 |
| EP | 0998953 | 10/2000 |
| EP | 1317938 | 7/2006 |
| FR | 2004771 A1 | 11/1969 |
| GB | 1317938 | 5/1973 |
| IN | 196546 | 10/2005 |
| IN | 228148 | 1/2009 |
| KR | 10-0598884 | 7/2006 |
| MY | 135223 A | 2/2008 |
| NO | 77477 | 5/2003 |
| NO | 77478 | 5/2003 |
| RO | 120952 | 10/2006 |
| WO | WO 84/01510 | 4/1984 |
| WO | WO 90/15634 | 12/1990 |
| WO | WO 91/11212 | 8/1991 |
| WO | WO 93/00950 | 1/1993 |
| WO | WO 95/30445 | 11/1995 |
| WO | WO 96/05879 | 2/1996 |
| WO | WO 97/06841 | 2/1997 |

OTHER PUBLICATIONS

"The Needlestick Safety and Prevention Act (HR5178): What Does It Require?" by Gina Pugliese, R.N., M.S. and Jane Perry, M.A., Premier Safety Institute, Premier, Inc., 4 pages (2000).

"70 percent syringes unsafe," News Capsule, The Hindu by Special Correspondent, 1 page (Dec. 17, 2004).

"Preventing Needlestick Injuries in Health Care Settings," NIOSH Alert, 28 pages (Nov., 1999).

BD Soloshot LX, BCG Auto-Disable Syringe, Reducing the Risk of Needle Reuse, 4 pages (2003).

BD Integra Syringe Brochure, MD Medical Systems, 2 pages (2002).

"Retractable Technologies, Inc. Reports Nine Months 2007 Sales of $19.1 Million," Retractable Technologies, Inc., 3 pages (Nov. 16, 2007).

"Prefilled Syringes the Trend for Growth Strengthens," ONdrugDelivery Ltd., 32 pages (2006).

"First in Safety Injection Therapy," BD Safety Product Sheet, 1 page (2001).

Brochure for Arrow® Revlerson Syringe.

Brochure for Syringes by Becton Dickinson of Franklin Lakes, New Jersey (1992).

Chiarella, Linda A, "Reducing Needlestick Injuries among Health Care Workers" AIDS Clinical Care, Oct. 1993, V. 5, No. 10, Mass Medical Safety.

The GMP Letter (5/92).

Devices & Diagnostics Letter, vol. 19., No. 19 (May 8, 1992).

Devices & Diagnostics Letter, p. 2 (Aug. 21, 1992).

FDA Medical Bulletin, vol. 22, No. 2 (Sep. 22, 1992).

"Health Care" by Helene Cooper, Wall Street Journal (Nov. 25, 1992.).

"Safer Syringes Boost Molder Opportunities" by Karl Kirkland, Plastic World, vol. 51, No. 8, pp. 20/24, (Aug. 1993).

"Ultrasonics Get Medical Seal of Approval," by Marcie Moskowitz, Plastic World, vol. 51, No. 8, pp. 26-28, (Aug. 1993).

"The International Association of Safe Injection Technology (IASIT)." PowerPoint Presentation. 14 pages. Date unknown.

Needlestick Safety and Prevention Act of 2000. Pub. L. 106-430. 114 Stat. 1901,1904. 6 Nov. 2000.

"Definition of Contaminated sharps; engineering controls and good work practice controls must be implemented; ECP must be reviewed annually." Standard Interpretations. Jun. 3, 2005. (2 pages).

"Chemical Resistance and Physical Properties." 1 page. Date unknown.

Simonsen, L. at al. "Unsafe Injections in the Developing World and Transmission of Bloodborne Pathogens: a Review."*PubMed.gov.* Bull World Health Organ. Web.

Laboratory Waste Disposal. Johns Hopkins Safety Manual. 1 page. Sep. 21, 2007.

Sharps Precautions. Cornell University Center for Animal Resources and Education. Dec. 2002. 4 pages.

Xinhua. "Unsafe Injections Kill 390,000 Prematurely." *China Daily Website—Connecting China Connecting the World*. Aug. 5, 2004. Web.

Hindustan Times. *HMD Targets Rs 200cr with New Syringe*. Kolkata, 2002. Print.

\* cited by examiner

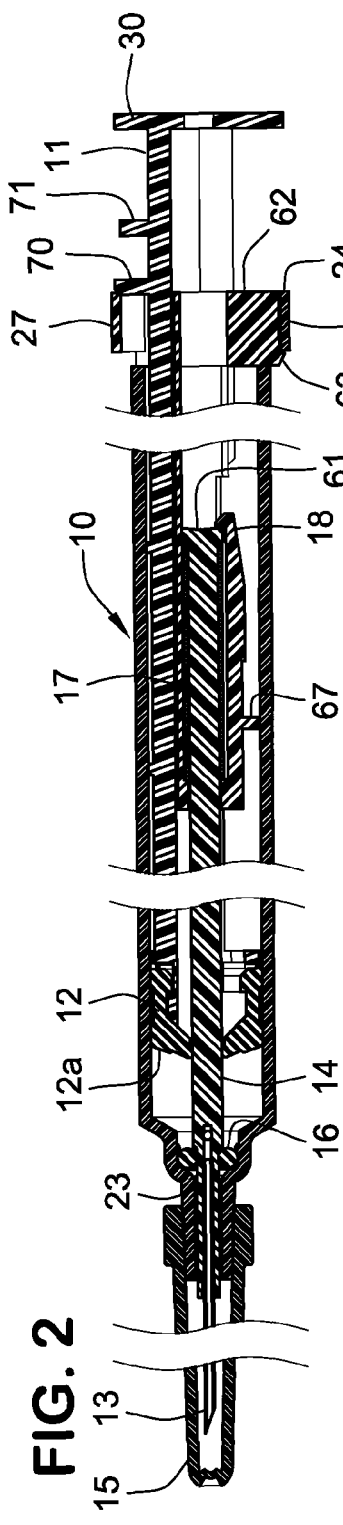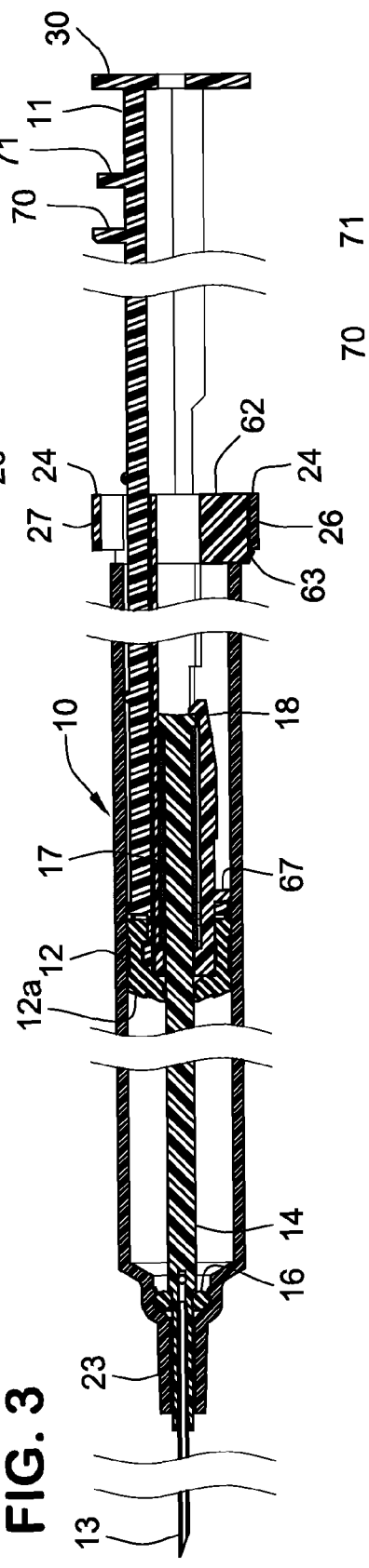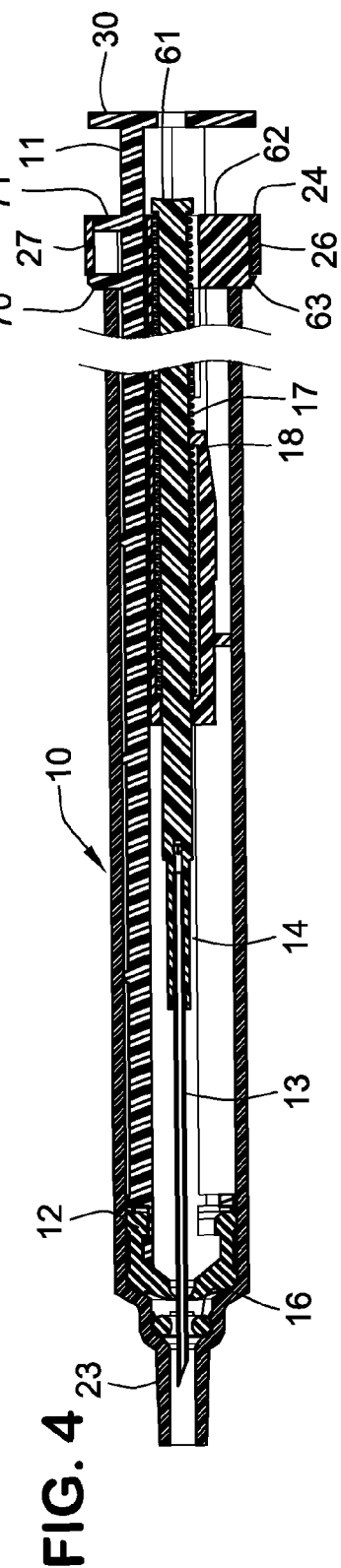

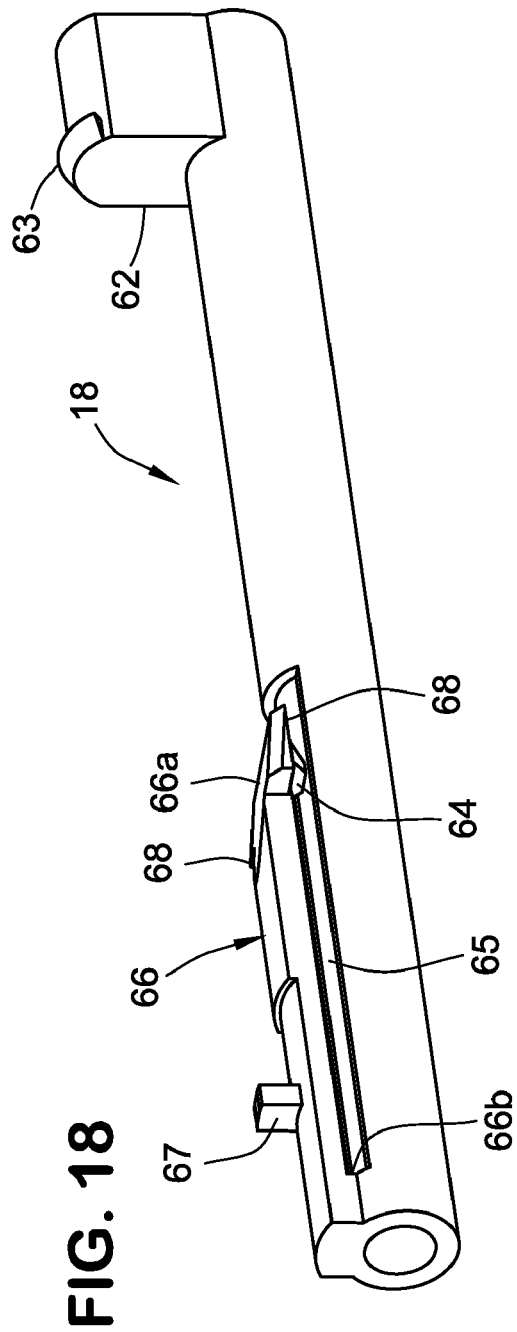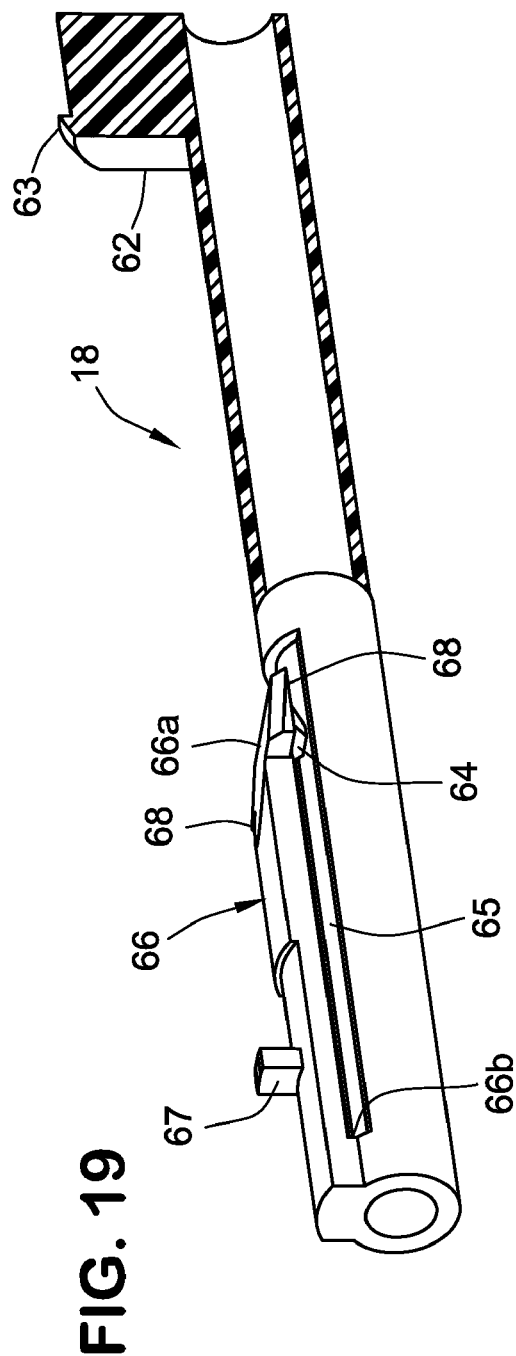

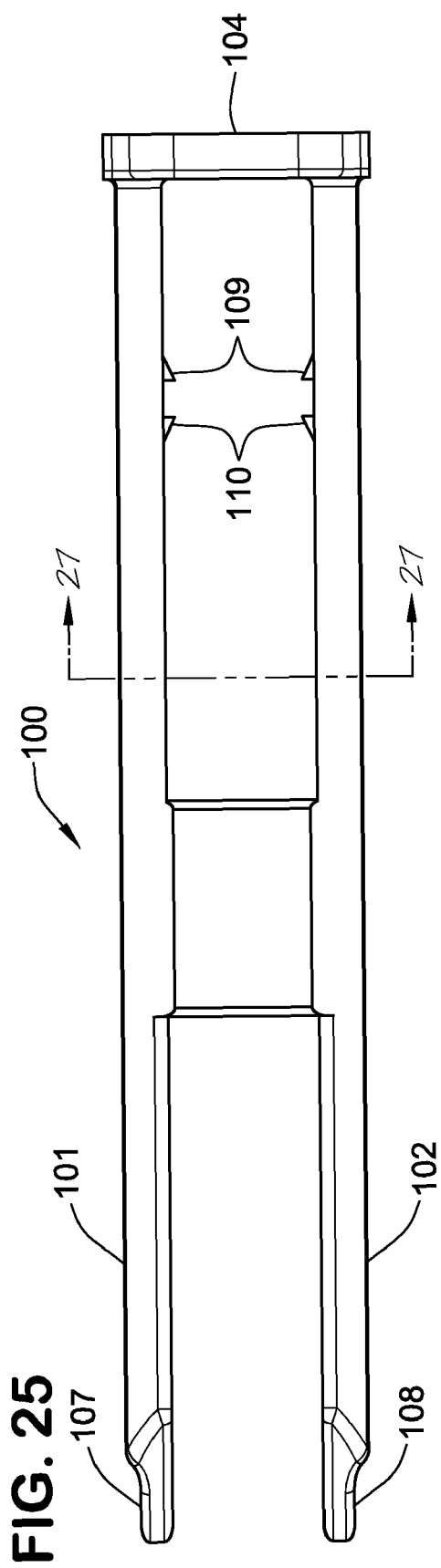
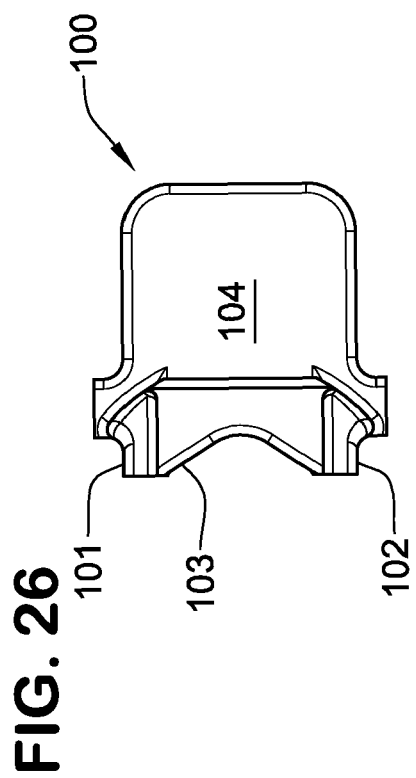

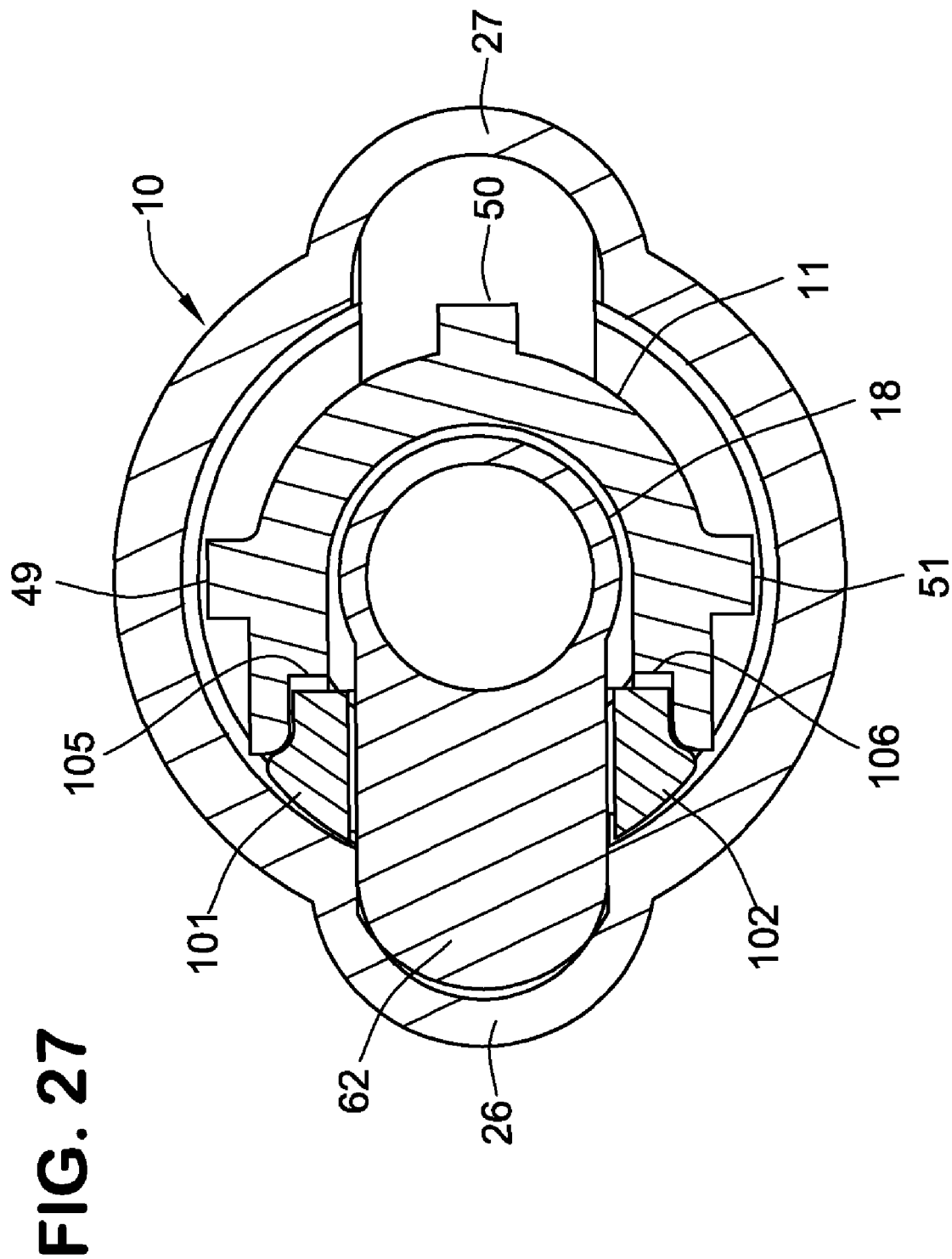

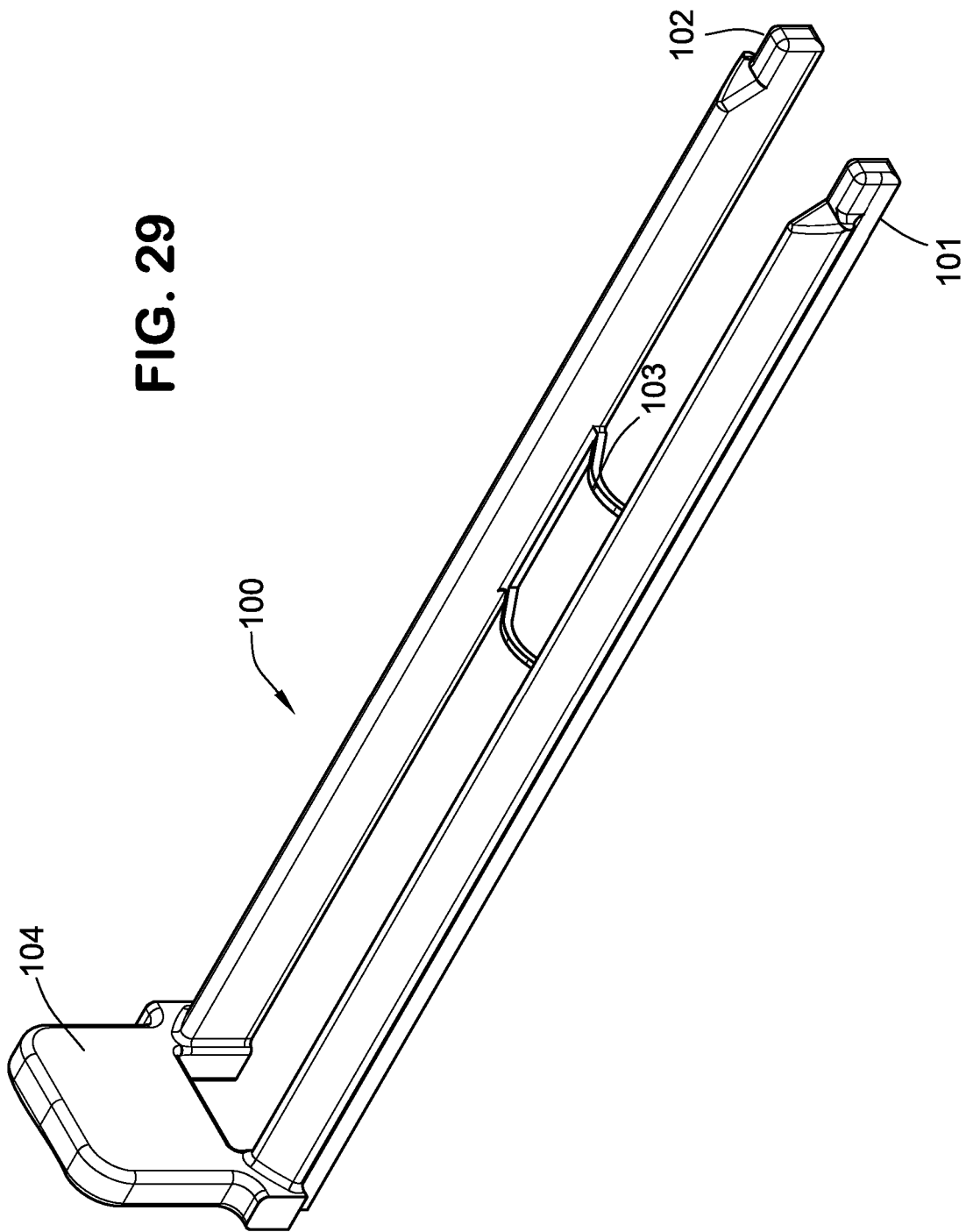

FIG. 30a FIG. 30b FIG. 30c
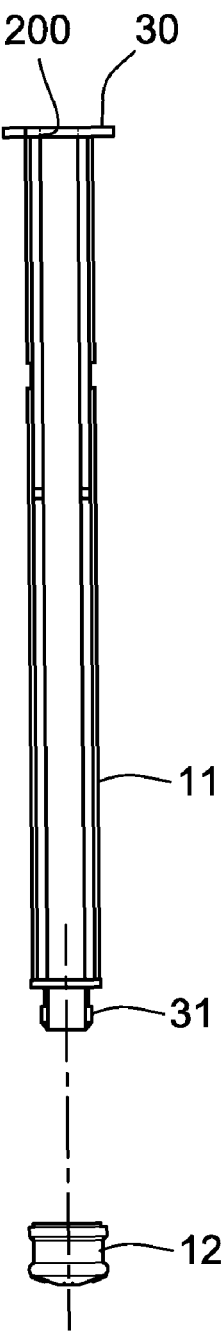
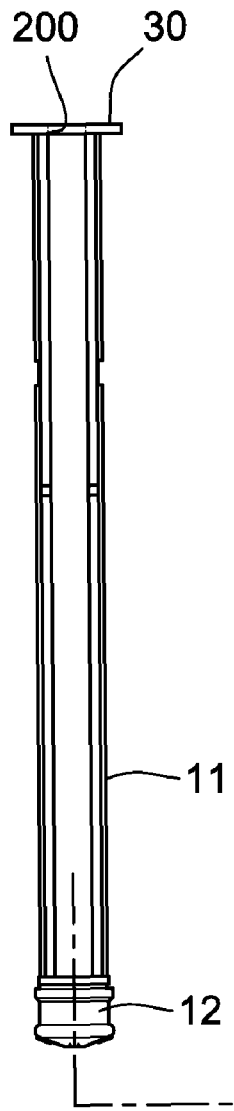
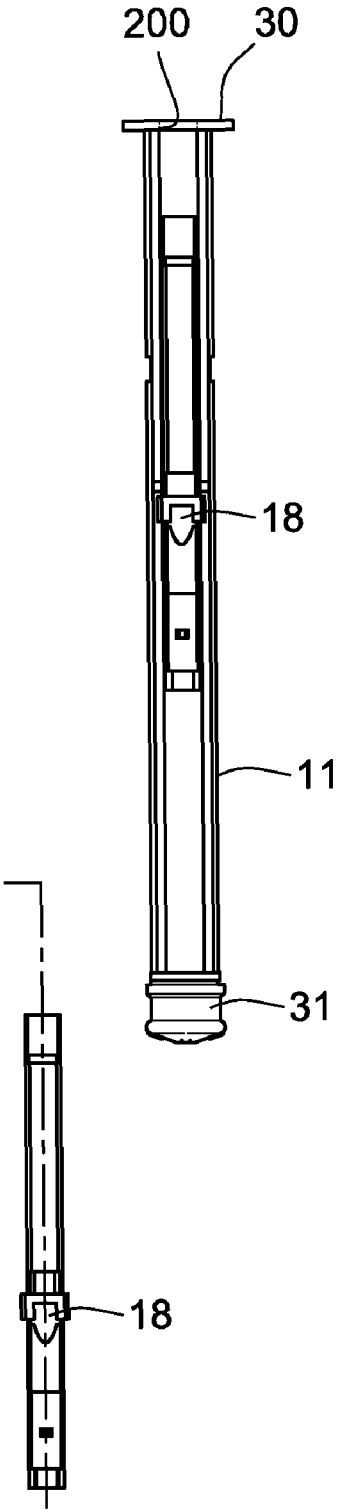

UNIVERSAL SAFETY SYRINGE

FIELD OF THE INVENTION

The present invention relates generally to syringes, and more particularly to syringes for injection and/or removal of fluids, aerosols, or particulate suspensions from humans or animals.

BACKGROUND OF THE INVENTION

Contaminated Needle Sticks and Microbial Transmission

Syringes are used for a multitude of applications. Typically, a syringe is a simple axial piston pump with a plunger that fits tightly in a cylindrical tube. The plunger can be pulled and pushed along the inside of the tube (or "barrel"), thereby creating a pressure gradient. Many syringes carry a sharp and penetrating hollow needle that is intended to puncture the skin, mucous membrane and internal organs of humans or animals for injection or removal of fluids, aerosols, or particulate suspensions.

Hypodermic syringes when used on patients may become contaminated by dangerous and often lethal microbes. The syringe can transmit the microbes to the administering or assisting physicians, nurses, healthcare workers, and sanitation workers by accidental needle sticks. The U.S. Congress has enacted a "Needlestick Safety and Prevention Act," Pub. L. 106-430, 114 Stat. 1901-1904 (2000), which makes use of engineered safety devices mandatory.

Hypodermic syringes and needles are responsible for 29% of accidental needle sticks. In addition to the possibility of dangerous infections, accidental needle sticks are also responsible for enhancement of the healthcare cost, which may amount to $3500 for each incident of needle stick injury.

Devices intended to prevent needle sticks are available and include needle covering devices, such as sheaths or sleeves that are pulled on the hypodermic needles after use. Hinged devices or sliding devices that cover the used needles are called "safety" needle devices. Mechanical cutters of needles, pulverizers, and electrical evaporators of needles are all currently used. However, the best protection may be offered by the retractable devices which ensure that the needle is not accessible to injure anyone after the use.

Desirable Characteristics of Devices with Safety Features

Improved engineering controls are often among the most effective approaches to reducing occupational hazards, and therefore are an important element of a needle stick prevention program. Such controls include eliminating the unnecessary use of needles and implementing devices with safety features. A number of sources have identified the desirable characteristics of safety devices [OSHA 1999c; FDA 1992; Jagger et al. 1988; Chiarello 1995; Quebbeman and Short 1995; Pugliese 1998; Fisher 1999; ECRI 1999]. These characteristics include the following:

The device is needleless.
The safety feature is an integral part of the device.
The device preferably works passively (i.e., it requires no activation by the user). If user activation is necessary, the safety feature can be engaged with a single-handed technique and allows the worker's hands to remain behind the exposed sharp end.
The user can easily tell whether the safety feature is activated.
The safety feature cannot be deactivated and remains protective through disposal.
The device performs reliably.
The device is easy to use and practical.
The device is safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merits and ultimately on its ability to reduce workplace injuries. The desirable characteristics listed here should thus serve only as a guideline for device design and selection.

Needle Stick Prevention & Infection Control

There are several retractable syringes that are commercially available, e.g., an Integra™ syringe, manufactured by Becton, Dickenson, and Co. (BD) of Franklin Lakes, N.J., a VanishPoint® syringe, manufactured by Retractable Technologies, Inc. (RTI), of Little Elm, Tex., a saf-T-syringes™ syringe, manufactured by Safety Medical International, Inc., of Apopka, Fla., OMI Syringes™, manufactured by Occupational & Medical Innovations (OMI) Ltd., of Slacks Creek, Australia, and Unitract Syringes™, manufactured by Unilife Medical Solutions, of Sydney, Australia. In these examples, a nozzle installed spring surrounding the needle retracts the needle inside the hollow plunger of the syringe. All these syringes require creating a communication between the barrel cavity and the plunger cavity by cutting the rubber stopper or displacing a rubber plug, which has the following shortcomings:

(a) This mechanical operation requires a voluntary act on the part of the user. Such devices are active and user dependent. These devices do not operate passively, which is the preferred mode for ultimate safety of syringes.
 (b) The impact of active manipulation of cutting or breaking the rubber seal is transmitted to the needle point while the needle is still in the patient's body.
 (c) When the needle is taken out of the patient's body and retraction is initiated, there is danger of aerosol and microbial spread to others during the retraction process.
 (d) The retractable needle syringes are not tamper proof, and there are many instances where the contaminated needle, floating free in the plunger cavity of these syringes, can escape and cause needle stick injury and microbial transmission.
 (e) They are therefore required to be disposed of in sharps containers, for safe disposal, as are other needles and syringes.
 (f) Despite engineered safety imparted to the devices, remain unsafe after use and need disposal in the sharps containers. Disposal in sharps containers is an expensive luxury and is not available, nor affordable, in many countries.
 (g) An unscrupulous person can still use these retractable needle syringes and not initiate the retraction, and then re-use them.

Unsafe Injections in Developing World

The accidental needle stick and microbial transmission is the sole problem focused on in the United States, Canada, Australia and Western Europe. Major hazards posed by hypodermic syringes are not addressed by the legislation passed by these countries, including the "Needlestick Safety and Prevention Act" in the United States.

One major hazard is the re-use and improper sterilization of the disposable contaminated syringes. Re-use of syringes is rampant in India, Pakistan, China, Southeast Asian countries and Africa. Several United Nations reports and publications have highlighted this hazard, but a solution is not in sight because often the culprits are those who have responsibility to administer healthcare or unscrupulous workers who permit entry of used syringes into the healthcare supply chain. ("Seventy per cent syringes unsafe in India," The Hindu, 17 Dec. 2004; Bull World Health Organ, 1999, 77(10):789-800; "Unsafe injections in the developing world and transmission of blood borne pathogens: a review," Simons L, Kane A, Lloyd J, Saffron M, Kane M. World Health Organization, Geneva, Switzerland.)

Cause of Unsafe Injection is Re-using of Syringes

The existing legislation and education programs have proved futile. Every re-used unsafe syringe already carries a prominent "DO NOT RE-USE" label. Most often glass syringes that can be boiled to sterilize and used are less expensive than disposable sterile plastic syringes. The cost of sterilization in those countries is low in comparison to pre-sterilized disposable syringes which are expensive, and remain expensive because they are not used on a mass scale. Even the disposable plastic syringes are re-used by boiling again and again. Finally the governments of many countries are frustrated and have resorted to syringes that would destroy themselves so that they cannot be re-used. The gravity of the re-use problem compels these governments to totally neglect the more serious and deadly situation of needle stick injury and microbial transmission. AIDS and hepatitis are rampant and growing to epidemic proportions because of this dual malady.

Relevant Re-Use Prevention Art

The irony of the current situation is the fact that although syringes are intended to be disposable, they are not. They are made from plastic that is durable.

Most of the re-use prevention art relies on breaking one of the parts of the syringe, preferably the plunger, by the user voluntarily or in an attempt to re-use. One auto-destruct syringe marketed in India relies on a ring at the nozzle of the barrel which locks the plunger when medicine is injected. The plunger is intentionally made weak. On pulling back for re-use, it breaks. However, the hypodermic needle is still exposed to cause needle stick and spread infection, and culprits will re-use the contaminated needle anyway.

Another auto-destruct syringe used for immunization carries a clip in the barrel. After injection, the clip locks the syringe. The needle is intact and unsafe. Yet another auto-destruct syringe employs a unique plunger-breaking mechanism which is "clinician-activated," to eliminate any possible re-use of the syringe. This mechanism allows the user to draw the medicine more than once, unlike a single dose injection, and then break the syringe after use. The control is therefore in the user's or clinician's hands, thus eliminating wastage. The needle remains unsafe, to spread blood-borne infections.

Inadequate Sharps Disposal in Developing Countries

About 75% of the world has no reliable system for disposition of used contaminated syringes/sharps. Sharps container service is neither available nor affordable. Even if sharps containers are provided, workers will re-use the syringes rather than using sharps containers, because re-use is more profitable.

Syringe manufacture and distribution is a global business, and there is no way to control the traffic or enforce safety requirements for these devices. Implementation of the use of specific single-use devices is impossible because these two different worlds have different objectives, and different messages. While developed countries strive to protect its people from contaminated needle sticks, the slogan for the developing world is "one syringe, one injection." Users cannot be relied upon to resolve these problems, and thus there is a need for a universal syringe that will not be under the control of its user for safety and will ensure safety by its own mechanism.

SUMMARY OF THE INVENTION

The purpose of one embodiment of the present invention is to provide a universal safety syringe that will (1) automatically retract the needle at the completion of the injection to assure prevention of needle sticks and microbial transmission, (2) self-disable after the first use and cannot be tampered with and re-used, and (3) securely lock its own retracted needle inside the barrel and will not need a sharps container for disposal. This embodiment will assure universal safety, prevent infections, and comply with safety device regulations, no matter in which country of the world it is being used.

As a matter of fact, this universal safety syringe is not classifiable as a sharps device because of its functionality. The blood borne pathogens standard defines "contaminated sharps" as "any contaminated object that can penetrate the skin, including but not limited to needles, scalpels, broken glass, broken capillary tubes, and exposed ends of dental wires." Scalpels and blades are included in this definition. (References: [1] OSHA-Definition of contaminated sharps; engineering controls and good work practice controls that must be implemented; ECP must be reviewed annually. Jun. 3, 2005. [2] Johns Hopkins Safety Manual *Policy Number* 3, HSE 805 *Subject: Last Review Date Sep.* 21, 2007 Laboratory Waste Disposal-SHARPS DISPOSAL. [3] This SOP is approved by Cornell's Institutional Animal Care and Use Committee (IACUC) and by the Cornell Center for Animal Resources and Education (CARE).)

One purpose of certain embodiments of this invention is to convert the potentially sharp hypodermic syringes into non-sharp devices because of auto retraction at the end of injection. In so doing, the needle is not exposed and, because of tamper-proof locking, the needle is in its own safety container and incapable of causing needle sticks. A syringe that is not capable of penetrating the skin after its use is not a sharps device destined for sharps containers which are expensive.

Another purpose of certain embodiments of this invention is to provide a universal safety syringe where the hypodermic needle retracts immediately as the injection is completed, while it is still in the body of the patient and is not in the environment to cause any needle stick injury to anyone. Further, the retracted needle is irretrievably locked inside the body of the interlocked and auto-disabled syringe; this design is not definable as a sharps device and may not need disposal in sharps containers, thereby saving expensive disposal methods. Resources wasted on sharps containers can be utilized in developing non-sharp syringes.

An additional purpose of certain embodiments of this invention is to provide a universal safety syringe where all the safety features such as retraction of the needle at end of the injection of the medicine, as well as auto disablement, are totally passive so that no action on the part of the user is necessary. The syringe operates as an autonomous precision machine without any control of the operator, and remains safe despite the intentions of a user.

The engineering solutions of these problems are complex and counter productive. The Needlestick Safety and Prevention Act requires that syringes intended to prevent needle sticks and infection must retract the needle and lodge it inside the center of the plunger. The anti-re-use legislation requires auto-destruct syringes that destroy certain parts of syringe, particularly the plunger, to prevent re-use. However, the destruction of the plunger can release contaminated and retracted needles and thereby create health hazards. One solution to these problems is to permanently disable the syringe rather than destroying the components.

Yet another purpose of certain embodiments of this invention is to provide a retraction control system that can be adapted to a variety of unsafe syringes to convert them into auto-retractable safety syringes.

A further purpose of this invention is to provide an assembly method for auto-retract, and auto-disable universal syringes that cannot be assembled by the conventional syringe assembly methods and existing continuous motion syringe assembly machine technology.

In accordance with one exemplary embodiment, a safety syringe assembly comprises an elongated, generally cylindrical barrel having a hollow interior forming a hollow nozzle located at a distal end of the barrel and opening into the interior of the barrel, a plunger slidably mounted in the barrel and having a longitudinal open channel, a needle, a needle holder mounting the needle at a distal end thereof and slidably mounted in the longitudinal open channel of the plunger for movement between an advanced position in which the needle on the distal end of the needle holder projects from a distal end of the nozzle, and a retracted position in which the needle is fully enclosed within the barrel, a spring retainer between the barrel and the needle holder, a compressed spring positioned within the spring retainer the urging the needle holder toward the retracted position, and a latch latching the needle holder to the retraction tube to maintain the spring in compression, the first latch being releasable in response to advancing movement of the plunger to its fully advanced position, whereby the needle holder is released from the retraction tube to allow the compressed spring to expand and thereby move the needle holder to the retracted position.

One implementation also includes a second latch latching the plunger to the barrel in response to advancing movement of the plunger to a predetermined advanced position, to prevent movement of the plunger relative to the barrel after the needle has been retracted within the barrel.

The above summary of the present invention is not intended to represent each embodiment, or every aspect, of the present invention. The above features and advantages, and other features and advantages of the present invention, will be readily apparent from the following detailed description of the preferred embodiments and best modes for carrying out the present invention when taken in connection with the accompanying drawings and appended claims.

BRIEF DESCRIPTION OF THE DRAWINGS

FIG. 2 is a longitudinal section taken through the center of the syringe of FIG. 1, with the addition of a detachable needle protector cap.

FIG. 3 is the same section shown in FIG. 2 with the plunger in its fully retracted position.

FIG. 4 is the same section shown in FIG. 2 with the plunger in its fully advanced position, and the needle in its fully retracted position.

FIG. 18 is an enlarged perspective view of the spring retainer in the syringe of FIGS. 1-4.

FIG. 19 is the perspective view of FIG. 18 with the proximal portion of the spring retainer shown in longitudinal section.

FIGS. 25 is a side elevation of an optional manual switch for use with the syringe of FIGS. 1-4.

FIGS. 26 is an end elevation taken from the right-hand end of the manual switch as shown in FIG. 25.

FIG. 27 is an enlarged section taken along line 27-27 in FIG. 25 with the switch installed in the syringe of FIGS. 1-4.

FIG. 29 is a perspective view of the manual switch shown in FIGS. 25-28.

FIGS. 30a-30i illustrate the sequential steps of assembling the syringe of FIGS. 1-4.

DETAILED DESCRIPTION OF THE ILLUSTRATED EMBODIMENT

Figure 1:
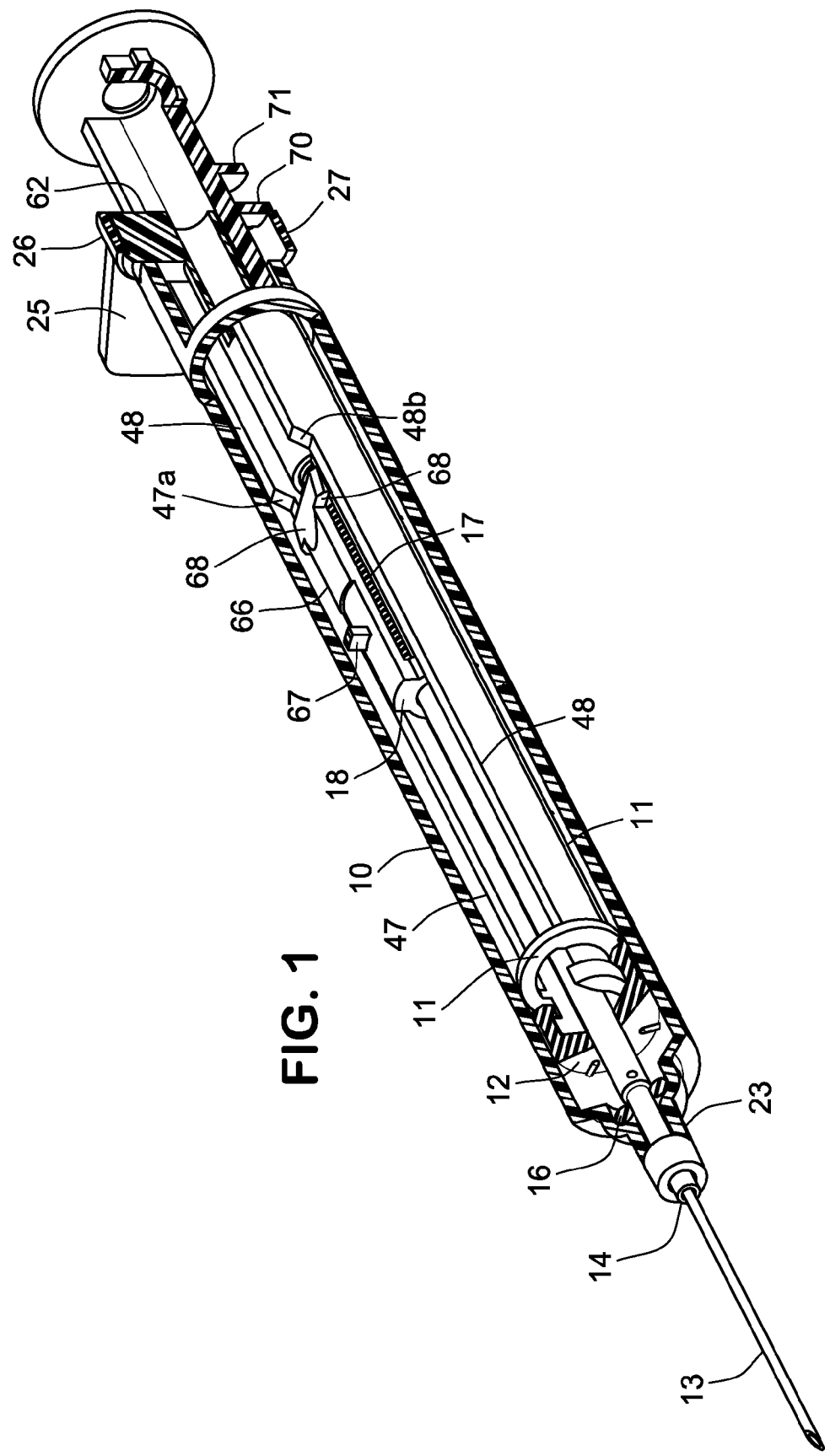
FIG. 1 is a perspective view of a safety syringe with its needle in the fully advanced position, with portions of the barrel, plunger and plunger cap sectioned to reveal the internal structure.
Figure 5:
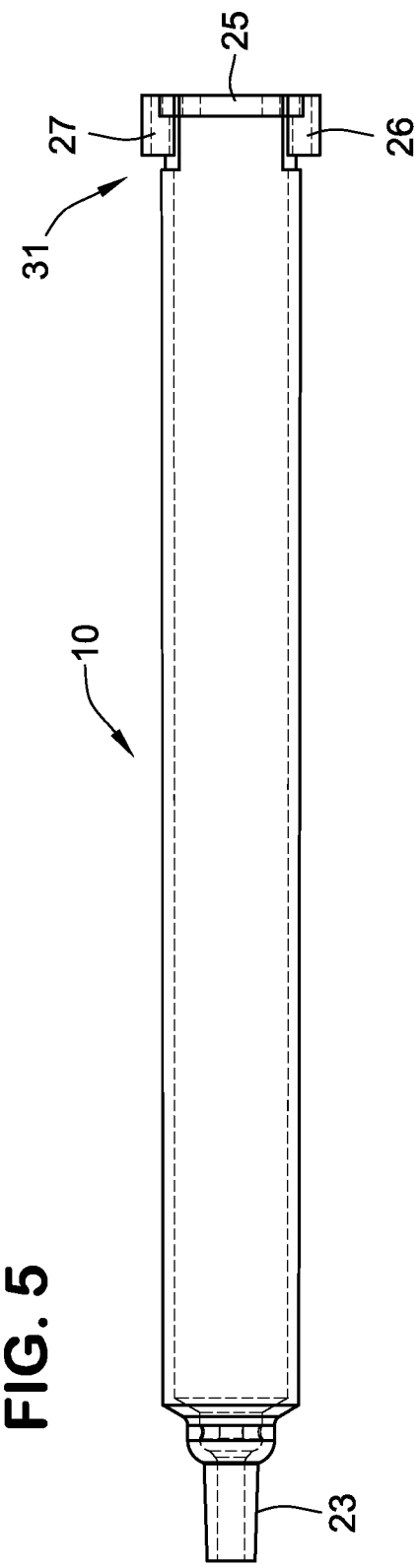
FIG. 5 is a side elevation of the barrel in the syringe of FIGS. 1-4.
Figure 6:
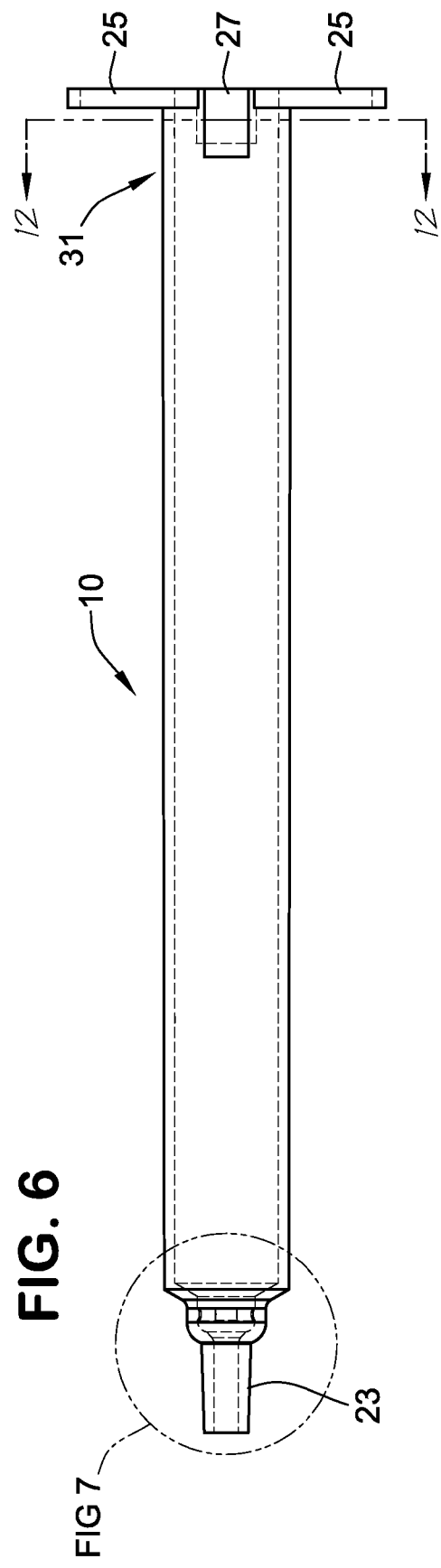
FIG. 6 is a side elevation of the barrel of FIG. 5 rotated 90° (around the longitudinal axis of the barrel) from the position shown in FIG. 5.
Figure 7:
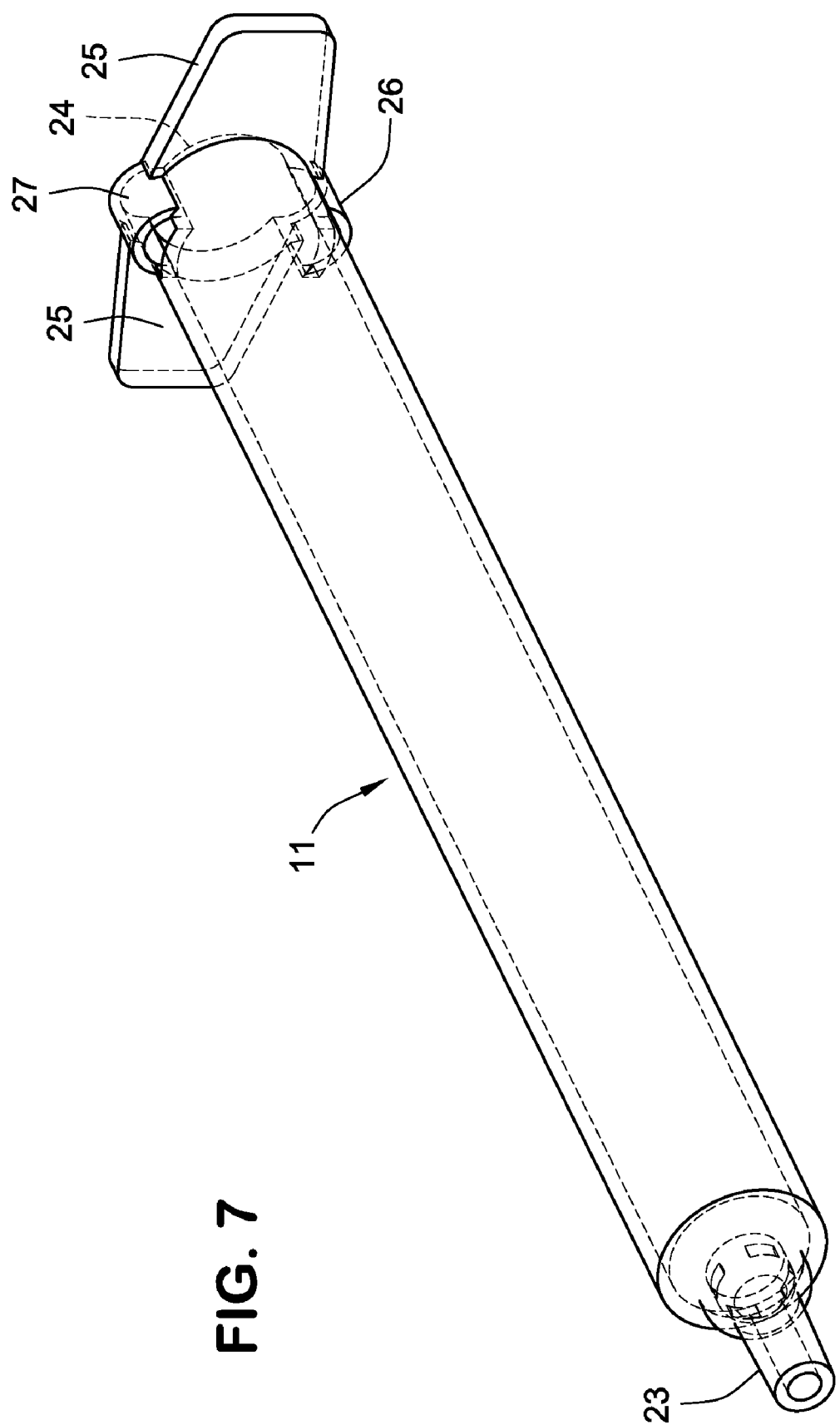
FIG. 7 is a perspective view of the barrel of FIGS. 5 and 6.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Several different embodiments of the invention, each with its own unique features and alternate embodiments, will be described. Permutations and combinations of these features will, however, lead to further embodiments.

Turning now to the drawings, and referring first to FIGS. 1-4, a safety syringe assembly includes a barrel 10, a plunger 11, a hollow resilient (rubber) plunger cap 12 (sometimes referred to as the "rubber piston" or "rubber stopper"), a hypodermic needle 13 and a needle holder 14. The syringe also includes a needle protector cap 15 mounted on the distal end of the barrel 10, and an O-ring 16, a spring 17 and a spring retainer 18 within the barrel 10.

FIGS. 2-4 depict the syringe in three different states. In FIG. 2, the syringe is generally in a condition in which it is assembled, packaged and shipped, e.g., prior to use. It can be seen that the needle 13 is in its advanced position with the needle protected by the cap 15, and the plunger 11 is in a partially, but not fully advanced position within the barrel 10. Thus, in the illustrated example of FIG. 2, the syringe is ready to draw a liquid into the barrel 10, via the needle 13, for example, by retracting the plunger 11, e.g., to the position illustrated in FIG. 3. It can be seen from FIG. 3 that retracting the plunger does not substantially change the position of the needle 13 or the needle holder 14. As will be described in detail below, a first latch locks the needle holder 14 and, thus, the needle 13 in the advanced positions shown in FIGS. 1-3, and holds the spring 17 in its compressed condition. In the illustrated embodiment, the first latch is released when the plunger 11 is advanced to the position shown in FIG. 4, thereby allowing the spring 17 to expand and automatically retract the needle holder 14 and needle 13 into the barrel 10.

In FIG. 4, the plunger 11 has been fully advanced, with the plunger cap 12 engaging the distal end of the main portion of the barrel interior. Likewise, the needle 13 and the needle holder 14 have been retracted by expansion of the spring 17. It can be seen in FIG. 4 that the needle 13 is sufficiently retracted such that the sharp end is completely enclosed within the barrel 10. As will be described in detail below, a second latch preferably automatically locks the plunger 11 to the barrel 10 when the plunger is advanced to the position shown in FIG. 4, thereby preventing re-use of the syringe.

Figure 8:
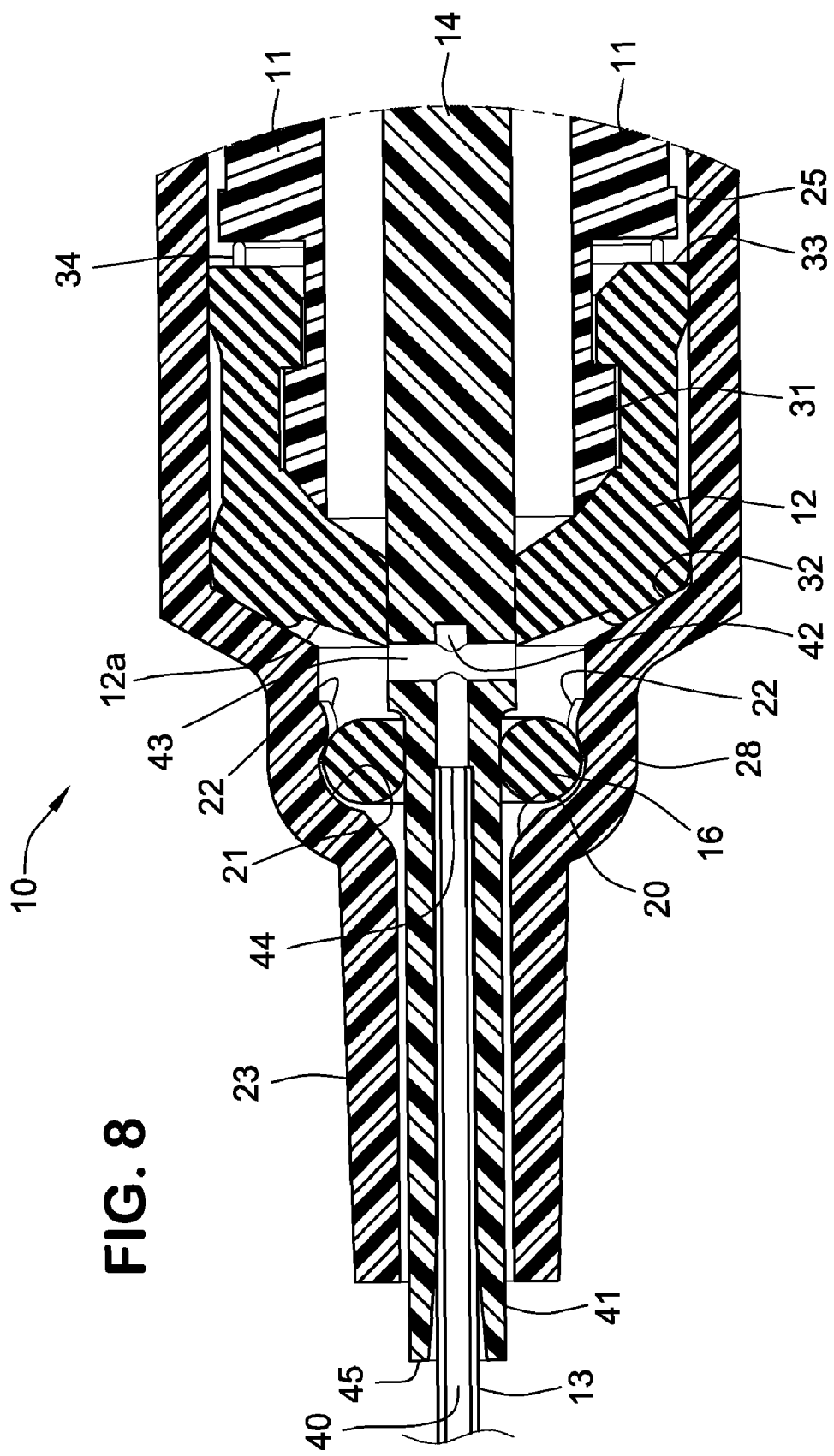
FIG. 8 is an enlarged view of the distal portion of the syringe shown in FIG. 4, but with the needle in its advanced position.
Figure 12:
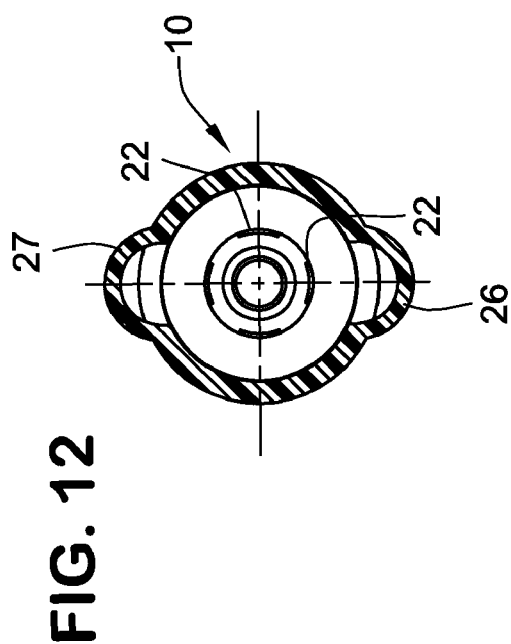
FIG. 12 is a section taken along line 12-12 in FIG. 6.

The barrel 10 shown in FIGS. 1-12 has specifically designed functional features. The barrel 10 is an elongated, hollow tube, shown generally as a right circular cylinder, which, at its distal end, forms a generally frustoconical chamber 20 that includes a recess 21 (see FIG. 8) for receiving the elastomeric O-ring 16. With reference to FIG. 8, a number of elevated molded retainers 22 (four in the illustrated embodiment) on the proximal side of the O-ring recess 21 capture or otherwise retain the O-ring 16 in the recess 21. On the distal side of the conical chamber 20, the barrel 10 terminates in a hollow tapered nozzle 23, which communicates with the hollow interior of the tubular body portion of the barrel 10. Desirably, the barrel 10 has a uniform diameter until its open margin 24 (seen in FIG. 7). The barrel margin 24 of the illustrated embodiment has a pair of integrally-formed, outwardly extending diametric flanges 25, desirably formed with friction lines (not shown) which facilitate counterbalancing the barrel with the user's fingers when it is desired to move the plunger 11 longitudinally relative to the barrel 10 for normal use in withdrawing or injecting medicine.

With continuing reference to the depicted exemplary embodiment of FIGS. 1-12, the barrel margin 24 is also provided with a pair of locking sleeves or pockets 26 and 27 on the outer cylindrical wall of the barrel. The first locking pocket 26 is configured to receive a locking projection on the spring retainer 18, and the second locking pocket 27 receives a pair of locking projections on the plunger 11 when the plunger is fully advanced, thereby firmly locking the spring retainer 18 and the fully advanced plunger 11 to the barrel 10, as described in more detail below. Ideally, the locking pockets 26 and 27 are centered on a transverse axis that is perpendicular to the transverse axis on which the flanges 25 are centered (see FIGS. 7, 11 and 12). Alternatively the locking pockets 26, 27 may be replaced with diametric windows that form locking means for structures inserted transversely rather than longitudinally.

FIG. 8 is an enlarged cross-sectional side-view of the distal end portion of the barrel 10, whereat fluid enters the syringe through the needle 13, and may be injected, for example, into a patient's body through the same needle 13. The medicine resides in a generally fluid-tight chamber cooperatively defined between a conical surface 12a of the plunger cap 12, the inside of barrel walls 28, the OD surface of the needle holder 14 in the center, and the O-ring 16 at the distal end. The fluid chamber expands, for example, when the plunger cap 12 is moved away from the O-ring 16, thereby acting to draw fluid in, and shrinks or collapses when the plunger cap 12 is moved toward the O-ring 16, thereby discharging fluid from the syringe.

Fluid (e.g., medicine) enters and exits through needle holder openings 43, 44. This is relevant to the fluid remaining in the syringe after injection is completed. "Residual volume" is the amount of fluid remaining in the syringe after the completion of injection, and represents fluid remaining in the needle, or in a space that does not communicate with the needle exit port. FIG. 8 shows that the proximal end of the needle 13 is in fluid communication with the fluid chamber defined, at least partially, by the plunger cap 12 and the O-ring 16, both of which are preferably formed of a compressible material, and cooperatively empty the last volume of fluid from the chamber as the plunger 11 reaches its fully advanced position in the barrel and the compressible materials return to their normal shapes.

Referring back to FIG. 1, the needle protector cap 15 protects the sharpness of the puncturing needle 13, as well as protecting from inadvertent needle sticks until the cap 15 is removed for use. The cap 15 also provides an air-and watertight closure of the nozzle 23 before use, and after use it prevents leakage of any contaminant so that the entire syringe can be disposed of in biological waste. The cap 15 and nozzle 23 may have interlocking luer tapers, or even threads, to secure the cap 15, for a pre-filled syringe, for example.

The outer surface of the barrel 10 may contain graduations indicating the volume level of fluid in the barrel. These graduations take into account the volume of the internal components, such as, for example, the needle holder 14.

The plunger 11 of the present invention is unconventional as is shown in FIGS. 13-17. The proximal end of the plunger 11 forms a preferably circular thumb plate 30 that can be grasped or pushed by a user to effect longitudinal movement of the plunger 11 relative to the barrel 10. The periphery of the thumb plate 30 can be serrated or engraved to prevent slippage during use of the plunger.

Figure 10:
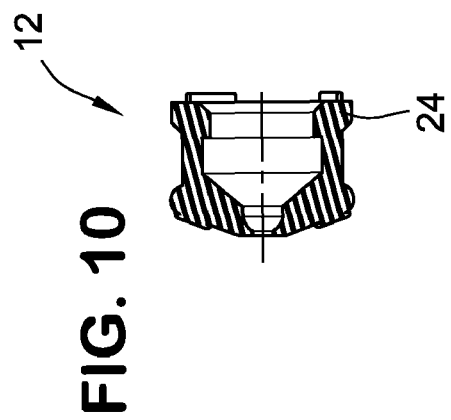
FIG. 10 is a longitudinal section through the plunger cap in the syringe of FIGS. 1-4.
Figure 11:
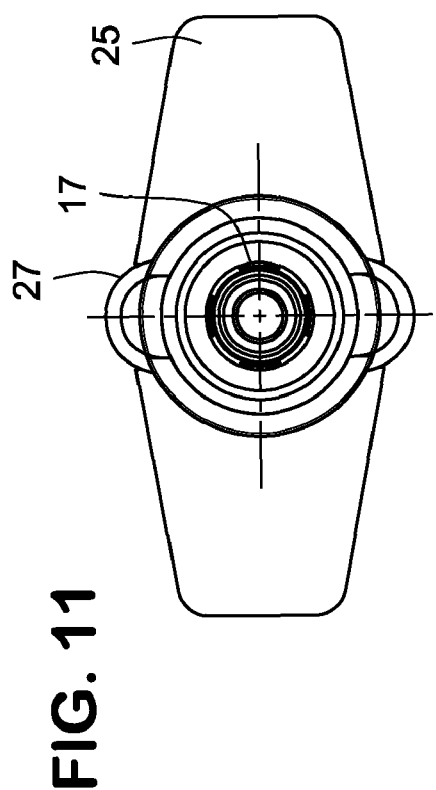
FIG. 11 is an enlarged end elevation of the syringe of FIG. 1.
Figure 9:
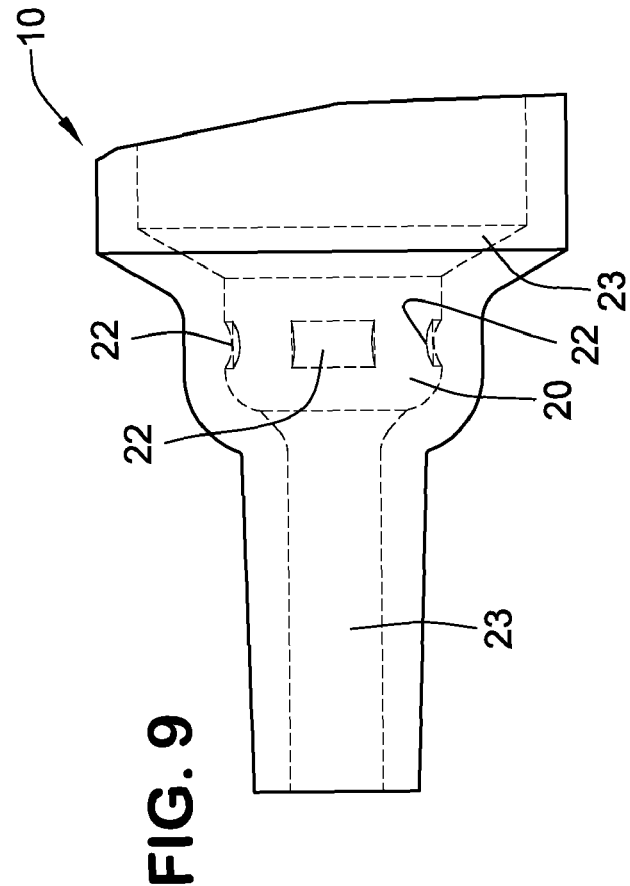
FIG. 9 is an enlarged side elevation of the distal and portion of the barrel of FIGS. 5-7.
Figure 13:
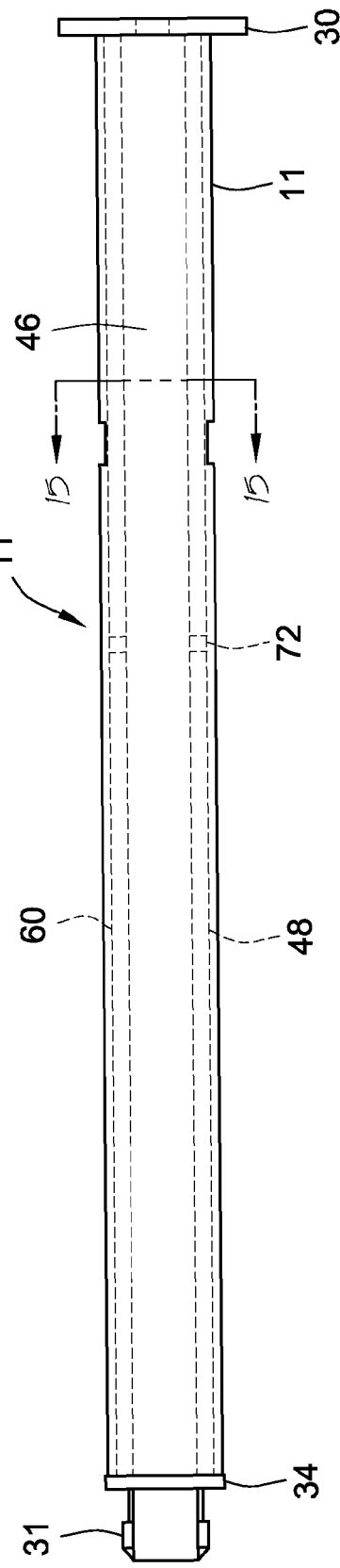
FIG. 13 is a side elevation of the plunger in the syringe of FIGS. 1-4.

The distal end of the plunger 11 forms a head 31 for mating with and mounting the hollow rubber plunger cap 12 on the plunger 11. As seen in FIGS. 8 and 10, the outside diameter of the resilient cap 12 is reduced along a central portion thereof so that the cap 12 engages the inside wall of the barrel 10 only at the pliable margins of the ends of the cap 12. In an uncompressed condition, the outer diameters of the engaging end portions of the cap 12 are slightly larger than the inside diameter of the barrel 10 so that the cap 12 presses firmly against the inside wall of the barrel to form an air-tight and liquid-tight seal at the cap/barrel interface. The inner distal margin of the cap 12 is also configured to form an air- and liquid-tight interface with the outer surface of the needle holder 14. The distal end surface 12a of the cap 12 is generally conical to compliment and generally conform to the conical distal end surface 32 of the inside surface of the barrel 10, when the plunger 11 is fully advanced within the barrel 10. This cooperative interface is intended to reduce dead space, and assure complete evacuation of fluid from the syringe. The outer wall of the cap 12 may be thickened somewhat to prevent its collapse during the in-barrel assembly process.

Referring again to FIGS. 13 and 14, the head 31 of the plunger 11 is configured to fit within the hollow plunger cap 12. With the cap 12 locked onto the head 31 of the plunger 11, the flat proximal end 33 of the cap 12 abuts a flat, forward surface of a circular disc 34 at the base of the plunger head 31. The disc 34 transmits advancing force to the rubber cap 12. Due to the air-tight and liquid-tight seal between the plunger cap 12 and the barrel 10, as well as the needle holder 14, advancing movement of the plunger 11 inside the barrel 10 creates pressure in the interior of the barrel 10 between the plunger cap 12 and the distal end of the barrel 11. Similarly, retracting movement of the plunger 11 creates a vacuum in that portion of the barrel 11 interior.

A portion of the mating surfaces of the plunger head 31 and the cap 12 are slightly spaced from each other to provide a loose fit.

The needle holder details are shown in FIGS. 2-4, 8 and 20-21. Both the needle 13 and the distal portion of the needle holder 14 are hollow. As seen in FIG. 8, the interior 40 of the hollow needle 13 communicates with the interior of the hollow distal portion 41 of the needle holder 14. The proximal end of the interior channel of the hollow distal portion 41 is blind at 42. The needle holder 14 fluidly communicates with the interior of the barrel 10 through an aperture 43 which extends laterally along a diameter of the needle holder 14, through the side walls of a hollow portion of the needle holder 14 (FIG. 8). Prior to and during use of the needle-syringe assembly—e.g., for injection of medicine (hereafter referred to as "normal use"), the side aperture 43 is positioned on the proximal side of the O-ring 16, sometimes within a small cylindrical cavity. The side aperture 43 permits fluids, such as medicine, to enter and/or exit the barrel 10 via the needle holder 14 and the needle 13. The proximal end of the needle 13 rests at a needle holder shoulder 44 and ends in the blind channel of the distal portion 41 of the needle holder 14 so that the needle does not have an "open" end on retraction, as in some prior art arrangements. Instead the needle 13 is bonded within the cavity of the needle holder 14, and fluid transport occurs through the side aperture 43 at a boundary zone.

Referring still to the embodiment of FIG. 8, the distal end 45 of the needle holder 14 may be fabricate with a tapered opening to facilitate insertion of the needle 13 into the needle holder during assembly. During normal use of the needle-syringe assembly, the needle holder 14 is indirectly locked to the barrel 10, and the plunger 11 and its rubber cap 12 are free to slide longitudinally back and forth along the needle holder 14 within the barrel 10.

Referring to FIGS. 13-17, to permit relative sliding movement between the plunger 11 and the needle holder 14 in the longitudinal direction, the needle holder 14 is mounted in a longitudinal cavity or channel 46 (FIGS. 15 and 16) formed as an integral part of the plunger 11. The needle holder 14 is generally slidable between two positions, namely, the advanced position shown in FIGS. 1-3, and the retracted position shown in FIG. 4. In some embodiments, multiple pairs of resilient retaining elements or detents (not shown) project toward each other from the opposed walls of the channel 46 to retain the needle holder 14 within the channel 46.

Figure 15:
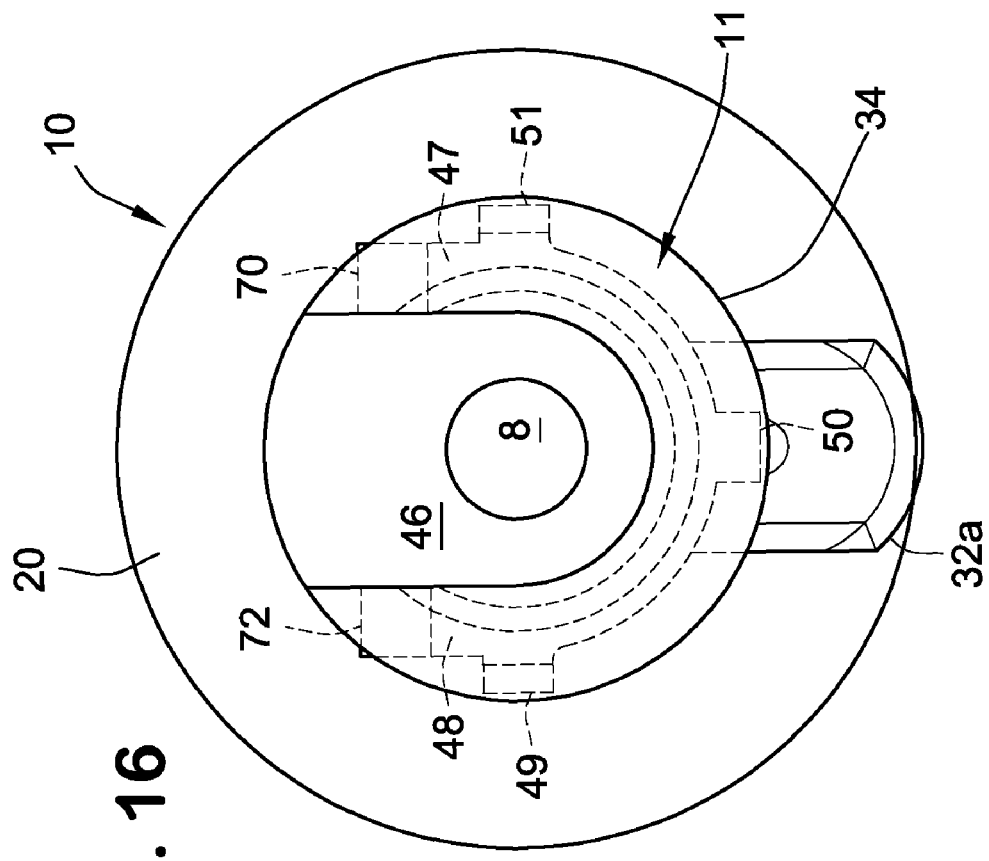
FIG. 15 is an enlarged section taken along line 15-15 in FIG. 14.
Figure 16:
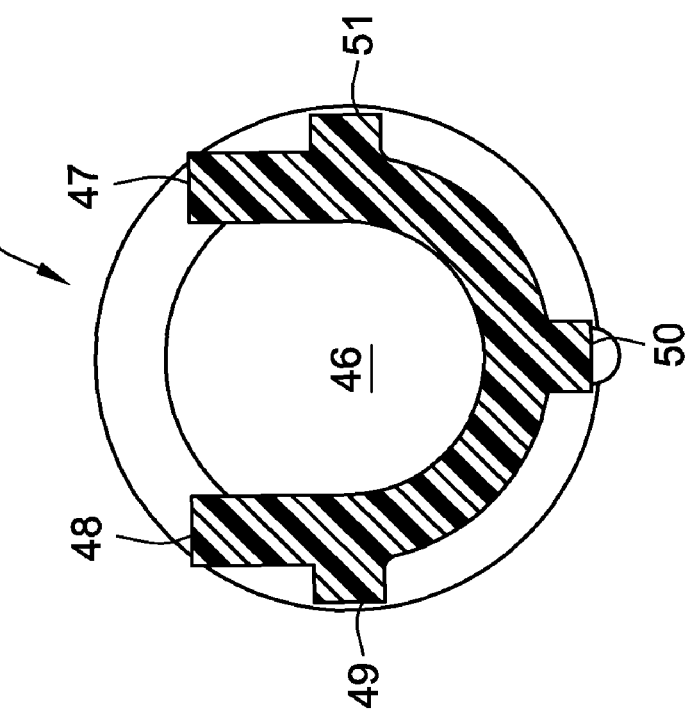
FIG. 16 is a further enlarged end elevation of the distal end of the plunger of FIGS. 13-15.

As can be seen in FIGS. 15 and 16, the plunger 11 may be fabricated with multiple ribs. By way of example, a first pair of parallel ribs 47 and 48 defines the longitudinal channel 46 for receiving the needle holder 14 described above. The lower portion of the channel 46 is semi-cylindrical, and the upper portion is formed by parallel surfaces tangential to opposite sides of the semi-cylindrical lower portion. Three additional longitudinal ribs 49, 50 and 51 extend outwardly at spaced intervals around the outer surface of the plunger 11, to engage the inside walls of the barrel 10, and thereby keep the plunger centered within the barrel 10.

Conventional syringes with barrels, plungers, and nozzle-mounted hypodermic needles are essential life-saving devices in preventive as well as curative medicine. However post-use needle sticks, and unscrupulous re-use of syringes or needles make them a lethal weapon. One objective of certain embodiments of this invention is to provide an integrated passive needle retraction and re-use control unit, that automatically retracts the post-use needle and automatically disables the syringe to prevent its re-use. When installed in any syringe, this integrated retraction and re-use prevention mechanism eliminates the dangers associated with conventional syringes yet preserves the life-saving function of this widely used device. Moreover, total automation removes the syringe from the user's control or motivation. The entire safety mechanism is consolidated in a single integrated tubular unit, as described below. The integrated retraction unit operates with indexed plunger advance, and their synchronous operation converts an ordinary syringe into a precision retracting mechanism. The unit is synchronized with the moving plunger and controls the entire syringe operation.

Referring to FIGS. 18-21, the spring retainer 18 of the illustrated embodiment consists of a unitary polymeric tube designed to provide support to the compression spring 17 around the entire circumference of the spring. The distal end of the spring 17 is supported by an internal shoulder 60 (see FIG. 21) near the distal end of the spring retainer 18. In one embodiment, when compressed to a solid length, the spring 17 exerts a force of 2.5 to 4 pounds. The proximal end of the spring 17 presses against a forward surface of a head 61 on the proximal end of the needle holder 14, which preferably extends concentrically along the common central axis of the spring retainer 18 and the compressed spring 17. The tubular configuration illustrated in the drawings assures that the needle holder 14 remains straight and does not deflect sideways during operation of the plunger or retraction of the needle holder. According to a preferred practice, the central longitudinal axis of the spring retainer 18 is precisely located in the center of the plunger cavity to assure that the needle holder 14 is advanced in a straight line and that the retraction axis is also in a straight line.

The spring retainer 18 is locked to the barrel 10 by a side cantilever 62 (seen in FIGS. 1-4 and 18-21) having a locking flange 63 (FIGS. 2-4) extending radially outwardly from the distal end of the cantilever 62. The cantilever 62 is interference fit into the locking pocket 26 of the barrel 10. The cantilever 62 is pushed into the locking pocket 26 during assembly, elastically deforming or distorting the sleeve 26 sufficiently to allow the locking flange 63 to pass through the pocket 26. When the locking flange 63 passes completely through the pocket 26, the pocket 26 returns to its normal shape and the flange 63 snaps outwardly to overlap a portion of the distal end of the pocket 26. In a preferred embodiment, this mating interface prevents any subsequent detachment of the spring retainer 18 from the barrel 10—i.e., the locking of the spring retainer 18 to the barrel 10 is permanent.

To hold the spring 17 in a compressed condition between the spring retainer shoulder 60 and the needle holder head 61, a latching projection 64 (FIGS. 18 and 19) extends radially inwardly from the interior surface of the spring retainer 18 to overlap a portion of the needle holder head 61. This projection 64 forms part of the first latch referred to above, which holds the spring 17 in its compressed condition, and locks the needle holder 14 and, thus, the needle 13, in their advanced positions shown in FIGS. 1-3. As can be seen in FIGS. 18 and 19, a generally U-shaped opening 65 is formed in the distal half of the spring retainer 18 to form a semi-flexible, resilient segment 66 having a free proximal end 66a and a fixed distal end 66b that is preferably integral with the spring retainer 18. In the illustrated embodiment, the width of the base of the U-shaped opening 65 is smaller than the inside diameter of the spring retainer 18.

Figure 20:
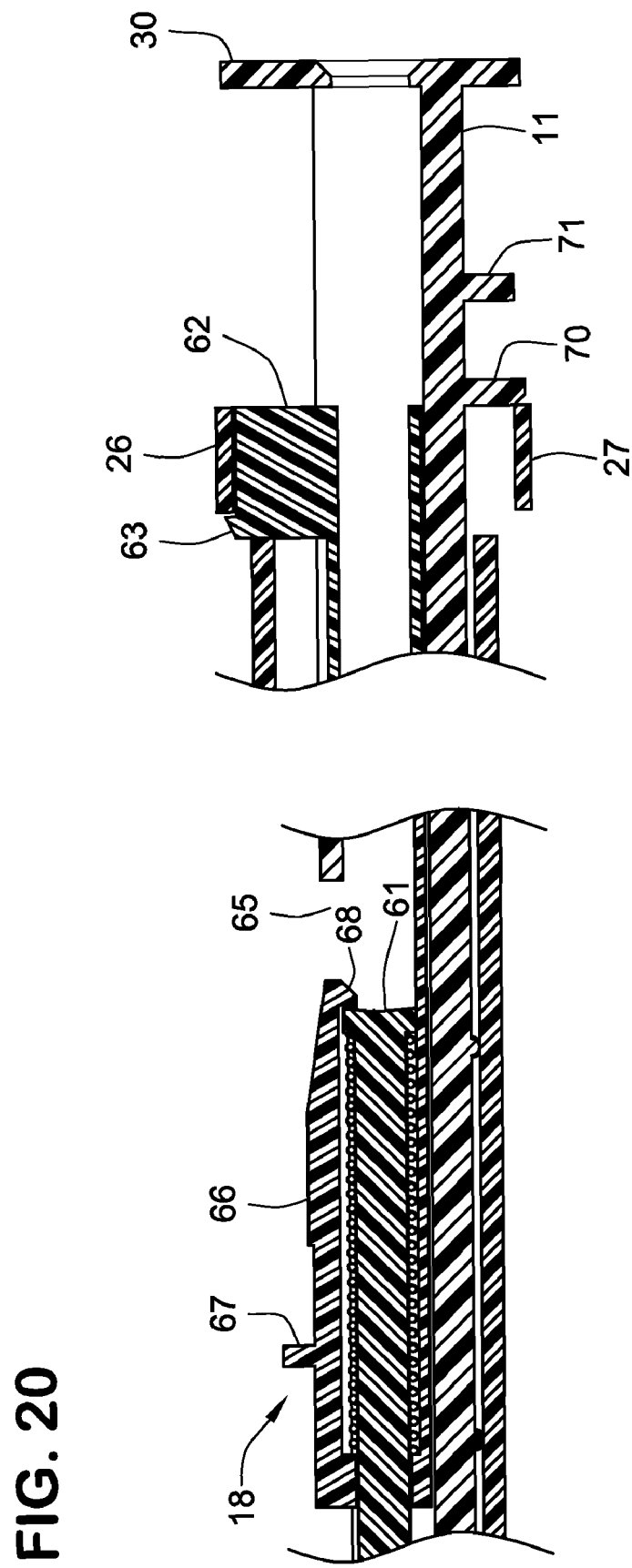
FIG. 20 is an enlarged view of portions of the section shown in FIG. 2 with the barrel removed and with the remainder of the syringe rotated 180° (around the longitudinal axis of the syringe) from the position shown in FIG. 2.
Figure 21:
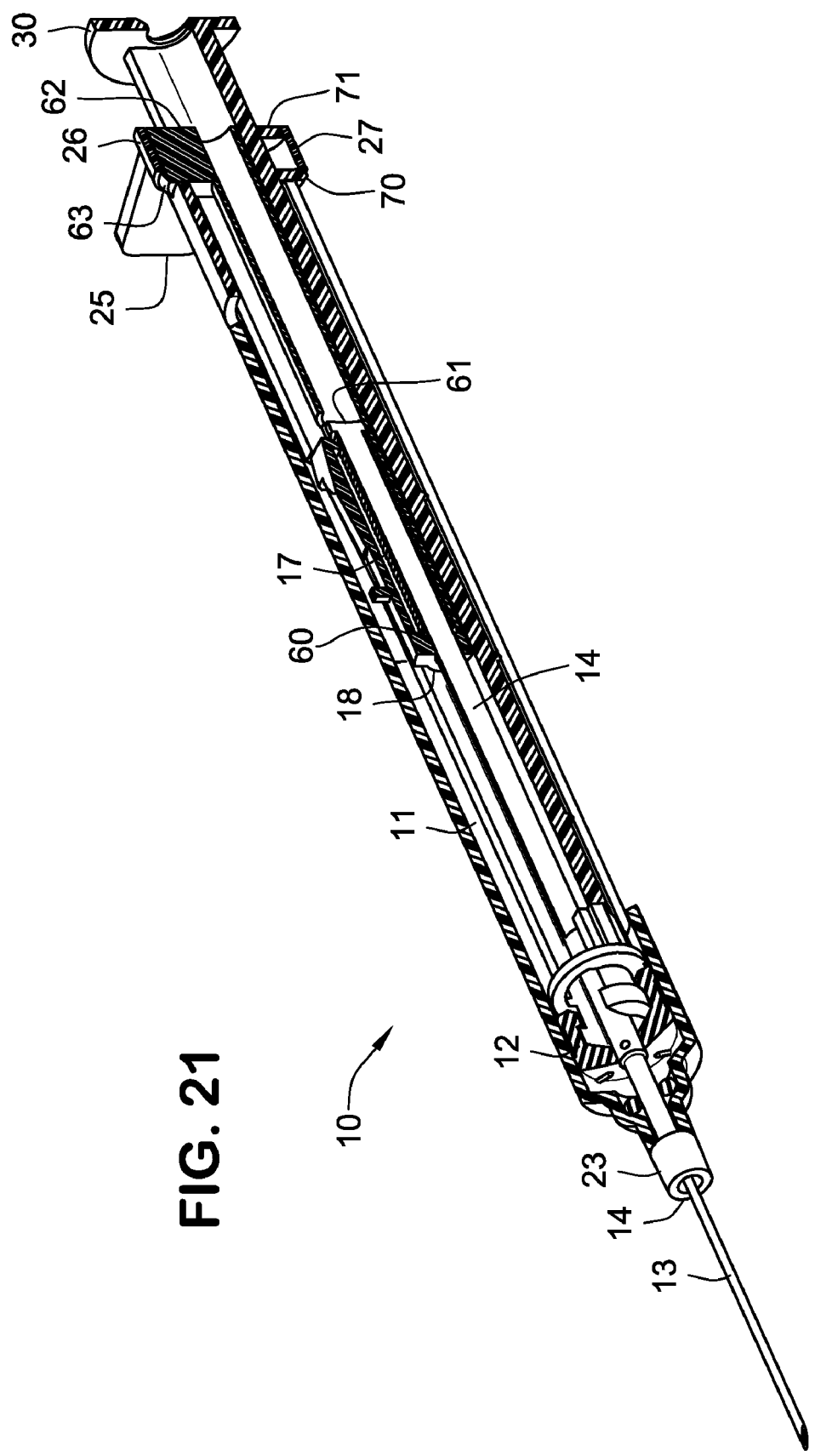
FIG. 21 is a perspective view of the syringe of FIG. 1 with the needle partially retracted, and with additional portions of the plunger sectioned to reveal the internal structure.

The latching projection 64 portrayed in FIGS. 18 and 19 is formed on the inner surface of the segment 66, adjacent the free end 66a of the segment 66. The proximal side of the projection 64 is tapered so that the segment 66 is cammed outwardly when the needle holder 14 and the spring 17 are inserted into the spring retainer during assembly. When the needle holder head 61 clears the projections 64, the segment 66 returns to its normal position, with the projection 64 overlapping a portion of the head 61 to hold the needle holder 14 in its advanced position and to resist the force of the compressed spring 17. As can be seen in FIGS. 18-20, the segment 66 may be formed with an increased wall thickness for added strength. Moreover, the segment 66 may be formed with an outer projection 67 that engages the inside wall of the barrel 10 to keep both the spring retainer 18 and the needle holder 14 centered within the barrel, and within the plunger channel 46.

Figure 17:
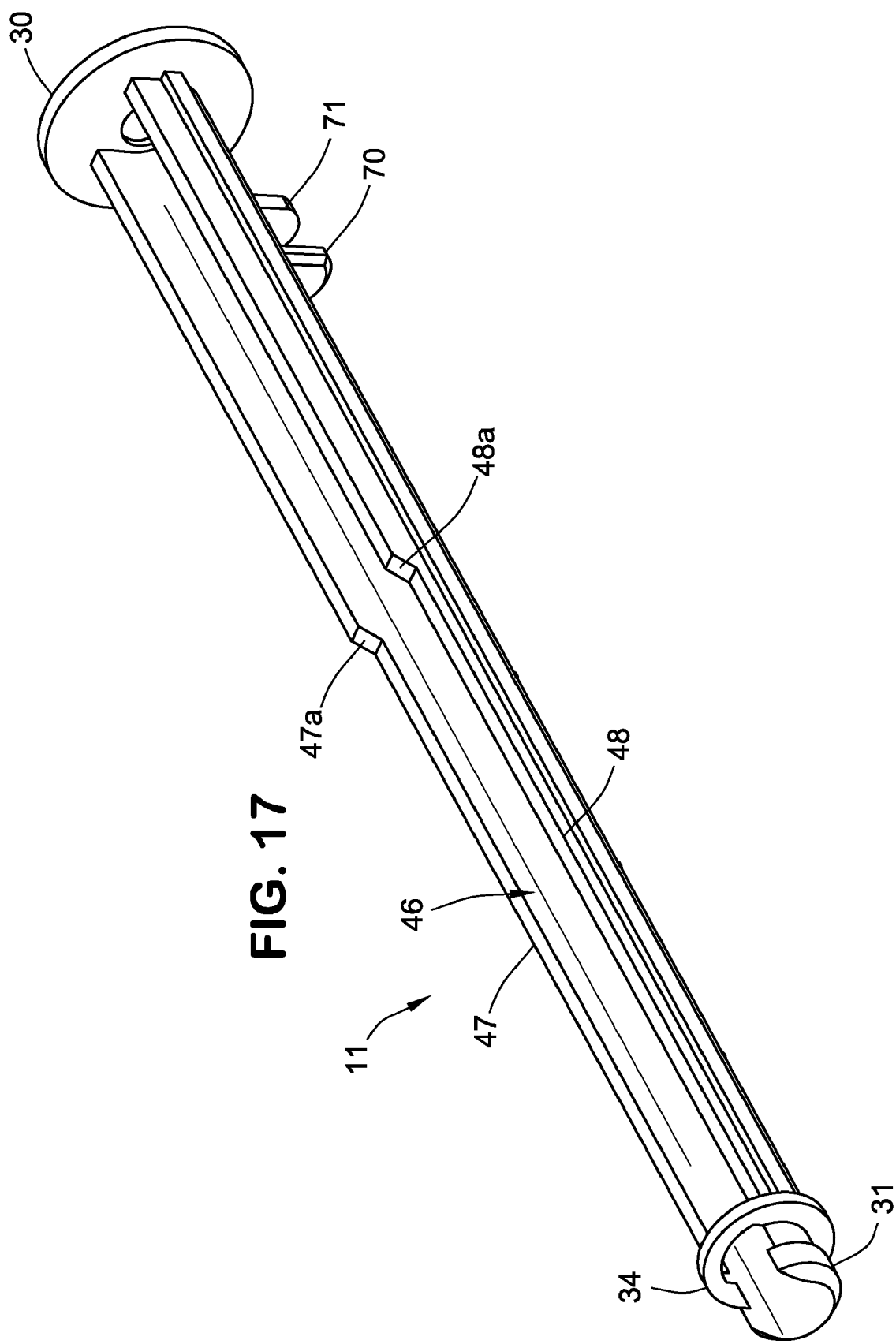
FIG. 17 is a perspective view of the plunger of FIGS. 13-15.

According to some embodiments, the semi-flexible segment 66 has two lateral projections (or "wings") 68 near its proximal free end 66a. The inner surfaces of the wings 68 lie in the same linear plane as the distal portions of the surfaces of the plunger ribs 47 and 48 that form the channel 46. As can be seen in FIG. 17, the proximal portions of the ribs 47, 48 are higher than the distal portions, and the transitions between the distal and proximal portions are tapered to form a pair of ramps 47a, 48a. These ramps function to release the spring latch formed by the projection 64 overlapping the needle holder head 61. When the ramps 47a and 47b lift the wings 68 onto the higher proximal portions of the ribs 47 and 48, the spring latch is released by outward movement of the latching projection 64. This action releases the restraining force of the projection 64 from the needle holder head 61, thereby allowing the spring 17 to expand and retract the needle holder 14 to the position shown in FIG. 4.

Continuing with the above exemplary embodiment, the external surfaces of the semi-flexible segment 66 are chamfered to assure that, when the wings 68 are deflected radially outward by the plunger ramps 47a and 48a, the segment 66 is geometrically accommodated inside the cylindrical space of the barrel 10.

In general, the plunger 11 is the sole moving part of the syringe during normal operation thereof. The plunger 11 interfaces, as described above, with the fluid chamber defined by the barrel 10 via the plunger cap 12. The linear movement of the plunger 11 within the barrel 10 determines the amount of fluid taken in and evacuated from the syringe assembly. These movements of the plunger 11 can therefore be mechanically indexed to the functional outcome of the syringe and retraction of the needle holder 14, as well as disablement of the syringe.

The amount of fluid taken into the barrel 10 depends on the length of the retracting movement of the plunger 11, which is limited by the spring retainer 18, as can be seen in FIG. 3. Consequently, by adjusting the length of the spring retainer 18, the maximum volume of liquid that can be drawn into the syringe can be fixed, e.g., to a desired dose. This feature can be useful in mass-immunization syringes or self-injection applications.

In addition to the above features, syringe assembly embodiments of the present invention may be fabricated with a disabling feature designed to prevent re-use of the syringe.

Figure 14:
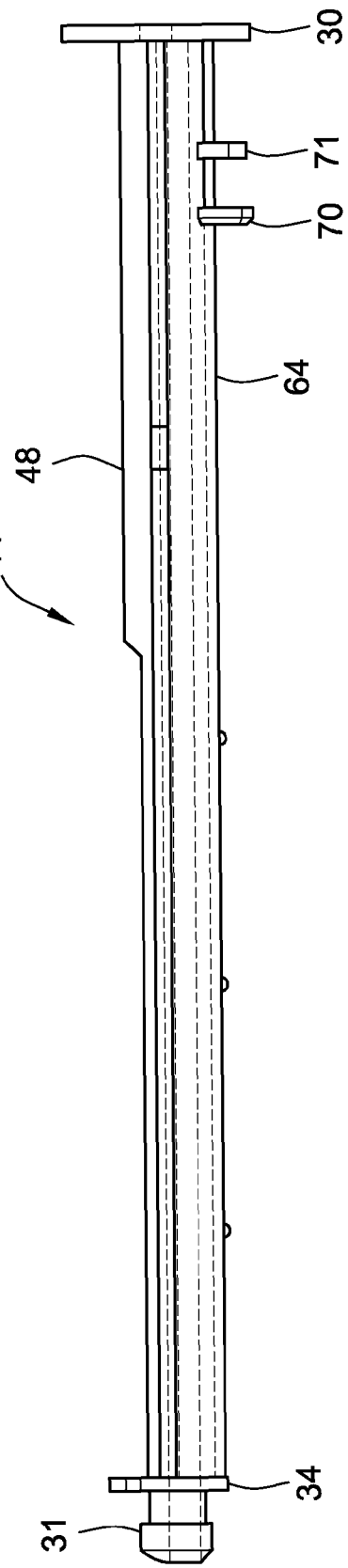
FIG. 14 is a side elevation of the plunger of FIG. 13 rotated 90° (around the longitudinal axis of the plunger) from the position shown in FIG. 13.

For instance, at the same time the spring latch is released to automatically retract the needle holder 14, the plunger-barrel latch is automatically engaged, to prevent re-use of the syringe. In one exemplary configuration, the plunger-barrel latch is formed by a combination of the locking pocket 27 on the barrel and a pair of locking projections 70 and 71 projecting radially outwardly from the plunger 11 near its proximal end (see FIGS. 1-4, 14, 17 and 20). As seen in FIG. 14, the leading projection 70 is slightly longer than the projection 71, and has a tapered surface on its distal side to facilitate its entry into the locking pocket 27 as the plunger is advanced from a retracted position (e.g., the position shown in FIG. 3) to a depressed position (e.g., the position shown in FIG. 4). As the plunger 11 is depressed relative to the barrel 10, the projection 70 is pushed into the locking pocket 27. Contemporaneously therewith, the pocket 27 and/or the projection 70 flex, distort, or otherwise deform sufficiently to allow the projection 70 to pass longitudinally through the pocket 27. When the projection 70 passes completely through the pocket 27, the projection 70 and/or the pocket 27 return to their normal shapes such that the projection 70 overlaps a portion of the distal end of the pocket 27. This prevents any subsequent retraction of the plunger 11 relative to the barrel 10 by locking the plunger 11 and the barrel together 10, thereby disabling the syringe assembly.

Like the locking pocket 26 described previously, the locking pocket 27 is integrally molded with the barrel 10. The locking pocket 27 forms sloped interior surfaces to allow the locking projection 70 to pass through. The second projection 71 has substantially the same dimensions as the locking pocket 27 and fits snugly inside the pocket to prevent any deformation of the pocket after the leading projection 70 has passed through. There is a tight tolerance between the locking parts, so that the plunger 11 is permanently locked to the barrel 10, for example, after the injection of medicine has been completed by movement of the plunger to its fully advanced position (see FIGS. 4 and 8). The interlock is largely concealed and inaccessible, making it tamper-resistant.

Figure 22A:
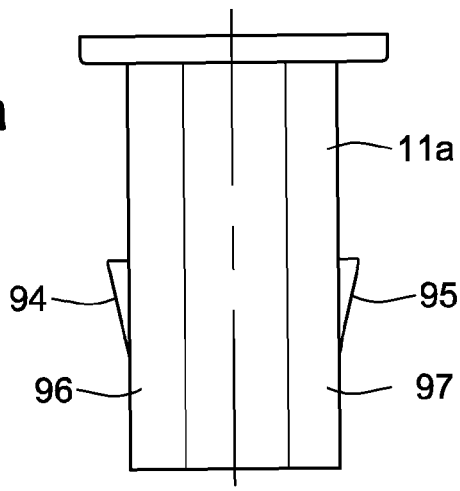
FIGS. 22a-22d form an exploded side elevation of the proximal portion of a modified safety syringe, with FIG. 22c showing a vertical section of the same barrel end portion shown in FIG. 22d but rotated 90° (around the longitudinal axis of the barrel) from the position shown in FIG. 22d.
Figure 22B:
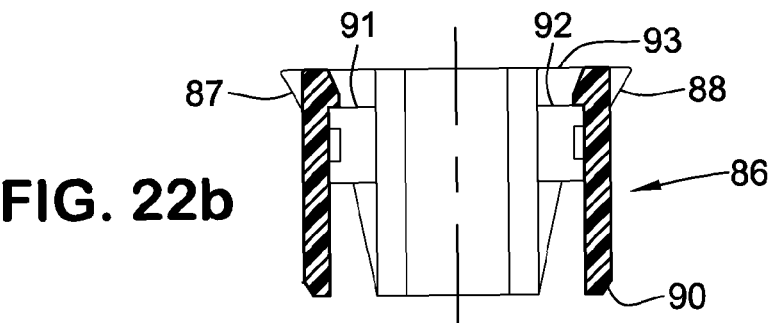
Figure 22C:
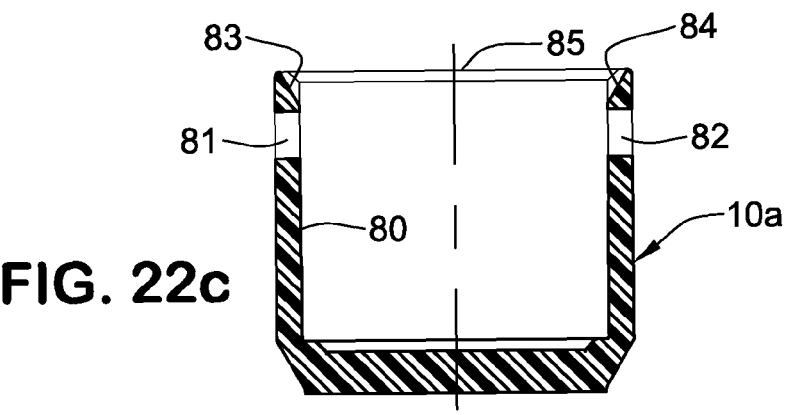
Figure 22D:
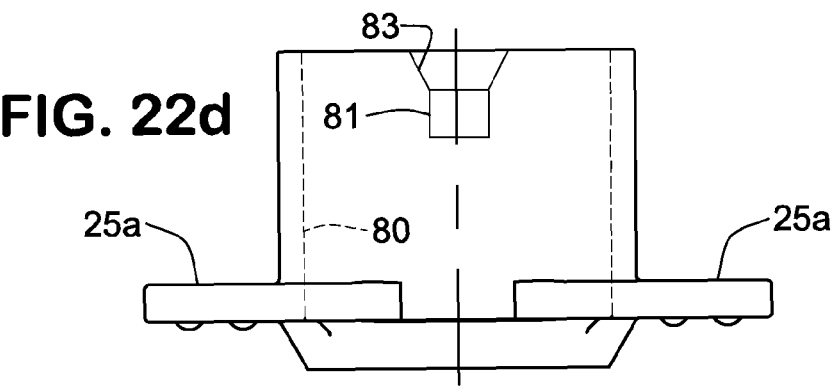
Figure 23:
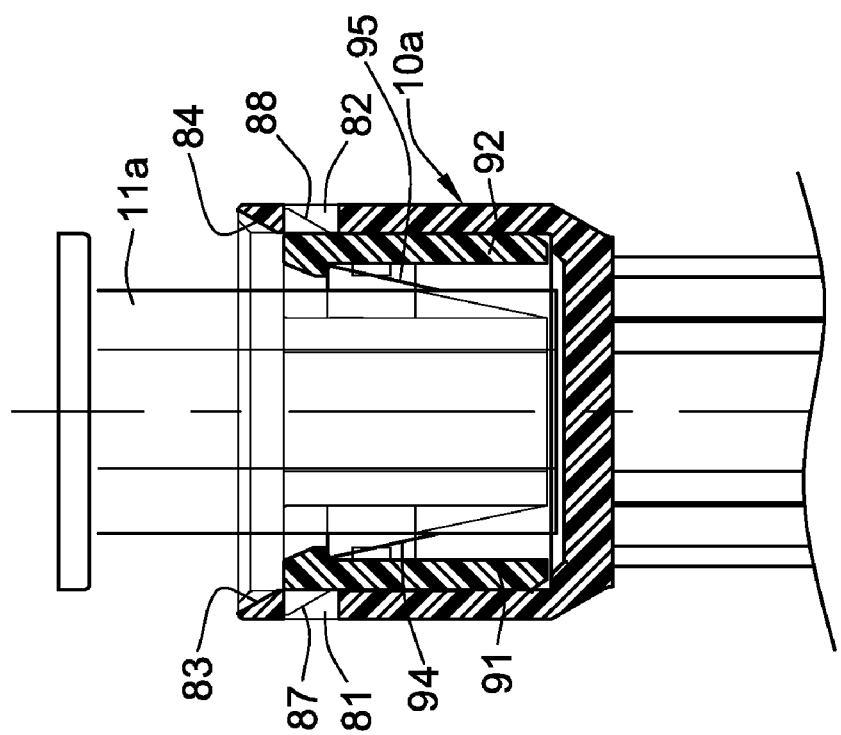
FIGS. 23 is the same side elevation shown in FIGS. 22a-22c, but with the parts assembled.
Figure 28:
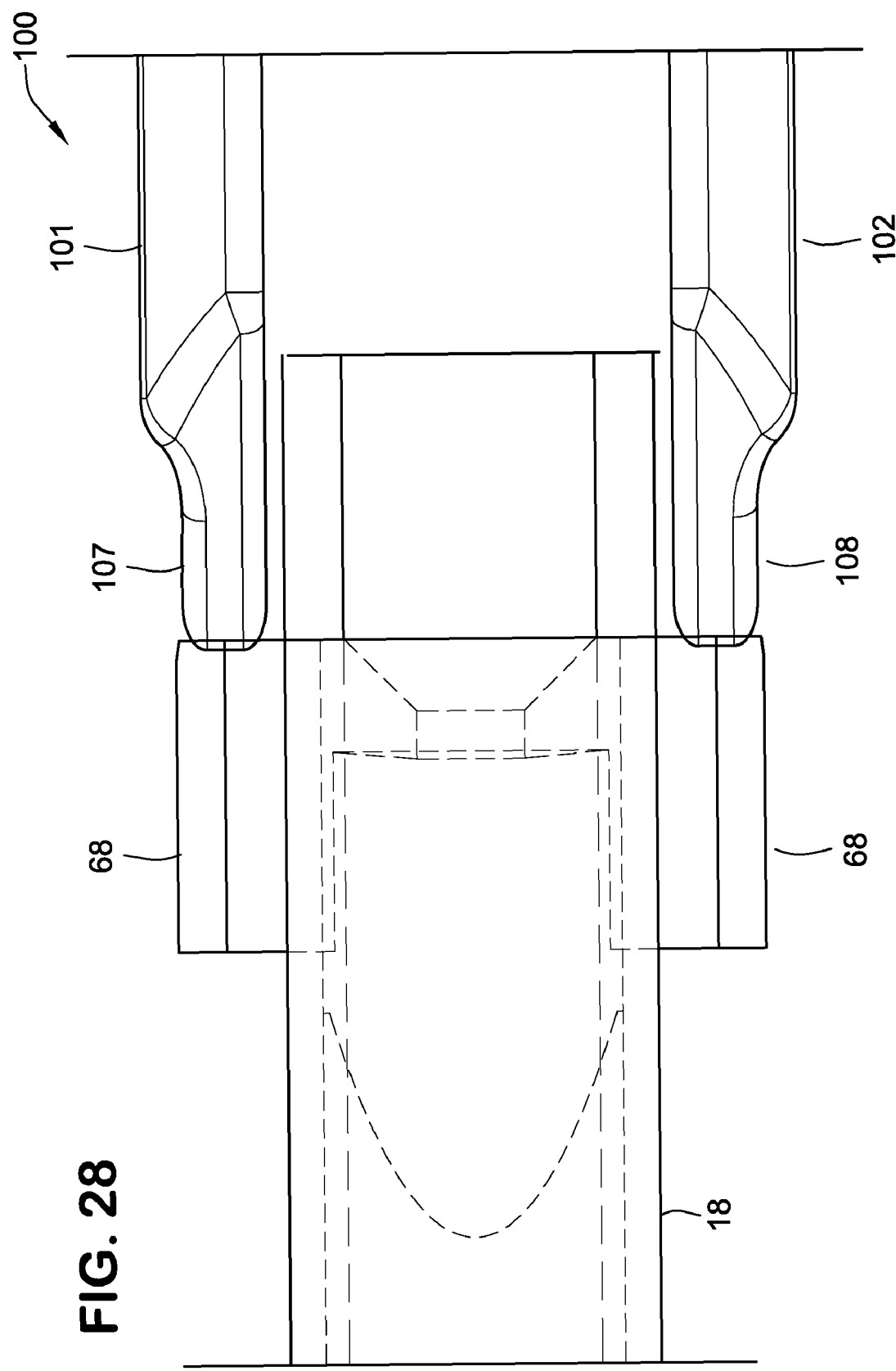
FIG. 28 is an enlarged side elevation of a portion of the assembly shown in FIG. 28, showing the distal end portion of the manual switch and the adjacent portions of the syringe.

FIGS. 22c and 23 show an alternate embodiment, namely a modified barrel 10a having an expanded proximal end portion 80, beyond the flanges 25a, forming a pair of diametrically opposed square locking windows 81, 82 located near the proximal end of the barrel 10a. The illustrative windows 81, 82 are located 90 degrees away from the centerline of the flanges 25a, but can be molded in the same angular position as the flanges 25a if desired. A pair of tapered entry tracks 83, 84 lead into the windows 81, 82 from the proximal end of the barrel 10a and facilitate assembly with an alternative spring retainer 86, shown, for example, in FIG. 22b. A rotated view of the barrel end portion in FIG. 22b shows the windows 81, 82 aligned for assembly with triangular locking projections 87, 88 molded on the proximal end of the semicircular spring retainer 86, which has a chamfered distal end 90. The locking projections 87, 88 are inserted into the entry tracks 83, 84, and the force of the insertion distorts the barrel wall to permit the entry of the projections 87, 88 into the windows 81, 82, as shown in FIG. 23. The rigidity and presence of the modified plunger 11a, illustrated in FIG. 22a, inside the spring retainer 86 firmly locks the spring retainer 86 to the barrel 10a.

The spring retainer 86 of FIG. 22b also has two triangular locking pockets 91, 92 molded inside the body under a rigid margin 93. When the syringe is used to inject medicine and the end point of injection (contact of the plunger cap 12 with the distal wall 23 of the barrel) is imminent, a pair of locking projections 94, 95 on the outer surfaces of the plunger ribs 96, 97 move into the two locking pockets 91, 92 and under the margin 93, as depicted in FIG. 23. The plunger ribs 96, 97 deflect toward each other as the locking projections 94, 95 pass the margin 93, and then return to their normal shapes as the projections 94, 95 snap under the shoulder on the distal edge of the margin 93. The locking projections 94, 95 preferably overlap the distal end surface of the margin 93 by more than 0.025" for tamper-proof engagement.

FIG. 23 shows the locks formed by both pairs of locking projections 87, 88 and 94, 95 when the modified barrel 10a, the spring retainer 86, and the modified plunger 11a are fully assembled, with the plunger 11a in its fully advanced position.

Figure 24:
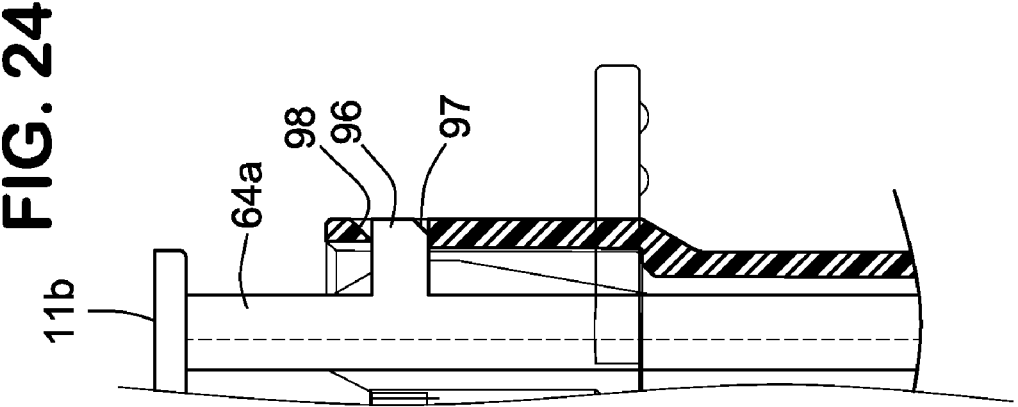
FIG. 24 is a partial side elevation of part of the proximal portion of another modified safety syringe, with the barrel shown in section.

In another alternate barrel-plunger locking arrangement shown in FIG. 24, a circular or square post 96 with a tapered leading edge 97 molded on the back rib 64a of a plunger 11b enters into a window 98, which is similar to the window 81 of FIG. 23, to produce a permanent lock between the plunger 11b and the barrel.

The universal self-operating safety syringe described above is provided sterile and ready to use with instructions to "draw the medicine first," which is preferably printed on the syringe itself. This syringe is passive, totally automatic and is not under control of the user for safety. It is important that the operating features of the syringe are not prematurely or accidentally disabled. Thus several safeguards are preferably provided to avoid premature retraction of the needle and disablement of the syringe. Such safeguards may include, singularly, collectively, or in any combination:

1. The syringe is packaged sterile, with the plunger partially retracted, as is conventional with all syringes. This is a safe location to avoid premature retraction and is achieved by the syringe design. The plunger locking projection 70 overlaps the proximal end surface of the barrel locking sleeve 27, and thus does not permit unintentional plunger advance, as can be seen in FIG. 2. The locking projection 70 contacts the end of the sleeve 27 well before the plunger cap 12 has approached close to the barrel end.
2. The needle cap 15 is taper-locked to the barrel nozzle and maintains a quantum of air inside the barrel. This volume of air prevents advancing movement of the plunger to the activation point that initiates automatic retraction of the needle. A user cannot advance the plunger to the point of automatic needle retraction despite pressing the plunger, because of the locked air. When the user is ready to inject medicine, the user removes the needle cap and is aware of the lock and avoids premature retraction by drawing the medicine first.
3. Drawing the medicine first assures that there will always be some fluid in the barrel, thus preventing advancement of the plunger to the trigger point, until the user completes the injection. This is effective practice, and the users are trained to use the "draw medicine first" procedure.

During normal use of the needle-syringe assembly, the barrel 10 and the needle holder 14 are held generally stationary, and the plunger 11 is free to move axially relative to both the barrel 10 and the needle holder 14. Advancing movement of the plunger 11 is limited by contact of the plunger cap 12 with the end wall of the barrel 10.

As fluid is drawn into the syringe, the user fills the syringe to a desired capacity, emptying air and making volume adjustments. The plunger 11 can never be completely pulled out of the barrel, which is a safety feature that prevents inadvertent spilling of fluid. Withdrawal of the plunger 11 is limited by contact of the spring retainer 18 with the interior of the rubber cap 12 on the plunger, as depicted in FIG. 3.

The tabs 25 on the proximal end of the barrel 10 permit the user to pull the plunger 11 with a single hand to draw medicine, and to push the plunger with a single hand to inject the medicine. The medicine is then injected into the patient using established protocol.

As the medicine is injected by advancing the plunger 11 longitudinally within the barrel 10, the ramps 47a and 48a on the plunger deflect the wings 68 of the latching segment 66 of the spring retainer 18, thereby pushing the latching projection 64 outwardly. This relieves the compression force on the needle holder head 61, and the spring 17 then retracts the needle fully inside the plunger channel and maintains the needle in that position. At the same time, the barrel 10 and the plunger 11 interlock, thus disabling the syringe. This action is instantaneous. The automatic interlock is not under control of the use, and there are no mechanisms to override it.

Manual Switches

There are numerous situations in clinical use of syringes where the entire contents of the syringe barrel cannot and need not be emptied and the retraction trigger mechanism is therefore not activated. Nonetheless, for the safety of the healthcare workers, the needles of the used syringes must be retracted, and the syringes must be disabled to prevent their re-use. These objectives are achieved by an optional add-on safety mechanism in the form of a manual switch which operates on demand, i.e., voluntary actuation by the healthcare workers performing the procedures or administering special medications.

One embodiment of a manual switch 100 for the universal syringe described above is shown in FIGS. 25-29, and consists of two elongated parallel plates 101 and 102 (FIG. 25) joined in the center by a bridge 103 (FIG. 26) for stability. At the proximal end, the two plates 101 and 102 are joined together by an actuator plate 104 at 90 degrees to the long axis of the plates 101 and 102. A push on the actuator plate 104 enables the user to advance the switch 100 inside the barrel 10. The switch is engaged in slots 105 and 106 in the plunger ribs 47 and 48 that form the central channel 46 (see FIGS. 15 and 16). The plates 101 and 102 are machined or molded to the size of the available space and, in the illustrated embodiment, are generally square in cross section. The distal ends 107 and 108 of the plates 101 and 102 have generally triangular shapes, and are located in close proximity with the proximal edges of the wings 68 of the latching segment 66 of the spring retainer 18. When the switch 100 is advanced, the triangular portions 107 and 108 advance under the wings 68 and lift them to release the needle holder head 61, causing retraction of the needle holder 14 and, thus, the needle 13.

A pair of convex detents 109, shown in FIG. 26, prevents inadvertent advancing movement of the switch 100, and consequent premature retraction of the needle 13. The inside surface of the manual switch 100 also has two triangular detents 110 below the convex detents 109. When the switch 100 is advanced inside the barrel 10, the triangular detents 110 engage the underside of the latching segment 66 to lock the switch 100 to the spring retainer 18, and thus to the barrel 10 so that the manual switch 100 cannot be retracted. The retraction of the needle 13 and disablement of the syringe is permanent and beyond the vision and control of the user. In one arrangement, the activator plate 104 is located in a space between the proximal end of the barrel 10 and the thumb plate 30 of the modified plunger 11b.

As the switch 100 is advanced, the parallel plates 101 and 102 enter the barrel 10 and are located on either side of the latching segment 66 of the spring retainer 18. The bridge 103 is concave and rides over the tubular spring retainer 18.

As seen in FIG. 27, the switch 100 is securely located within the barrel 10 and slides along opposite sides of the cantilever 62. It remains there without interfering with any of the syringe functions and permits free linear movements of the plunger during normal operation of the syringe, e.g., to withdraw and inject medicine.

The syringe with the manual switch 100 is provided ready to use with the needle 13 extending out through the nozzle 23. Since this syringe is manually controlled, the operator can use the syringe in exactly the same way as a conventional syringe, and can stop the use of the syringe at any position to control the volume of fluid injected. Once the user decides that the procedure is completed or the syringe does not need to be used any further, the user simply advances the actuator plate 104, which lifts the wings 68 to release the needle holder head 61, allowing the spring 17 to expand and retract the needle holder 14, and thus the needle 13, inside the plunger channel 46.

The plunger 11 may be modified by removing the ramps 47a, 48a that trigger automatic retraction of the needle 13, to avoid duplicate trigger mechanisms for releasing the spring latch. The switch 100 is preferably installed during assembly of the syringe and, thus, may become an inseparable, integral part of the syringe.

The present invention is not limited to the injection of medicine, as injection of medicine into a patient is just one of many applications of the syringe. Other procedures, such as, but certainly not limited to, intravenous placement of catheters, aspirating blood or body fluids, or controlling infusions, require skillful control and judgment over the advance of the plunger. This supercedes the automated function of the syringes described above. Thus, the syringes may be provided with manual control switches, as described above, to actuate the retraction. The manual switch is accessible at the barrel margin for operation, and just a push of the switch instantly retracts the needle. The syringe is preferably emptied of its contents before the retraction is initiated.

A number of regulatory bodies require or recommend that in safety syringe devices, the switch be inseparable from the syringe. In general, these requirements or recommendations state that the functional attachments of a medical device that alter the functions of the device, such as clamps, switches etc., should be inseparable from the device. These switches or other attachments must move and work, but they should not be removable. Thus, the manual switch as well as the barrel where the switch is installed are preferably designed to comply with these medical device standards and regulations. Since the manual switch is located inside the syringe, there is no question of its separation from the device and therefore the syringe complies with regulatory requirements and/or recommendations. Those skilled in the art may devise other specific switch constructions for accomplishing their goals without departing from the invention.

Syringe Length Optimization

Besides being needle-stick-infection free, and non-reusable, the syringes described above serve as permanent sharp containers for their own retracted needles. This may require a slightly increased length, even though space economy has been optimized. The extra plunger/barrel length accommodates the user's fingers in the space between the plunger knob and the finger flanges. The extended barrel length is used to lock and store the retracted needle holder and the entire needle.

The compression spring 17 is designed to guarantee full retraction of the hypodermic needle 13 and the needle holder 14 as well as subsequent maintenance of the needle holder 14 in the retracted state. The syringe components are totally interlocked and inoperative.

Since retraction of the needle 13 is effected by the spring 17 or other elastic biasing means, upon releasing the latch, the hand of a user does not come into the vicinity of the needle point, thereby minimizing the possibility of a needle prick during retraction.

The number of components in the illustrative syringe is not significantly different from a conventional syringe, to keep it cost effective.

The operation of the syringe is one-way so that accidental misuse is minimized, i.e., once retracted the needle holder is locked in place, so the needle cannot be re-extended.

Operation of the syringe is particularly safe because all the required manipulations of the various parts of the syringe are performed at or near the proximal end of the syringe, well away of the needle, during both the normal and retracting modes of operation.

The needle-syringe assembly is easy to manufacture, cost effective, and easy to use in the field. In general, the parts can all be made by conventional plastic molding, using readily available medical grade stainless steel needles and compression springs. The plastic parts can be made by injection molding of medical grade, gamma stable polymers such as polypropylene. The needle holder and spring retainer that require higher strength can be molded from polycarbonate. The plunger cap 12 and the O-ring 16 can be molded from non-latex, synthetic elastomers or silicones. The switches that require smooth, friction-free movements can be made from HDPE. Of course, the material selection is guided by the strength and functional requirements of the components. The materials mentioned above can be substituted by alternate or improved compounds that may or may not be presently available. The needle may be boned to the needle holder by using ultraviolet-curable adhesives. The syringes can be assembled and packaged in a clean room and sterilized by gamma radiation.

Assembly Technology

Conventional syringes have isometric parts that do not require any orientation and simply fit one into another, e.g., the plunger fits into the rubber piston and the rubber piston into the barrel. In one possible approach, once the parts are oriented by either rotary or vibratory feeders, they are pressed into one another by turrets of continuous motion rotary machines. The entire assembly process is vertical, and the parts (barrel, rubber piston, and plunger) are aligned on a single axis.

Single-use retractable needle syringes are precision devices with special demanding functions that requite complex parts for operation, and need lateral orientation for assembly.

FIGS. 30a-30i depict an exemplary assembly sequence for assembling the retractable-needle, single-use and auto-disable syringe described above. It should be understood that manufacture and fabrication of the present invention is not limited to the methodology disclosed hereinbelow, which is provided in one representative embodiment purely for explanatory purposes. As such, other methods and means of manufacture are certainly envisaged within the scope and spirit of the present invention.

A bulk loader feeds a first feeder bowl with barrels and a second feeder bowl with O-rings, then pressing start on the touch screen initiates the assembly operations. Four barrels are bowl fed and loaded into four nests on a dial. The barrels are indexed to a print station where a pad printer prints the scale on one side. The barrels are indexed under a UV curing station to dry the ink. Four lanes of O-rings are fed and installed into the barrel. The parts are indexed to a "Spraymation" (or equivalent) silicone station where silicone is uniformly jet-sprayed into the vertical barrel, and then the parts are offloaded to a plunger sub-assembly syringe assembly machine.

A stable plunger block with matching plunger geometry is securely screwed to a small station platform under two pneumatically controlled clamps on each station. Each block contains precision tracks to receive a barrel block for engagement with a plunger sub-assembly The plungers 11 are bowl fed in four lanes toward the dial with the thumb plate 30 leading. Four rubber plunger caps 12 are bowl fed, oriented, and placed on the ends of the plungers 11. Four spring retainers 18 are placed in the four plunger channels 46 and pushed forward. Four processed barrels 10 are picked up and pushed onto the plunger assembly to a set depth, and then the locking cantilever 62 of each spring retainer 18 is pushed into the locking pocket 26 of the corresponding barrel 10. The spring feeder then feeds four springs 17 through assembly holes 200 of the four plungers 11 and advances them into the spring retainers 18. Four needle holders 14 are picked up and fed through assembly holes 200 in the plungers 11 and loaded into the spring retainers 18. The arming station presses the needle holders 14 forward to extend through the barrel nozzles 23. A one-way plug 202 is inserted to close each assembly hole 200. A needle 13 is then bonded to each needle holder 14, and the barrels 10 are capped with the needle protector caps 15. All assembly operations are verified with sensors at each station. If three bad parts in a row are produced, the machine stops and alerts an operator to fix the problem. Operations stop on any piece if an error is found. The sub-assemblies index under a visual inspection station to ensure proper assembly.

Figure 30D:
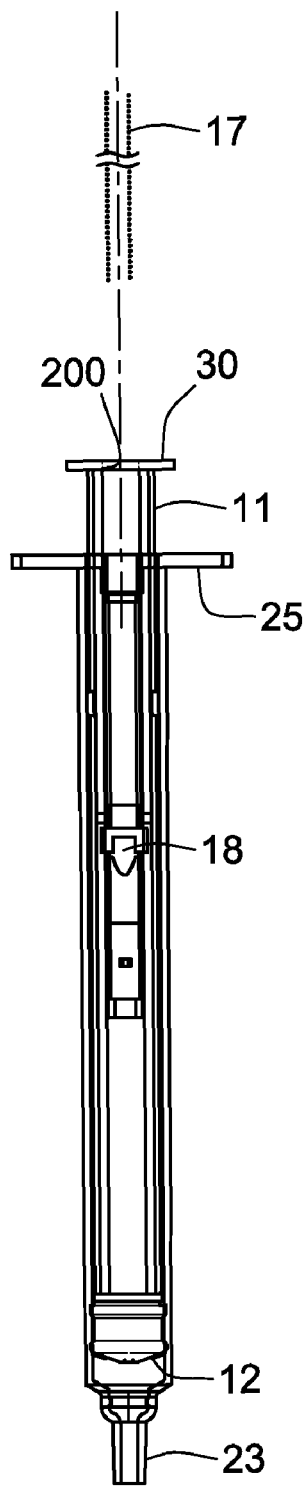
Figure 30E:
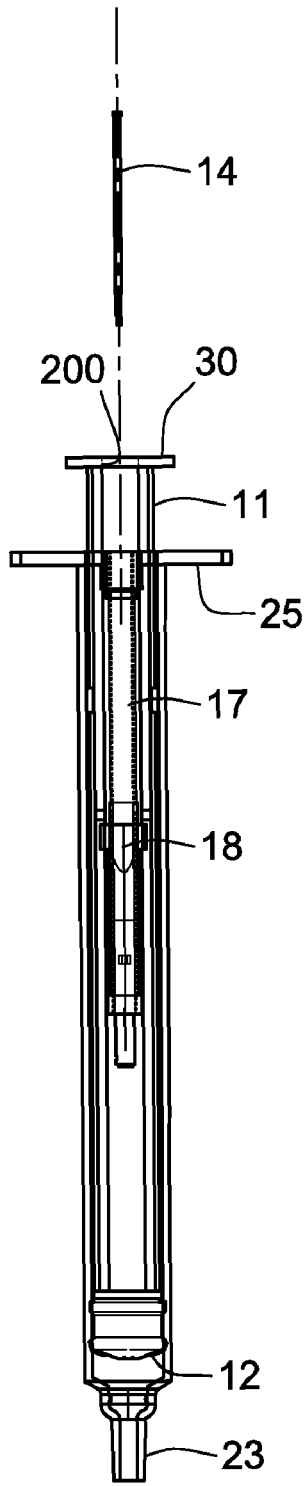
Figure 30F:
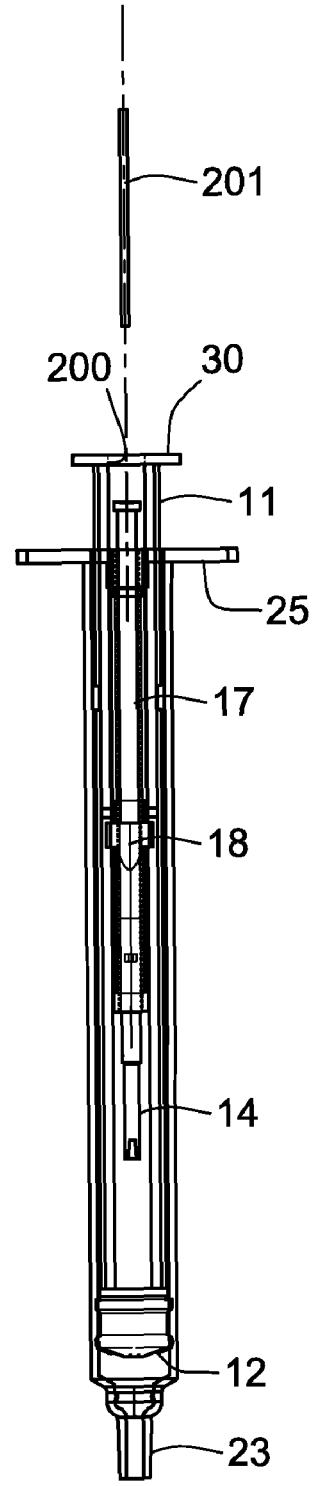
Figure 30G:
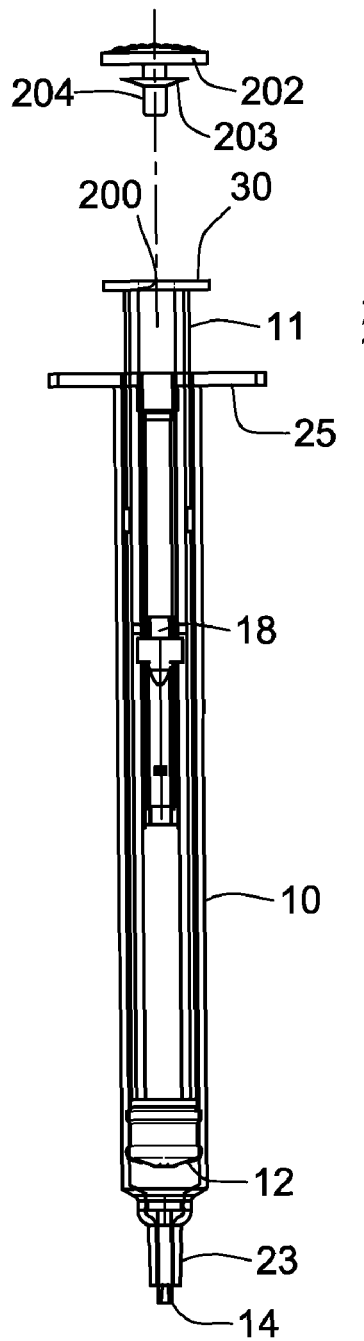
Figure 30H:
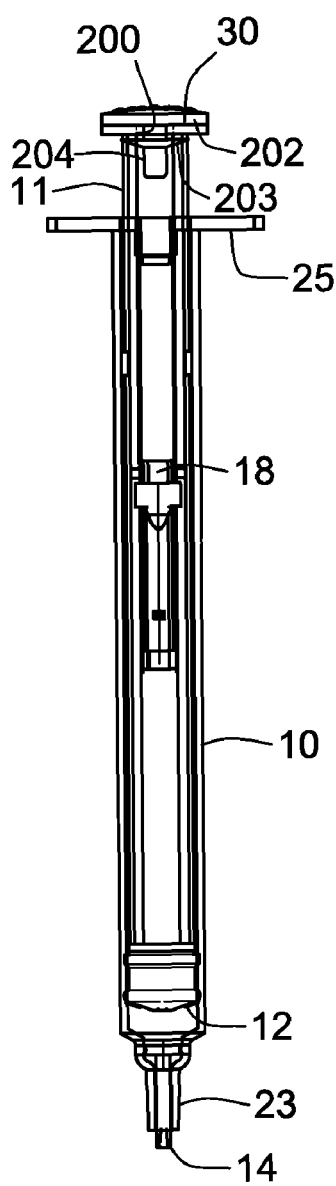
Figure 30I:
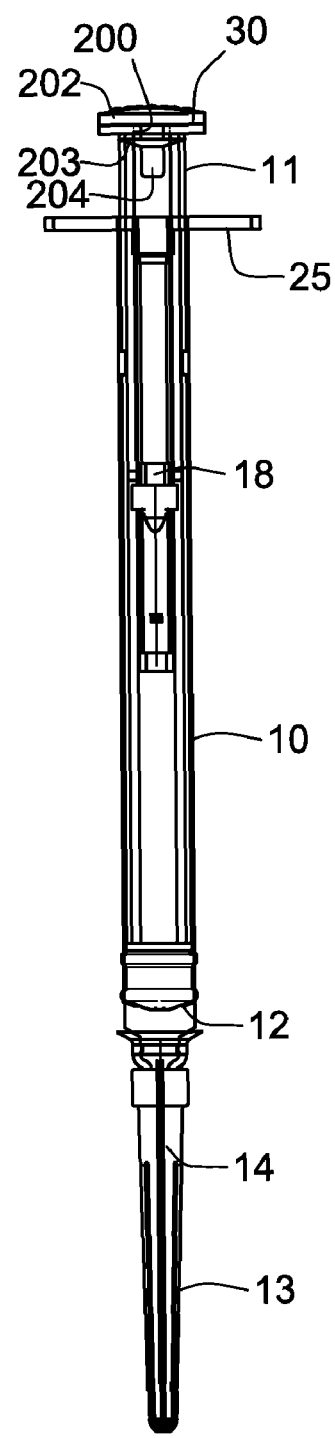

Referring to FIG. 30g, the proximal end of each spring retainer 18 is open to allow sequential feeding of the spring 17 and the needle holder 14 during assembly of the needle retractor unit through the assembly hole 200, which is then closed by the plug 202. Once fed inside the spring retainer 18, the spring 17 and the needle holder 14 can only move axially and can project out of the spring retainer 18 when retracted but still remain in the central channel 46 of the plunger 11.

The thumb plate 30 is provided with a central hole 200 to permit feeding the spring 17 and needle holder 14, in that sequence, into the spring retainer 18 during assembly. The hole 200 is also used to arm and advance the needle holder 14 distally through the O-ring 16 and the barrel nozzle 23, as depicted in FIGS. 2 and 3. When an assembly tool 201 (FIG. 30f) is inserted through the hole 200, the tool 201 advances the needle holder 14 longitudinally, compressing the spring 17, until the needle holder 14 is locked in its advanced position in the nozzle 23 of the barrel (see FIG. 2). Once the assembly of the integral retracting assembly is completed and the syringe is armed, the plunger hole 200 is closed by a plug 202, as shown in FIG. 15. A retaining ring 203, formed as an integral part of the stem 204 of the plug 202, snaps under the distal surface of the thumb plate 30 to lock the plug 202 in place on the plunger 11.

Recycling

Figure 31:
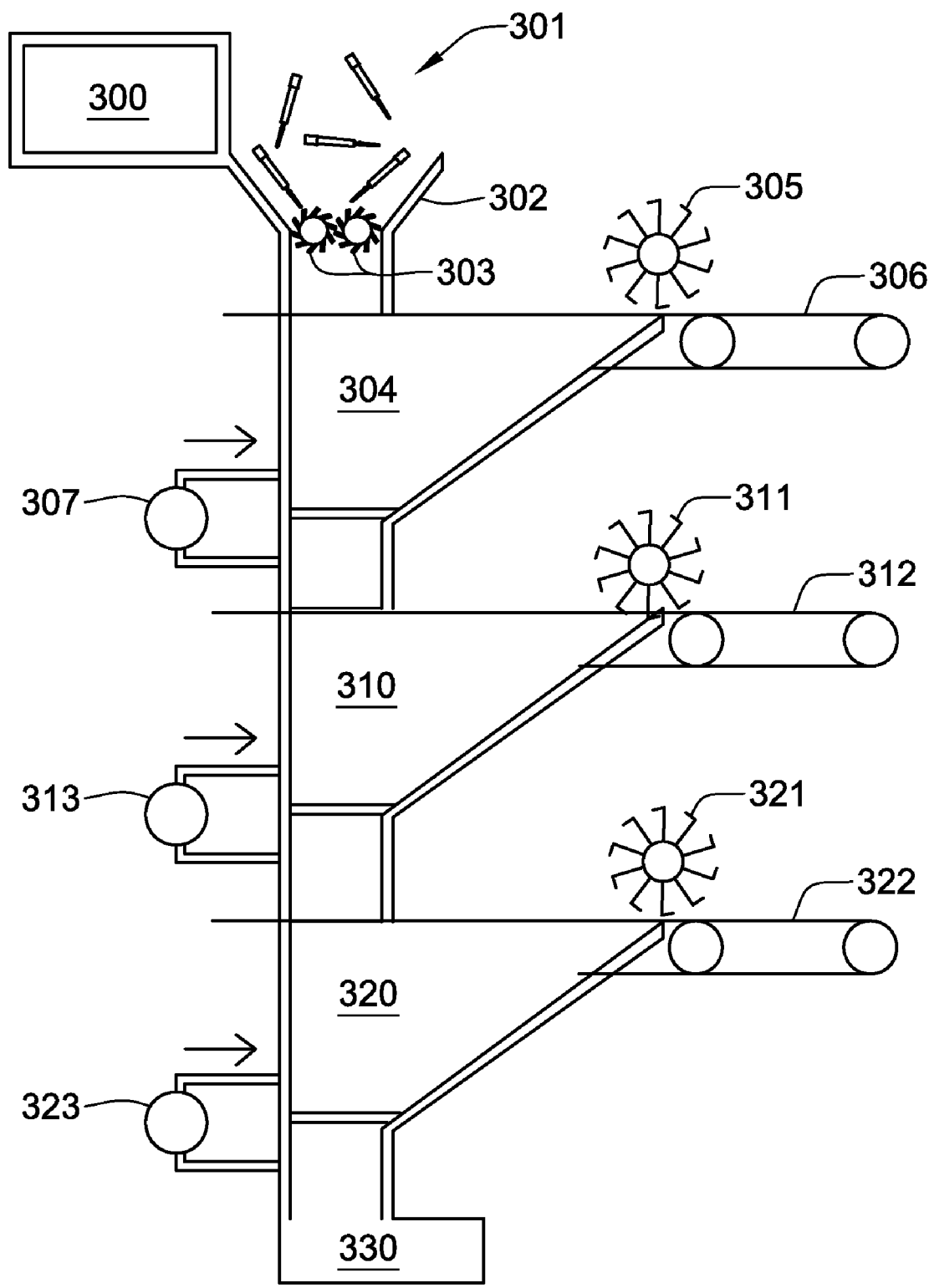
FIGS. 31 is a diagrammatic illustration of a process of recycling syringe of the type shown in FIGS. 1-4.
Figure 32A:
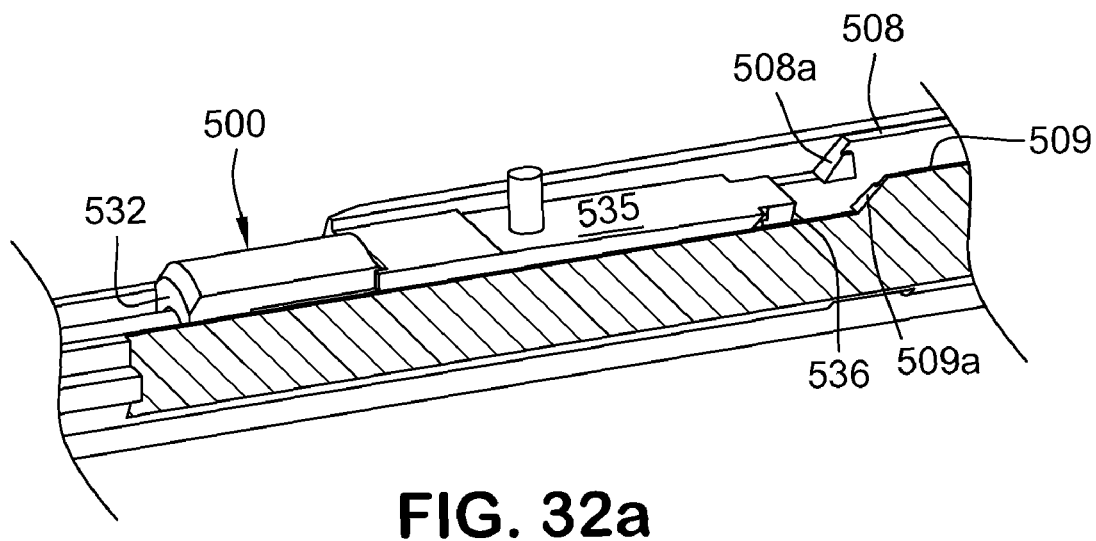
FIGS. 32a and 32b are perspective views of a portion of a modified plunger and spring retainer with the plunger in two different positions and with a portion of the plunger shown in longitudinal section.
Figure 32B:
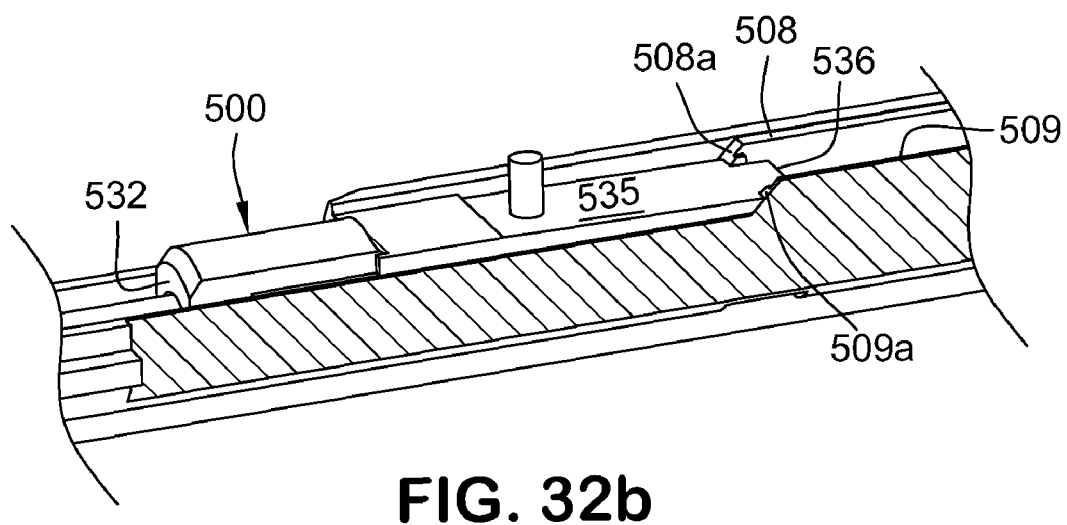

Syringes, though used as disposable devices, are not easily disposable, because they are made from durable plastics. Besides polluting the environment, these materials will be expensive due to escalating cost of the oils and petrochemicals derived from them. The syringes therefore must be recycled and the plastics retrieved and re-used both for economy as well as environmental impact. FIG. 31 illustrates a method of recycling syringes to recover the plastics for future applications. Each syringe is typically composed of three plastic polymers and stainless steel. For example, the barrel 10, the plunger 11 and needle protector cap 15 may be made of polypropylene; the plunger cap 12 may be made of synthetic rubber, neoprene or isoprene; the retraction control unit and the needle holder 14 may be made from polycarbonate; and the spring 17 and the needle 13 may be made of stainless steel. A simple, non-energy-consuming, economic recycling method can be used to separate these materials in pure form for reuse in different applications. The process is cost-effective because syringes contribute 17% of the plastic waste generated from hospitals. The recycling steps are shown in FIG. 31.

Step 1—Polypropylene Recovery

The used, contaminated syringes are collected in red bags as required for biological hospital waste. With due precaution, the containers pass through a pressurized steam sterilization chamber 300 to sterilize them. The sterile syringes 301 are then bulk fed into a hopper 302, and water-cooled cutting wheels 303 cut the syringes into fragments that pass into a first water-filled tank 304. Here all the fragments of polypropylene (polypropylene having a specific gravity of 0.9) float to the surface of the water, which has a specific gravity of 1.0, while the fragments of other materials sink because of their higher specific gravities. A bladed wheel 305 may be provided that skims the floating fragments from the tank 304 onto a conveyor 306. The water in the tank 304 is continually re-claimed by a pump 307.

Step 2—Polycarbonate Recovery

The sunken fragments of polycarbonate, which has a specific gravity of 1.20, along with the neoprene and steel fragments, pass to a second tank 310 filled with glycerol, which has a specific gravity of 1.26. The polycarbonate fragments float on the surface of the glycerol in tank 310, while the fragments of other materials sink because of their higher specific gravities. A bladed wheel 311 may be provided that skims the floating fragments from the tank 310 onto a conveyor 312. The glycerol in the tank 310 is continually re-claimed by a pump 313.

Step 3—Synthetic Rubber Recovery.

The plunger-cap fragments are typically made from neoprene or butyl isoprene, which have variable specific gravities, pass into a tank 320 containing a solvent having a specific gravity greater than that of neoprene or butyl isoprene. Such solvents are commonly used in the rubber industry. The fragments float on the surface of the solvent in the tank 320, while the remaining fragments of steel sink because of their higher specific gravity. A bladed wheel 321 may be provided that skims the floating fragments from the tank 320 onto a conveyor 322. The solvent in the tank 3230 is continually re-claimed by a pump 323.

Step 4—Stainless Steel Recovery

The final fragments of stainless steel sink to the bottom of the tank 320 and pass into a container 330 where they are recovered and melted in a furnace, which also clean burns remaining contaminants such as adhesives.

All the components of the syringe are thus retrieved and used to make other products, by generating profit and avoiding the environmental impact. Consumers benefit from cost reduction.

Since the liquids with differing specific gravities that are used to separate the components are miscible, the tanks are isolated from each other by conventional valves. Mixing of the liquids would alter the specific gravities. The process is especially efficient when the liquids are immiscible with each other.

Additional Embodiments

The functional attributes of the syringe reside in the components that are responsible for the hydraulic function (e.g., the barrel 10, the plunger 11, the rubber stopper 12, the "O" ring 16, etc.), and the needle holder 14 and needle 13 that are responsible for injection. The safety mechanism for retraction of the needle and reuse prevention are additional functions. The retraction depends on the spring retainer 18 that is reversibly engaged with the needle holder 14, which is encircled by a compressed spring 17, urging the needle holder 14 and needle 13 to retract on contact with plunger ramps 47a, 48a when the plunger 11 advances in the barrel 10 and completes the injection. In preferred practice, this chain of events is precisely timed and is not under the control of the user. Re-use of the syringe is also defeated by the re-use prevention mechanism 27, located on the barrel in the form of locking slots and plunger flanges 71 that advance with the syringe function involuntarily. This satisfies the objectives of universal syringes in preventing needle stick injuries and consequent prevention of microbial infections by obligatory retraction of the needle at the completion of the injection of medicine. At the same time reuse of the syringe components by unscrupulous people is prevented by automatic interlock of the syringe components.

A modified embodiment of the spring retainer 18 is illustrated in FIGS. 32-50. In addition to the retraction function, this modified device interlocks the syringe itself. It can be constructed from performance plastics such as polycarbonate (in contrast to the softer polypropylene plastics used for syringe components), which helps to maintain the physical integrity and alignment of all the syringe parts. Its shape maintains the integrity of the barrel circumference. Plunger flanges (also referred to herein as "ribs) are mechanically engaged and kept aligned in the spring retainer geometry, and side flanges/ribs engage in a diametric groove of the spring retainer. All these elements are concentrated in a semicircular anchoring portion of the safety module to make it work as a precision device.

Figure 35:
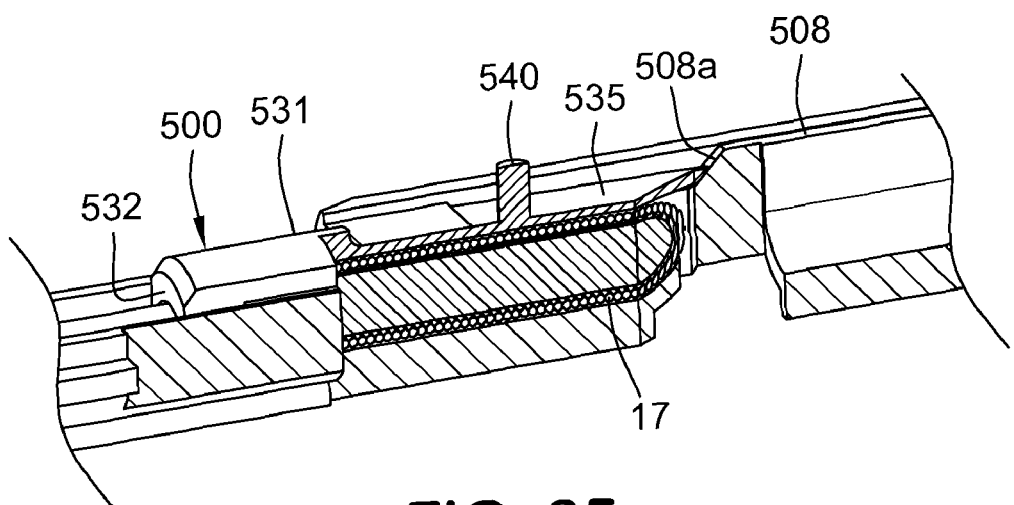
FIG. 35 is the same perspective view shown in FIG. 34 with the spring retainer, needle holder, spring and plunger further sectioned along line 34 in FIG. 33.
Figure 36:
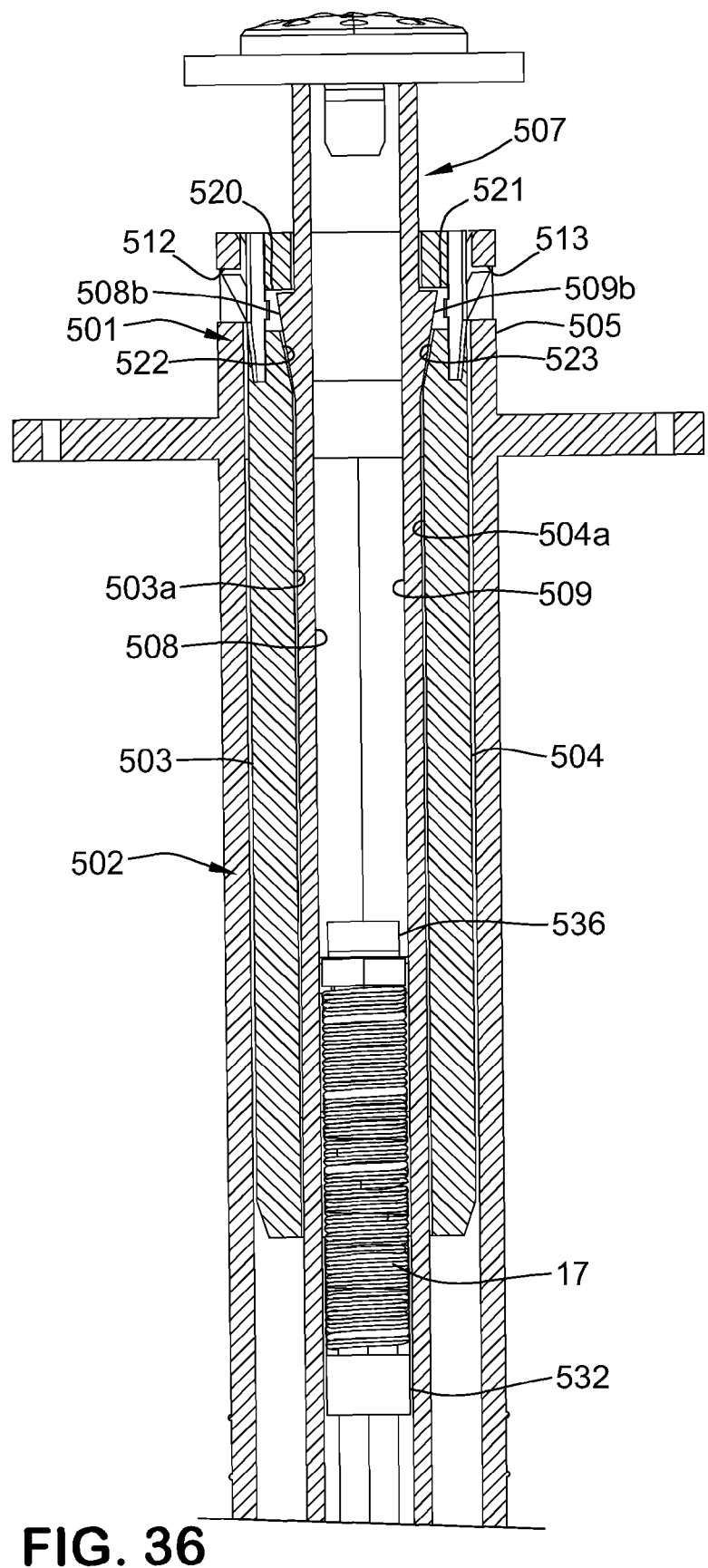
FIG. 36 is a sectional view of the proximal 3 end portion of a syringe using the modified spring retainer and plunger of FIGS. 32-35.
Figure 37:
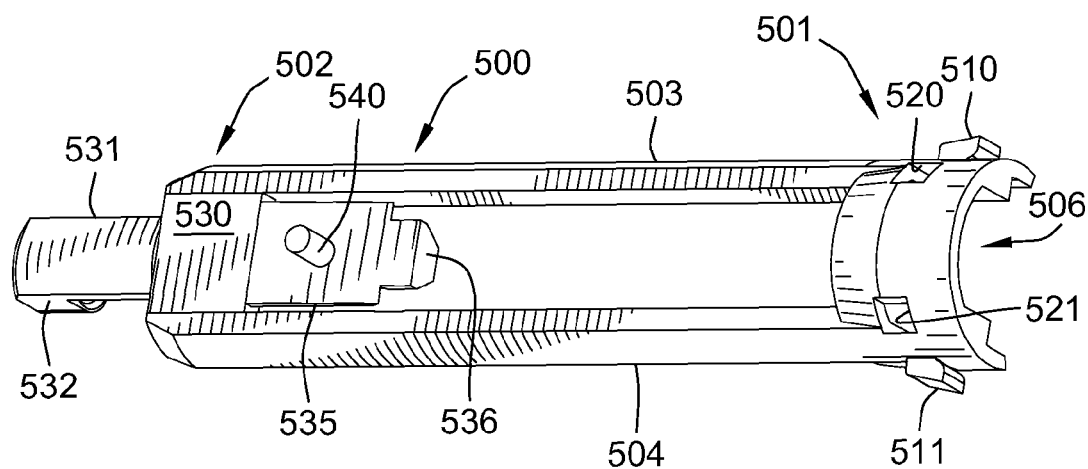
FIG. 37 is a perspective view of the modified spring retainer shown in FIGS. 32-36.

Referring to FIGS. 32-50, but initially to FIG. 37, a safety control module 500 forms a spring retainer that includes a unitary, elongated plastic element having a curved proximal anchoring and locking portion 501 (also referred to herein as "semicircular anchoring plate") in opposing spaced relation to a distal retraction control portion 502 (also referred to herein as "compression plate"). A pair of elongated bars 503 and 504 interconnects the proximal and distal portions 501 and 502. The length of the bars 503 and 504 determines the range of motion for needle retraction, as described in more detail below. As can be seen in FIG. 36, the module 500 is inserted in a barrel 505, with the proximal anchoring portion 501 at the open, proximal end of the barrel 505, and the distal retraction control portion 502 positioned within the interior of the barrel 505.

Figures 38A, 38B, 39:
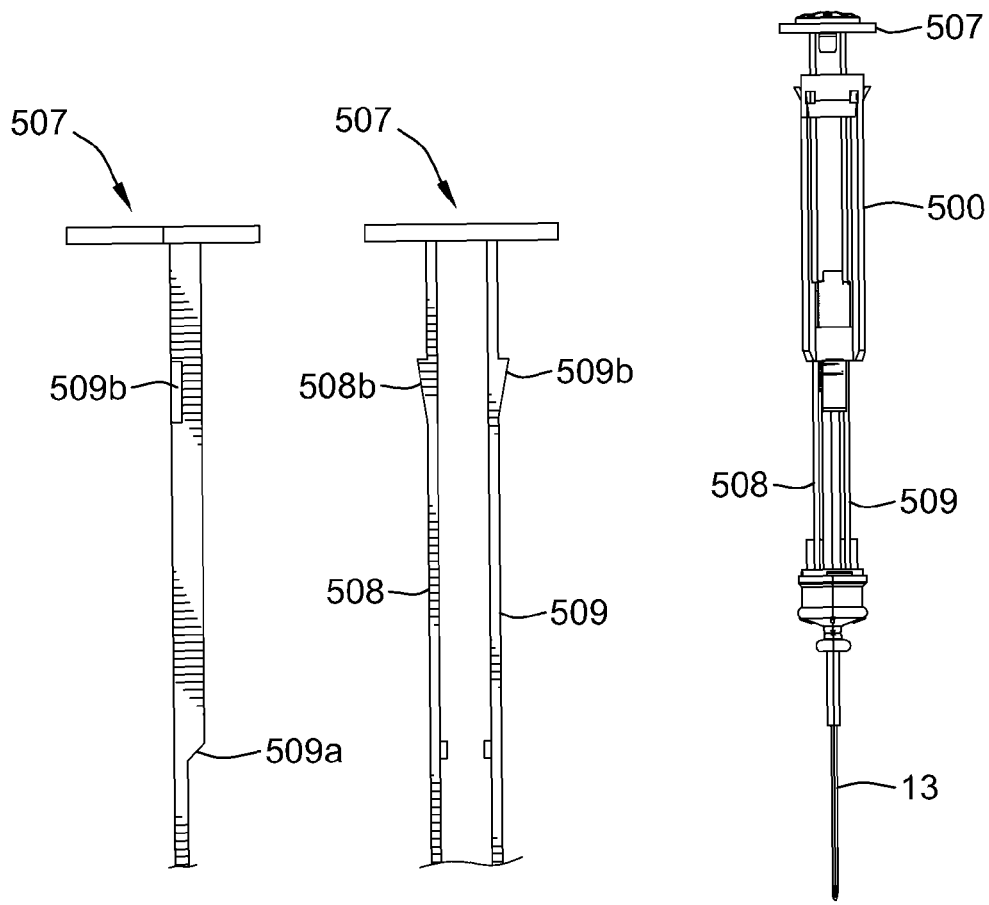
FIGS. 38a and 38b are side elevation and bottom plane views of the proximal end portion of the plunger shown in FIGS. 32-36.
FIG. 39 is a side elevation of an assembly of the plunger, spring retainer and needle holder shown in FIGS. 32-38.
Figure 40:
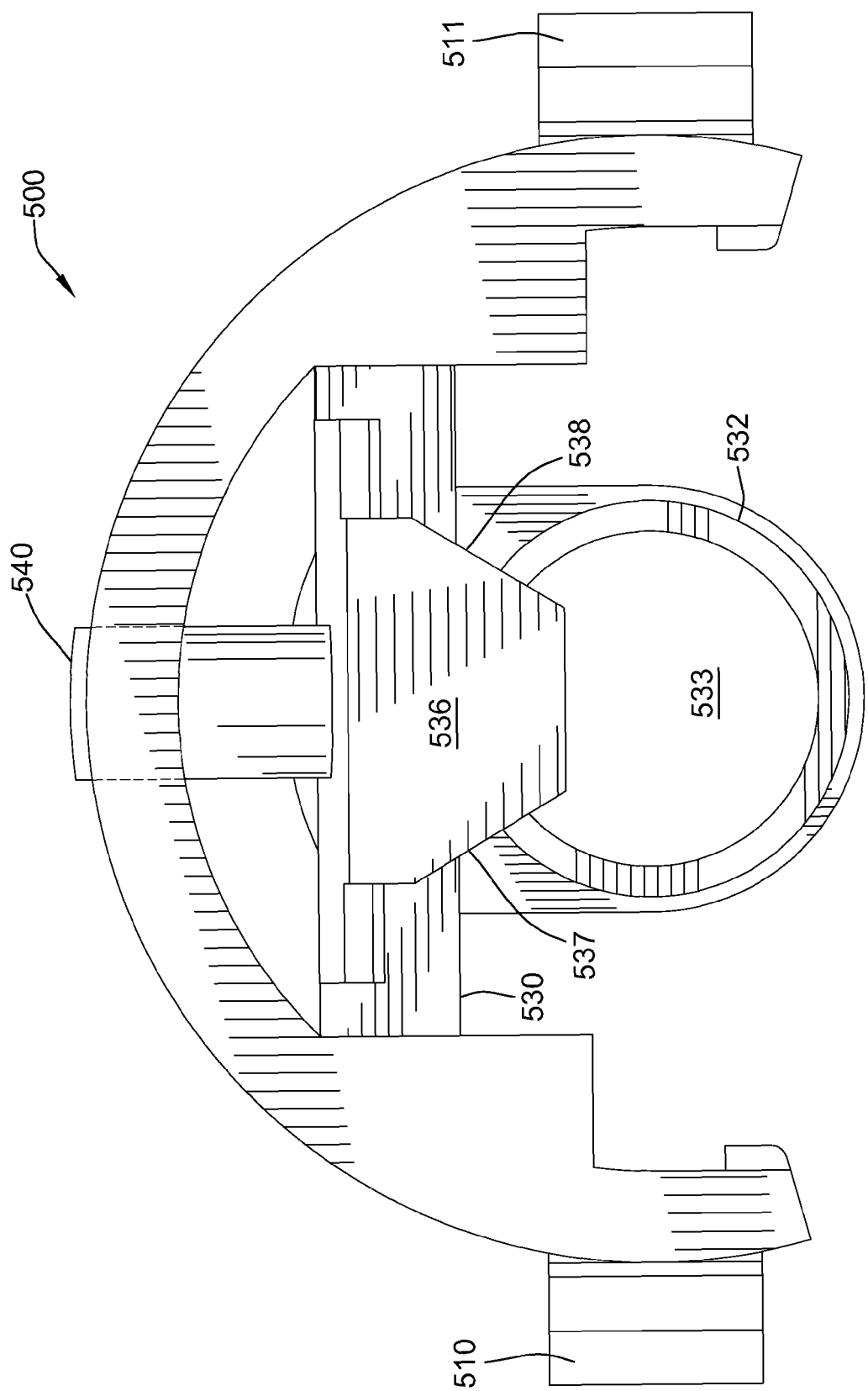
FIG. 40 is an enlarged end elevation of the proximal end of the spring retainer shown in FIG. 37.
Figure 41:
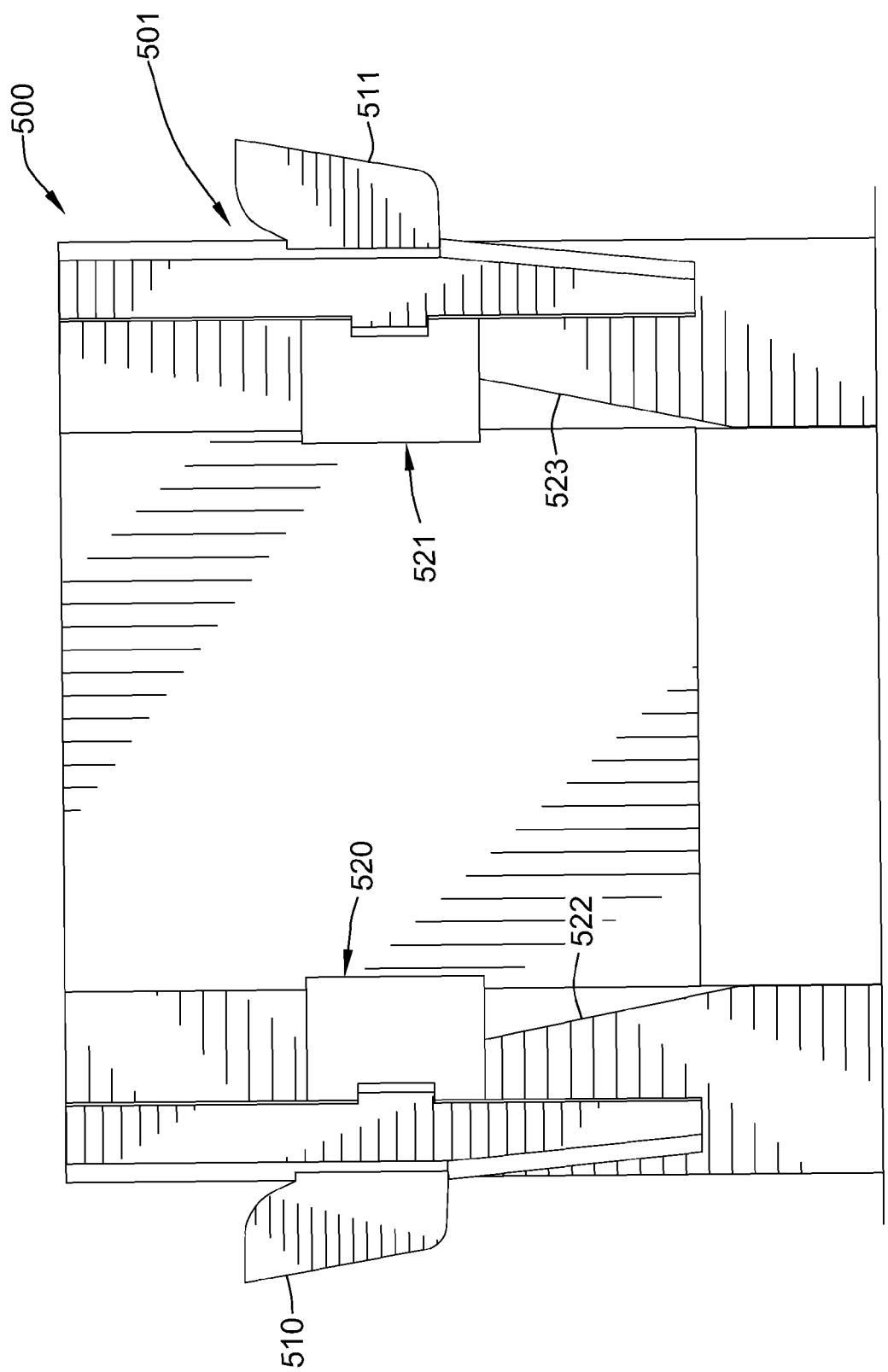
FIG. 41 is an enlarged side elevation of the proximal end portion of the spring retainer shown in FIG. 37.

As can be seen in FIGS. 36-40, the interior of the control module 500 forms a channel 506 (called out in FIG. 37) for receiving a plunger 507. In this embodiment, the plunger 507 forms a pair of elongated ribs 508 and 509 (shown, for example, in FIG. 38b) that extend into the interior of the module 500 along the inside surfaces 503a and 504a of the elongated bars 503 and 504, respectively, as seen in FIG. 39. The barrel 505 is removed and the plunger 507 is partially sectioned in FIG. 39 to show the relationship between the module 500 and the plunger 507. The elongated edges of the plunger ribs 508 and 509 form angular ramps 508a and 509a (FIG. 32b) that are positioned to trigger retraction of the needle (e.g., 13 of FIG. 1) after the plunger has been advanced to complete injection of the medicine. In addition, two additional triangular projections 508b and 509b (best seen in FIG. 38b) on the outer side walls of the ribs 508 and 509 function to latch the plunger 507 to the module 500, as illustrated in FIGS. 36 and 45-47 and described in more detail below. In this embodiment, during normal operation, the plunger 507 is preferably the only moving element of the syringe and is maintained in constant contact with the module 500.

Figure 45:
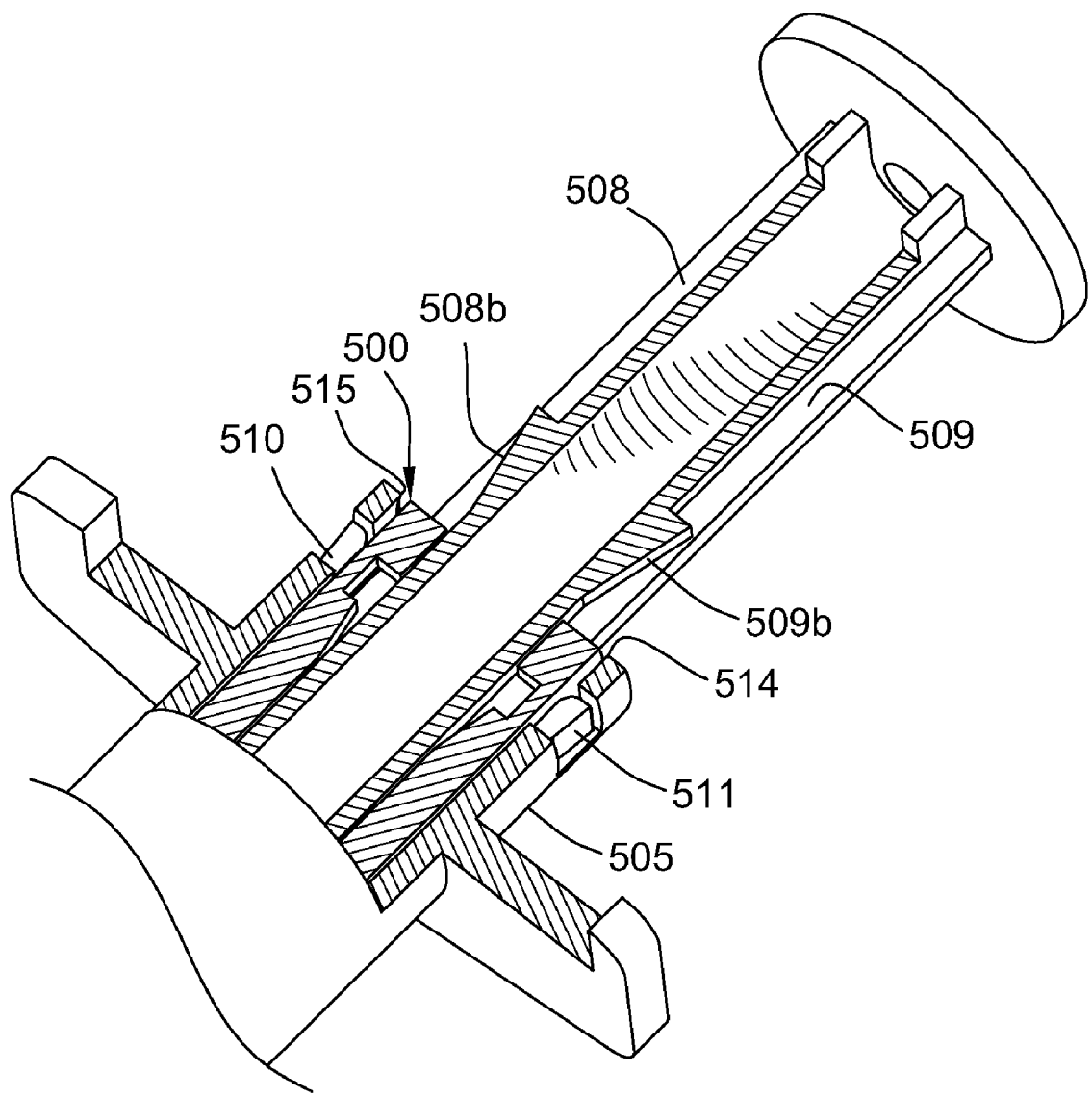
FIG. 45 is a perspective view of the proximal end portion of the syringe shown in FIG. 36 with the plunger only partially installed and with only a proximal end portion of the assembly shown in section.
Figure 46:
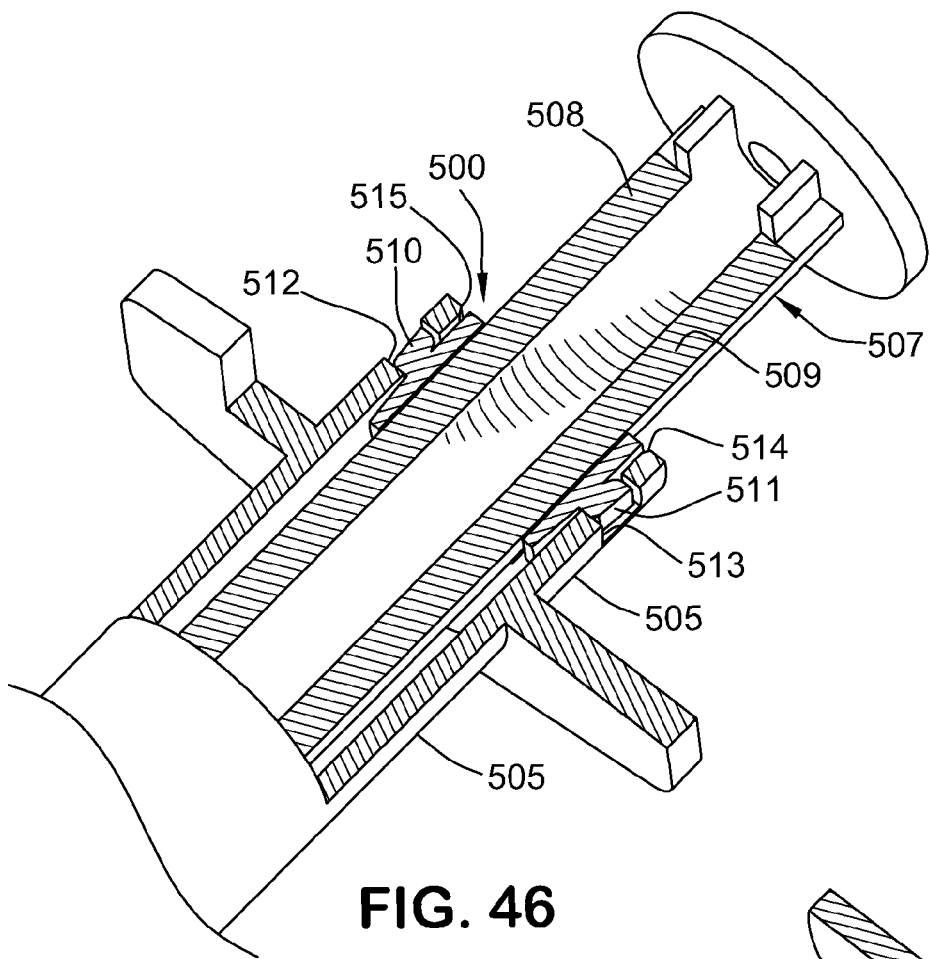
FIG. 46 is a perspective view of the proximal end portion of the syringe shown in FIG. 45 with the plunger installed and with the proximal end portion of the assembly shown sectioned along a plane passing through the side ribs of the plunger.
Figure 47:
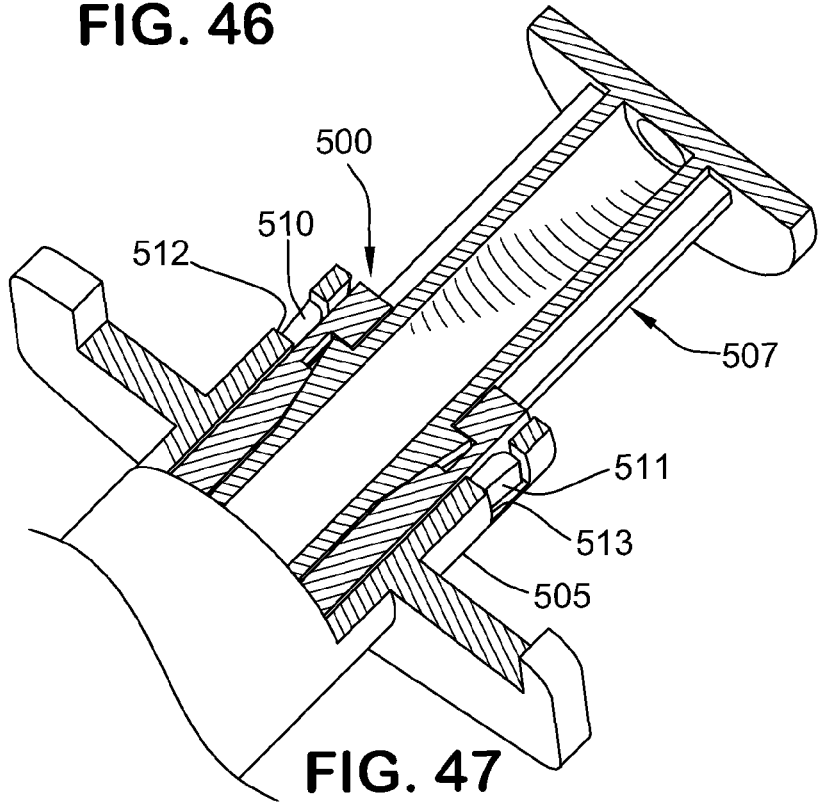
FIG. 47 is the same perspective view shown in FIG. 45 with the plunger installed.
Figure 48:
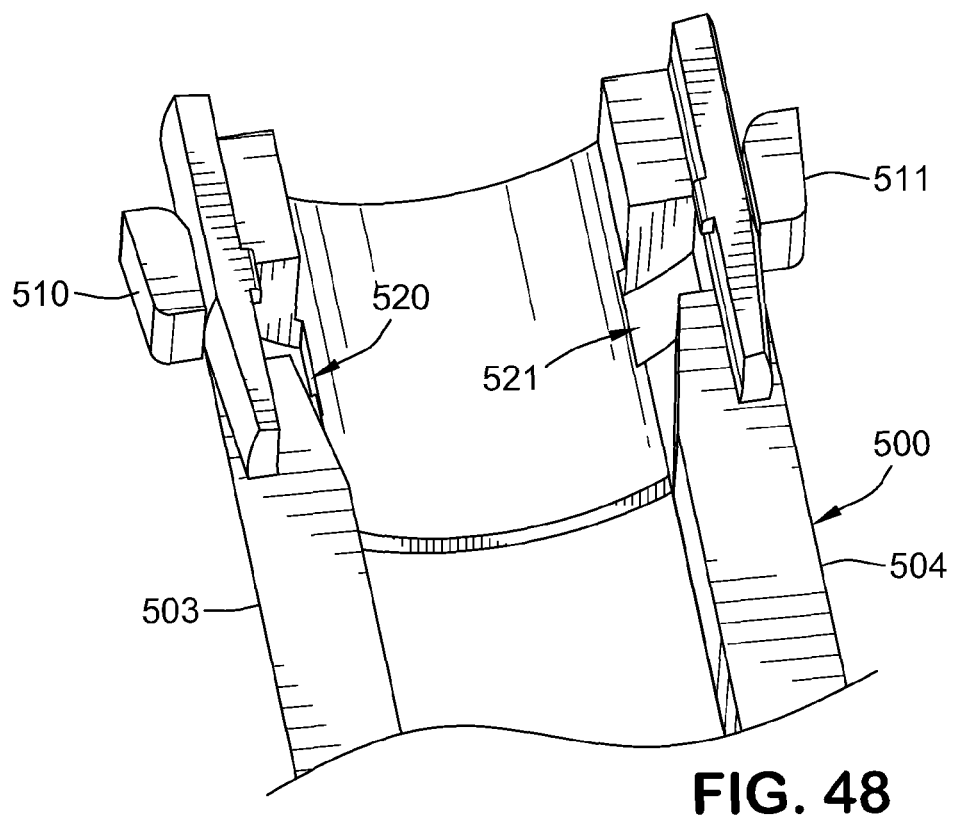
FIG. 48 is an enlarged perspective view of the proximal end portion of the spring retainer shown in FIG. 37.
Figure 49:
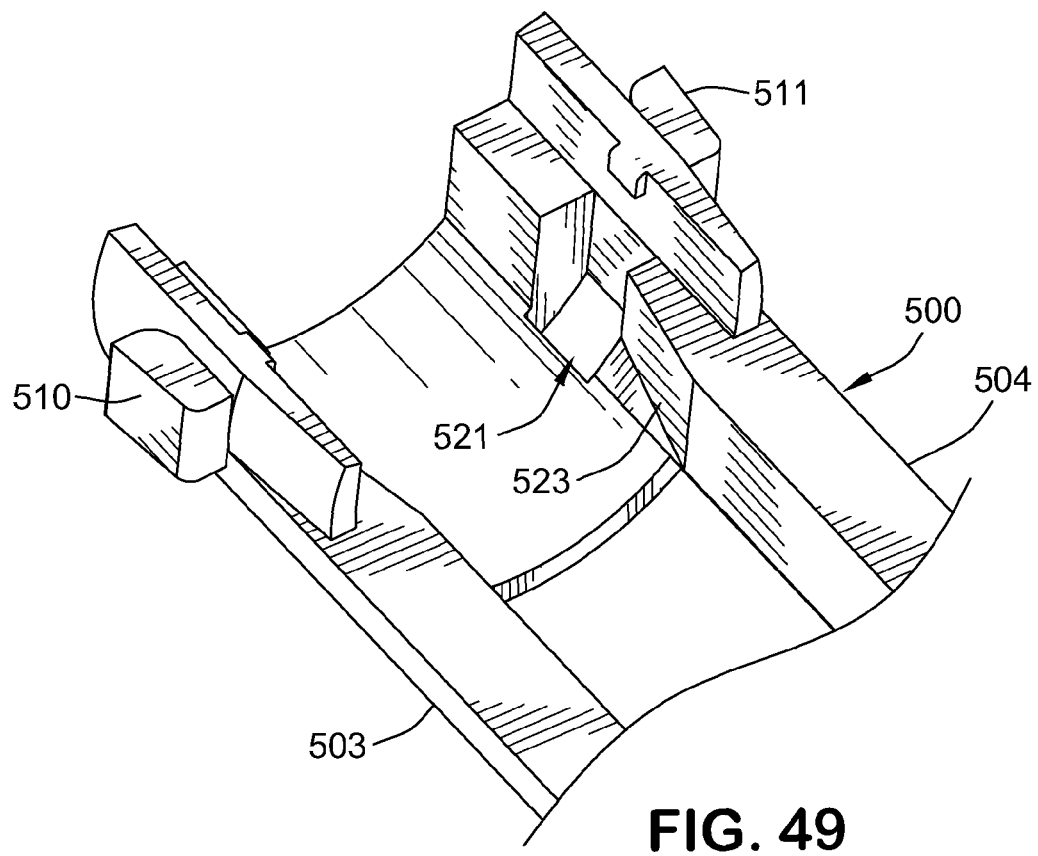
FIG. 49 is an enlarged perspective view of the same proximal end portion of the spring retain shown in FIG. 48, but from a different angle.

The proximal anchoring portion 501 of the safety control module 500 is installed in the barrel 505 with two generally triangular, diametral tabs or projections 510 and 511 (FIG. 40) fitting into a pair of complimentary, preferably square apertures 512 and 513 in the barrel 505, as shown in FIGS. 45-47. It does not require expansion of the barrel 505 or a step for support for the module 500, which has an outside diameter that is substantially the same as the inside diameter of the barrel 505. The internal surface 504a (FIG. 36) of the semi-circular anchoring portion 501, in combination with the plunger channel 546, form an axial retraction channel. The tabs 510 and 511 enter the barrel apertures 512 and 513 via inclined tracks 514 and 515 formed by the interior surface of the barrel 505 adjacent the apertures 512 and 513. Once engaged, the tabs 510 and 511 are restricted from exiting the apertures 512, 513 because of reverse angles 516 and 517 catching the barrel wall. Nor can the module 500 sink in the barrel 505 because the distal margins of the tabs 510 and 511 abut the lower margins of the apertures 512 and 513. The plunger flanges 508, 509 maintain diametric integrity of the barrel 505. The longitudinally extending ribs or flanges 508, 509 of the plunger 507 that form central channel 546 of the plunger 507, are secured between two solid support columns 512, 513, and retains the retraction elements in the central channel 506, described earlier. The back flange supports the free barrel 505 circumference.

Figure 50:
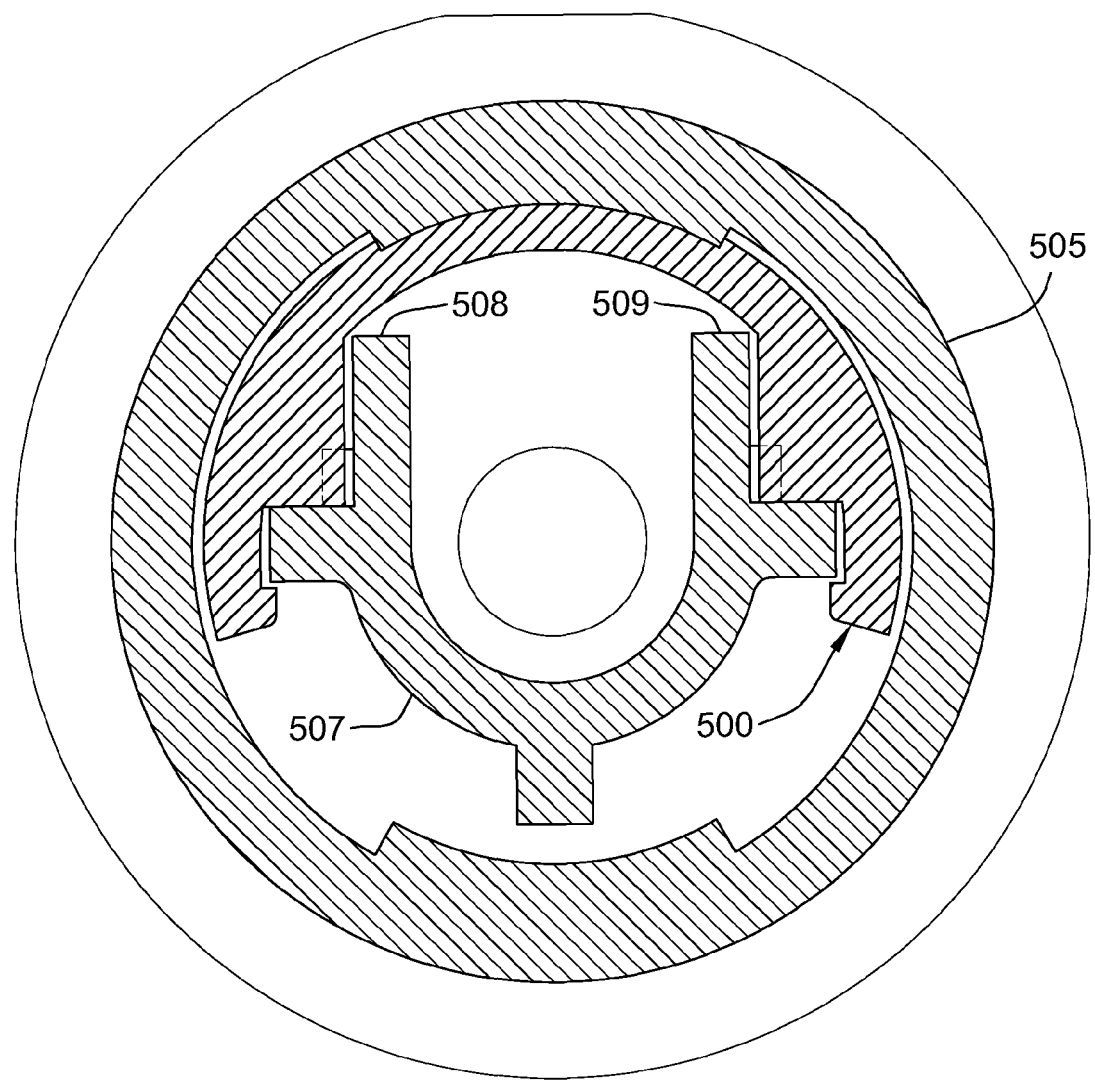
FIG. 50 is an enlarged section taken along line 50-50 in FIG. 36.

Once installed, the module 500 is securely engaged with the plunger 507 and cannot be removed from the barrel 505 without cutting the barrel wall. The solid bars 503 and 504 (FIG. 37) support both the front flanges 547, 548 and the side flanges 549, 551 of the plunger 11, as seen in FIG. 50. The bars 503 and 504 also form a pair of windows 520 and 521 with chamfered entries 522 and 523, respectively, for receiving the plunger side ramps 508b and 509b to lock the plunger 507 to the module 500 and thus to the barrel 505, to prevent movement of the plunger after the needle has been retracted.

Figure 33:
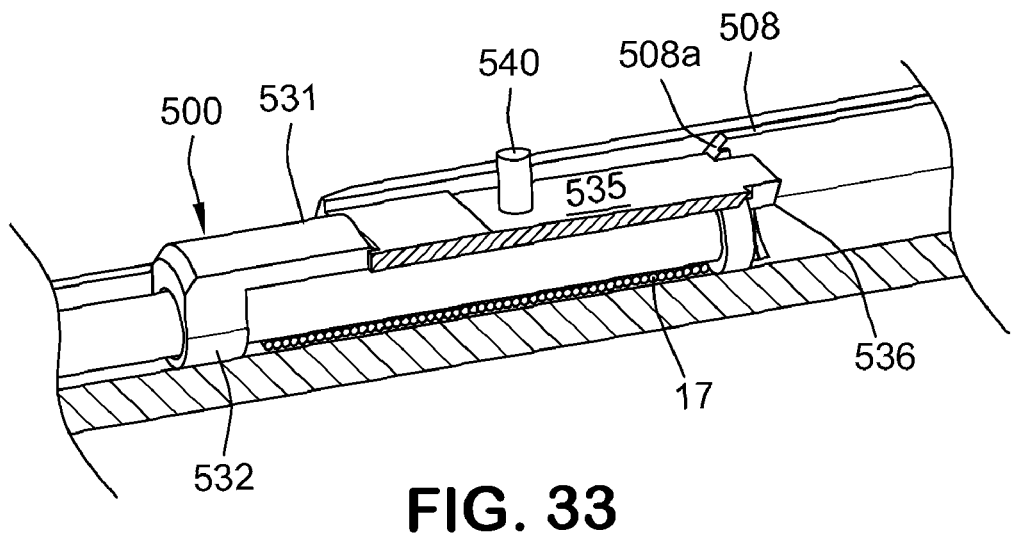
FIG. 33 is the same perspective view shown in FIG. 32b but with the plunger sectional along a vertical longitudinal plane through the axis of the plunger.
Figure 34:
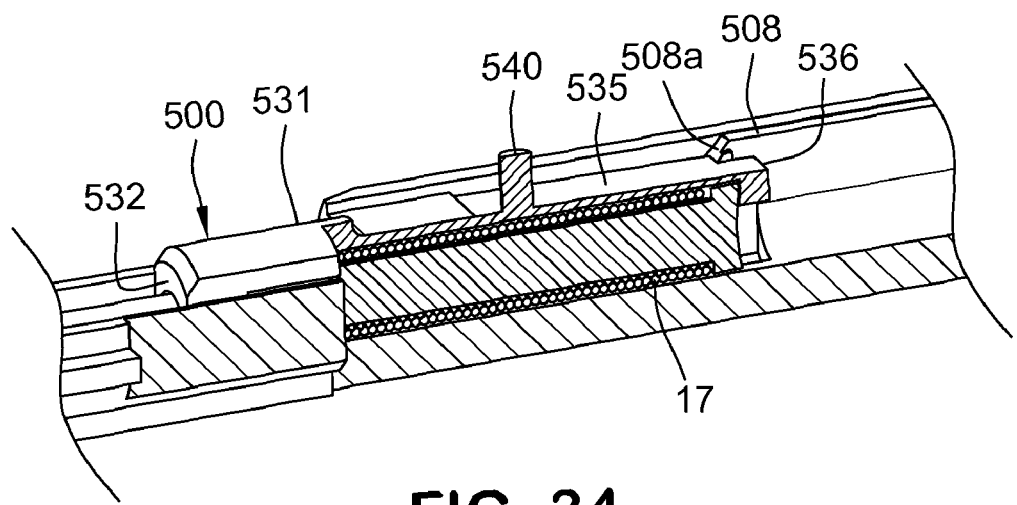
FIG. 34 is the same perspective view shown in FIG. 33 with the spring retainer, needle holder and spring sectional along line 33 in FIG. 32.
Figures 42, 43:
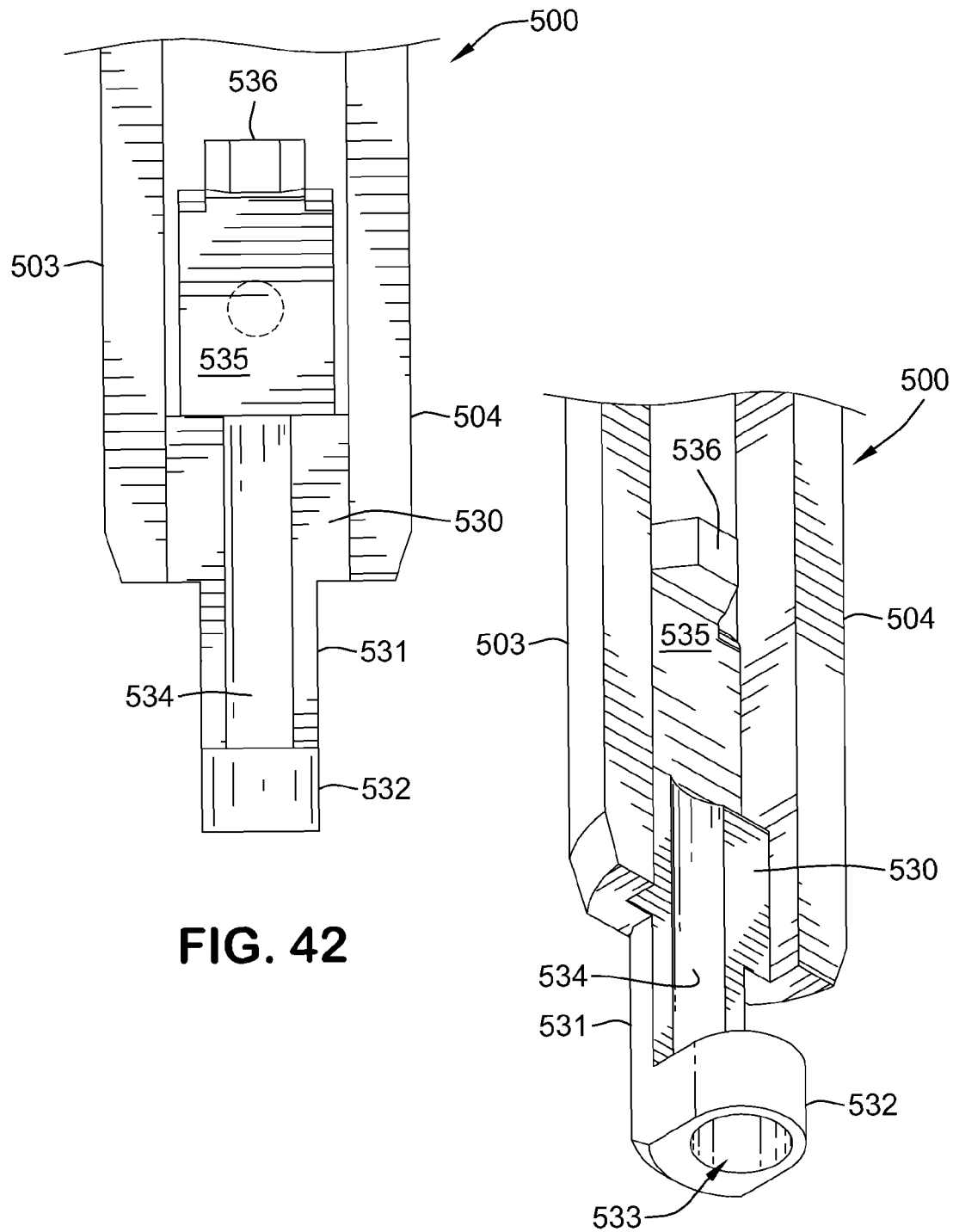
FIG. 42 is an enlarged top plane view of the spring retainer shown in FIG. 37 inserted in the distal end portion of a plunger.
FIG. 43 is a perspective view of the assembly shown in FIG. 42.
Figure 44:
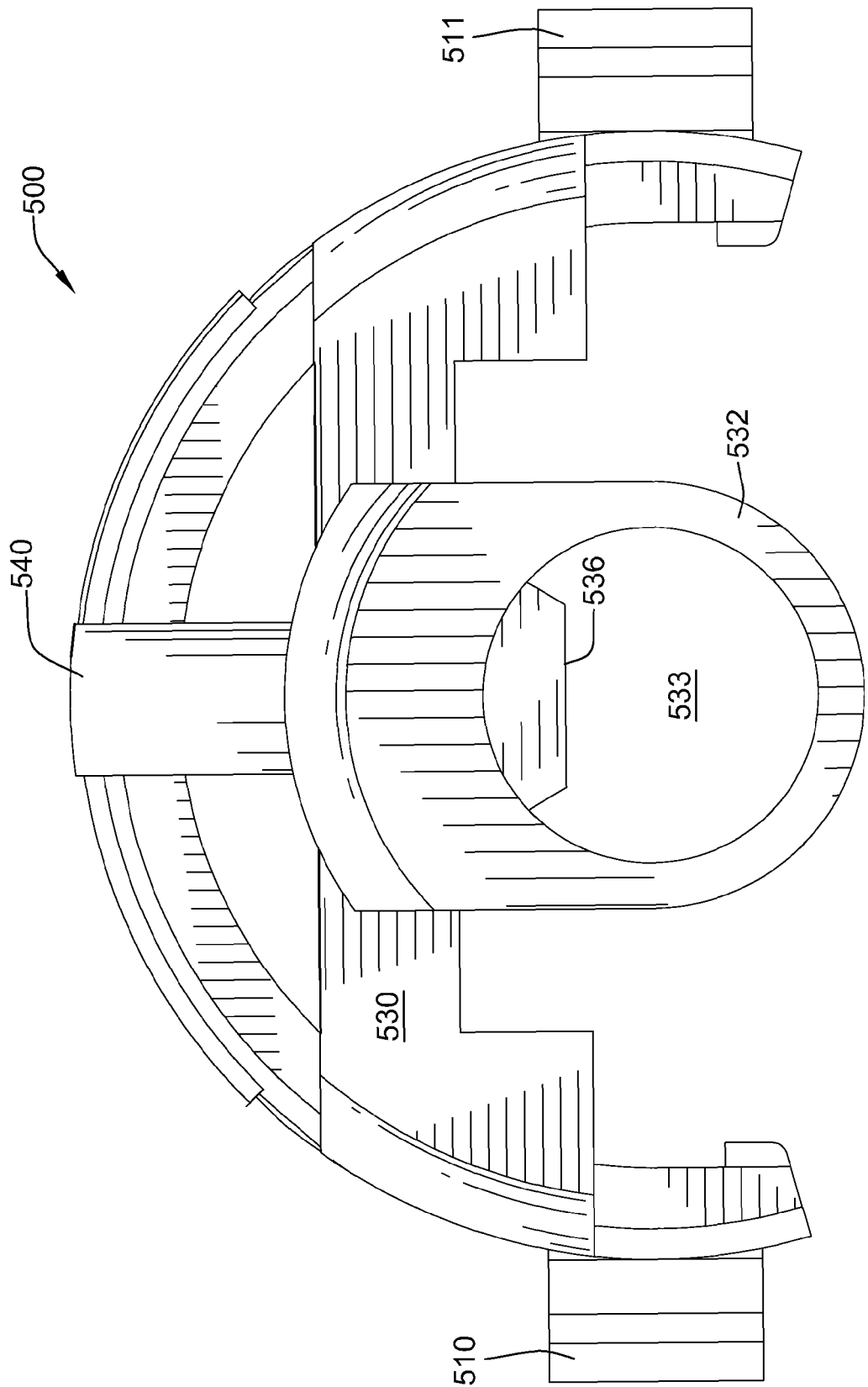
FIG. 44 is an enlarged end elevation of the distal end of the spring retainer shown in FIG. 37.

Referring once again to FIG. 37, the distal ends of the bars 503 and 504 are joined together by a support column 530 that forms a cantilevered distal spring support 531 (also referred to herein as "support bar") that terminates in a ring 532 protruding radially inward from the support 531. As seen in FIGS. 33-35, the ring 532 forms an opening 533 (FIG. 40) through which the needle holder (e.g., 14 of FIG. 1) is passed. The proximal side of the ring 532 receives and operatively supports the distal end of a retraction spring (e.g., 17 of FIG. 1). As seen in FIGS. 42-43, the interior surface of the spring support 531 forms a trough 534 to accommodate the size of the spring, and maintain the springs axial alignment. Proximally, the support column 530 forms a cantilevered proximal spring support 535 (also referred to herein as "pressure plate") with a central angular retaining projection 536 at its proximal end. The projection 536 presses on the needle holder head to keep the spring in a compressed state with the needle holder 14 advanced through the ring opening 533, and the needle advanced through the syringe nozzle 23, ready for injection.

The margin of the proximal spring support 535, on either side of the central projection 536, has two sloping surfaces 537 and 538 that are in direct and constant contact with the plunger ribs 508 and 509 as the plunger moves within the barrel 505 to draw and expel fluid during normal operation of the syringe. When injection is completed by the advancing movement of the plunger 507, the ramps 508a and 509a contact the sloping surfaces 537 and 538 on the margin of the projection 536. As the ramps 508a, 509a are advanced along the surfaces 537, 538, the cantilevered proximal spring support 535 is deflected radially outwardly so as to disengage the projection 536 from the proximal end of the needle holder, thereby releasing the needle holder and allowing the spring to expand longitudinally. This retracts the needle holder along with the attached needle. The locations of the ramps 508a, 509a are indexed to the location of the rubber stopper when it contacts front end of the barrel 505.

A post 540 is provided on the proximal spring support 535 to prevent the bending of the needle holder and assure the release of the projection 536 from the needle holder. The post 540 is located at the center of the support 535 and extends to the inner wall of the barrel, thereby keeping the needle holder 14 straight. Retraction of the needle is thus assured in all situations.

The distance between the spring support ring 532 and the projection 536 is generally equal to the solid length of the compression spring and the thickness of needle holder head. The reversible contact between the head of the needle holder and the projection 536 is strengthened by the angled contact surfaces. Release of the spring compression is effected by the advancing plunger when its triangular ramps radially displace the projection 536 of the safety control module to disengage the head of the needle holder.

Geometrically the length of the needle holder 14 is equal to the distance between the latching projection 536 of the spring retainer 500 and the nozzle of the barrel 505 where the needle projects out of the syringe. This is a mechanical distance and it is immaterial whether the spring is there or not. In an uncompressed, naturally expanded state, the spring 17 has urged the needle holder 14 in a retracted position toward the plunger end. For operative function the needle holder 14 and needle 13 must project out of the syringe nozzle. This position is achieved by fully compressing the spring 17 by the compression plate projection 536, pressing on the head of the needle holder 14.

Alternative Embodiments

Presented hereinbelow are an array of alternative embodiments and variations that fall within the scope and spirit of the present invention. The variants discussed hereinafter are not intended to represent every embodiment, or every aspect, of the present invention, and should therefore not be construed as limitations. Further, the following variants and embodiments may be used in any combination or sub-combination not otherwise logically prohibited.

In one embodiment of the present invention, a safety syringe assembly is presented. The syringe assembly comprises an elongated barrel with a nozzle at a distal end thereof. The barrel includes a cavity that extends longitudinally therein. In addition to the barrel, the syringe assembly also includes a plunger with a longitudinally elongated channel. The plunger is movably arranged at least partially in the barrel to transition between a fully retracted position and a fully advanced position.

The syringe assembly further comprises a needle holder with a needle attached at a distal end thereof. The needle holder is movably arranged at least partially within the plunger channel to move between a first (advanced) position, in which the needle projects at least partially from the distal end of the nozzle, and a second (retracted) position, in which the needle is fully enclosed within the barrel. A spring retainer is attached to the barrel. A compression spring is operatively supported by the spring retainer. The spring mates with and biases the needle holder toward the second, retracted position.

A first latch acts to latch the needle holder to the spring retainer to thereby maintain the spring in a compressed state. The first latch is repositionable in response to the plunger moving to the fully advanced position. When the first latch is repositioned, the needle holder is released from the spring retainer, allowing the compressed spring to expand and thereby move the needle holder to the second position. A second latch acts to latch the plunger to the barrel in response to movement of the plunger to the fully advanced position, thereby preventing movement of the plunger relative to the barrel after the plunger has moved to the fully advanced position.

According to one facet of this embodiment, the spring has a generally cylindrical shape. In this instance, the spring retainer engages at least a portion of the outer surface of the spring to maintain the generally cylindrical shape of the spring.

In accordance with another aspect, the spring retainer defines a longitudinally elongated passage. In this particular arrangement, the needle holder passes through and is slidably mounted within the spring retainer passage for movement between the first and second positions.

As part of another facet, the first latch includes a latching projection that is formed by the spring retainer. The latching projection engages the proximal end of the needle holder when the needle holder is in the first position. It may be desirable that the latching projection be normally biased inward toward a latched position, in which the projection overlaps a portion of the needle holder to thereby retain the needle holder in the first position. In this instance, the latching projection is deflectable outward to an unlatched position, in which the projection disengages the needle holder allowing the spring to expand and thereby move the needle holder to the second position. In addition, the plunger may include one or more ramp surfaces configured to engage with and deflect the latching projection outward to the unlatched position when the plunger moves to a predetermined advanced position within the barrel.

According to yet another facet, the barrel includes a first locking pocket that is shaped, sized and oriented to receive and lock with a complementary locking element formed by the spring retainer to thereby secure the spring retainer to the barrel.

As part of another aspect of this embodiment, the second latch includes a second locking pocket formed by the barrel. The second locking pocket is shaped, sized and oriented to receive and lock with one or more complementary locking projections that protrude from the plunger to thereby lock the plunger to the barrel when the plunger moves to a predetermined advanced position relative to the barrel.

In yet another facet, the spring is compressed between the needle holder and the spring retainer. In particular, the spring is captured by the needle holder at a proximal end of the spring, and by the spring retainer at a distal end of the spring.

According to even yet another aspect, the syringe further comprises a resilient cap that is attached to the distal end of the plunger, engaging an interior surface of the barrel. The resilient cap cooperates with the nozzle and barrel sidewalls to define an expandable fluid chamber therebetween.

As part of another alternative aspect, the syringe further comprises a needle cap that is designed to fit over the needle when the needle holder is in the first position. The needle cap is removeably attachable to the nozzle, and configured to trap fluids inside the barrel.

In yet another facet of this embodiment, the syringe may further comprise a manual switch that is actuable to release the first latch irrespective of plunger movement. In one exemplary configuration, the manual switch includes first and second elongated plates joined at respective proximal ends by an actuator plate. Distal ends of the elongated plates selectively engage and thereby release the first latch. The first and second elongated plates extend longitudinally within the barrel, between the plunger and the spring retainer.

In another embodiment of the present invention, a syringe assembly is provided. In this embodiment, the syringe assembly includes a hollow barrel with a nozzle at a distal end thereof. The barrel defines at least one pair of apertures. A plunger is slidably movable within the barrel. The plunger and the barrel cooperatively define a fluid chamber therebetween. The plunger has at least two integrally formed flanges that protrude laterally outward therefrom. A hollow needle is in fluid communication with the fluid chamber, and is retractably mounted with respect to the barrel.

The syringe assembly of this embodiment also includes a spring retainer having a retainer body with at least one pair of integrally formed projections. Each projection protrudes laterally outward from the retainer body into a respective one of the barrel apertures thereby locking the spring retainer to the barrel. The spring retainer body defines a longitudinally elongated passage for receiving and passing the plunger therethrough. The spring retainer and plunger cooperatively define a needle-retraction channel.

A needle retraction mechanism is operatively supported by the spring retainer, passing through the needle-retraction channel. The needle retraction mechanism includes a needle holder attached at a distal end thereof to the needle. A spring circumscribes a portion of the needle holder, biasing the needle holder from an advanced position, in which the needle projects out of the barrel from the nozzle, and a retracted position, in which the needle and needle holder are fully enclosed within the barrel.

During normal operation of the syringe, the spring retainer grips the needle holder thereby retaining the spring in a compressed state between the needle holder and the spring retainer. However, when the plunger slides to the fully advanced position, the spring retainer releases the needle holder, whereby the spring is allowed to expand and thereby move the needle holder to the retracted position. In addition, the spring retainer defines at least two windows. Each window is shaped, sized, and orientated to receive a respective one of the plunger flanges when the plunger reaches the fully advanced position, whereby the plunger is locked to the spring retainer, preventing movement of the plunger relative to the barrel after the needle has been retracted within the barrel.

According to one aspect of this embodiment, the retainer body has a substantially semi-cylindrical anchoring portion at a proximal end thereof. The anchoring portion has an outer-diameter surface with a diameter that is substantially equal to the diameter of an inner-diameter surface of the barrel. The anchoring portion may also be fabricated such that an inner peripheral surface thereof is configured to contact and thereby stabilize the plunger during movement of the plunger through the longitudinally elongated passage. To this regard, the plunger flanges are preferably designed to engage the inner peripheral surface of the spring retainer body anchoring portion.

In another aspect of this embodiment, the spring retainer body has an integrally formed support bar at a distal end thereof. The support bar includes an integral ring which receives therethrough at least a portion of the needle retraction mechanism, thereby providing support for the needle retraction mechanism. The support bar is preferably connected to the anchoring plate by first and second elongated columns. The support bar may also be designed with a longitudinally elongated trough that is configured to accommodate the spring and maintain longitudinal alignment of the spring.

In another facet, the spring retainer body has a central pressure plate with a projection extending inwardly therefrom. The projection engages a proximal end of the needle holder to thereby hold the spring in a compressed state. In one particular arrangement, the sides of the pressure plate are in constant contact with the plunger flanges while the plunger moves toward the fully advanced position, and wherein the plunger flanges deflect the pressure plate radially outward when the plunger reaches the fully advanced position. In this instance, the plunger flanges are preferably in constant contact with the semicircular anchoring portion.

In accordance with yet another embodiment, an automatically-retractable hypodermic syringe assembly is provided. The syringe assembly includes a generally-cylindrical, hollow barrel with a nozzle at a distal end thereof. The barrel includes an elastomeric O-ring that is mounted within the nozzle. An elongated needle holder, which has a hollow needle attached at a distal end thereof, is disposed within the barrel. A spring presses against and biases the needle holder and needle into a retracted position.

The syringe assembly also includes a spring retainer with a semicircular anchoring plate at a proximal end thereof. The spring retainer also defines a pair of apertures at the proximal end thereof. In addition, the spring retainer is also formed with a compression plate at a distal end thereof. The compression plate is fabricated with a retaining projection that is designed to engage and temporarily restrain the needle holder. Restraining the needle holder acts to compress the spring, which in turn forces the needle to protrude out of the barrel nozzle.

In addition to the above indicated structure, the syringe assembly of this embodiment further comprises an elongated plunger with two longitudinally extending, parallel ribs that cooperatively define a central cavity therebetween. Each rib has a ramp that is indexed to selectively contact the spring retainer compression plate. Each rib further includes a triangular projection jutting from a proximal portion of the rib. The triangular projections are positioned to selectively engage with a respective one of the spring retainer apertures.

In accordance with this embodiment, moving the plunger towards the barrel nozzle to a predetermined advanced position within the barrel acts to: (1) engage the plunger ramps with the compression plate thereby deflecting the retaining projection outward and releasing the needle holder such that the spring expands and forces the needle to a retracted position entirely within the barrel; and (2) engage each of the plunger projections with a respective one of the spring retainer apertures and thereby interlock the plunger with the spring retainer and disable the syringe.

According to one facet of this embodiment, the syringe assembly further comprises a hollow catheter with a female luer end that is operatively attached to the needle and the barrel nozzle. Ideally, the hollow catheter exhibits flashback confirmation while puncturing veins. In addition, retraction of the needle leaves the hollow catheter in the vein to provide venous access. A similarly designed catheter is presented in commonly owned U.S. Pat. No. 7,481,797 B2, entitled "Retractable Needle Single Use Safety Syringe," which issued on Jan. 27, 2009, to Dr. Sakharam D. Mahurkar, and is incorporated herein by reference in its entirety.

In accordance with another facet, interlocking the plunger with the spring retainer renders the plunger and cap non-removable from the barrel without otherwise breaking the syringe assembly, such as rupturing the barrel. To this regard, interlocking the plunger with the spring retainer preferably renders the syringe assembly spill-proof.

As part of another aspect of this embodiment, the syringe assembly further comprises a needle blocking shield installed over the needle. The blocking shield is configured to retain fluid within the barrel to maintain a pre-filled syringe until the blocking shield is removed. It may also be desirable that the blocking shield be configured to form an air-tight seal with the barrel preventing accidental retraction of the needle by preventing inadvertent advancement of the plunger to the predetermined advanced position. The syringe may be pre-filled with a medicine or other fluid by inserting through the open proximal end of the barrel a filling tube that extends along the full length of the plunger, between the plunger and the barrel, with the distal end portion of the tube extending between the outer surface of the resilient cap and the inside surface of the barrel, into the space between the distal end of the cap and the sealing O-ring. The filling tube is used to pre-fill the syringe with the desired amount of the selected fluid, and then is withdrawn from the syringe.

While the best modes for carrying out the present invention have been described in detail, those familiar with the art to which this invention relates will recognize various alternative designs and embodiments for practicing the invention within the scope of the appended claims.

The invention claimed is:

1. A syringe assembly, comprising:
   an elongated barrel with a nozzle at a distal end thereof, said barrel defining a longitudinally elongated cavity therein;
   a resilient O-ring mounted within said nozzle;
   a plunger defining a longitudinally elongated channel and having a resilient cap on the distal end of the plunger, wherein said plunger is movably arranged at least partially in said barrel to transition between a fully retracted position and a fully advanced position;
   a needle;
   a longitudinally elongated needle holder attached at a distal end thereof to said needle and extending from said needle through said resilient cap and into said elongated channel, wherein said needle holder is movably arranged at least partially in said channel of said plunger to move between a first position, in which said needle projects at least partially from said distal end of said nozzle, and a second position, in which said needle is fully enclosed within said barrel;
   a spring retainer operatively attached to said barrel and spaced proximally from said resilient cap;
   a spring operatively supported by said spring retainer, wherein said spring mates with and biases said needle holder toward said second position;
   a first latch latching said needle holder to said spring retainer to thereby maintain said spring in a compressed state, wherein said first latch is repositionable in response to contact with said plunger when said plunger is moved to said fully advanced position independently of said spring so that said plunger repositions said first latch without compressing said spring, whereby said needle holder is released from said spring retainer allowing said compressed spring to expand and thereby move said needle holder to said second position; and
   a second latch latching said plunger to said barrel in response to movement of said plunger to said fully advanced position thereby preventing movement of said plunger relative to said barrel after said plunger has moved to said fully advanced position.

2. The syringe of claim 1, wherein said spring has a generally cylindrical shape, and wherein said spring retainer engages at least a portion of the outer surface of said spring to maintain the generally cylindrical shape of said spring.

3. The syringe of claim 1, wherein said spring retainer defines a longitudinally elongated passage, and wherein said needle holder is slidably mounted within said passage for movement between said first and second positions.

4. The syringe of claim 1, wherein said first latch includes a latching projection formed by said spring retainer, said latching projection engaging the proximal end of said needle holder when said needle holder is in said first position.

5. The syringe of claim 4, wherein said latching projection is biased inward toward a latched position, in which said projection overlaps a portion of said needle holder to thereby retain said needle holder in said first position, and wherein said latching projection is deflectable outward to an unlatched position, in which said projection disengages said needle holder allowing said spring to expand and thereby move said needle holder to said second position.

6. The syringe of claim 5, wherein said plunger includes at least one ramp surface configured to engage with and deflect said latching projection outward to said unlatched position when said plunger moves to a predetermined advanced position within said barrel.

7. The syringe of claim 1, wherein said barrel includes
a first locking pocket configured to receive and lock with a complementary locking element formed by said spring retainer to thereby secure said spring retainer to said barrel.

8. A syringe assembly, comprising:
an elongated barrel with a nozzle at a distal end thereof, said barrel defining a longitudinally elongated cavity therein;
a resilient O-ring mounted within said nozzle;
a plunger defining a longitudinally elongated channel, wherein said plunger is movably arranged at least partially in said barrel to transition between a fully retracted position and a fully advanced position;
a needle;
a needle holder attached at a distal end thereof to said needle, wherein said needle holder is movably arranged at least partially in said channel of said plunger to move between a first position, in which said needle projects at least partially from said distal end of said nozzle, and a second position, in which said needle is fully enclosed within said barrel;
a spring retainer operatively attached to said barrel;
a spring operatively supported by said spring retainer, wherein said spring mates with and biases said needle holder toward said second position;
a first latch latching said needle holder to said spring retainer to thereby maintain said spring in a compressed state, wherein said first latch is repositionable in response to movement of said plunger to said fully advanced position, whereby said needle holder is released from said spring retainer allowing said compressed spring to expand and thereby move said needle holder to said second position;
a second latch latching said plunger to said barrel in response to movement of said plunger to said fully advanced position thereby preventing movement of said plunger relative to said barrel after said plunger has moved to said fully advanced position; and a first locking pocket configured to receive and lock with a complementary locking element formed by said spring retainer to thereby secure said spring retainer to said barrel,
wherein said second latch includes a second locking pocket formed by said spring-retainer with said barrel, wherein said second locking pocket is configured to receive and lock with at least one complementary locking projection protruding from said plunger to thereby lock said plunger to said spring retainer and said barrel when said plunger moves to a predetermined advanced position.

9. The syringe of claim 1, wherein said second latch includes a second locking pocket formed by said barrel, wherein said second locking pocket is configured to receive and lock with at least one complementary locking projection protruding from said plunger to thereby lock said plunger to said barrel when said plunger moves to a predetermined advanced position.

10. The syringe of claim 1, wherein said spring is compressed between said needle holder and said spring retainer, captured by said needle holder at a proximal end of said spring and by said spring retainer at a distal end of said spring.

11. The syringe of claim 1, wherein said resilient cap cooperates with said nozzle and said barrel to define an expandable fluid chamber therebetween.

12. The syringe of claim 11, wherein said syringe is pre-filled with medicine through the proximal end of said barrel, and further comprising a needle cap configured to fit over said nozzle and reversibly block said needle when said needle holder is in said first position, and wherein said needle cap is removable from the said nozzle when the pre-filled medicine is to be administered to a patient.

13. A syringe assembly, comprising:
an elongated barrel with a nozzle at a distal end thereof, said barrel defining a longitudinally elongated cavity therein;
a resilient O-ring mounted within said nozzle;
a plunger defining a longitudinally elongated channel, wherein said plunger is movably arranged at least partially in said barrel to transition between a fully retracted position and a fully advanced position;
a needle;
a needle holder attached at a distal end thereof to said needle, wherein said needle holder is movably arranged at least partially in said channel of said plunger to move between a first position, in which said needle projects at least partially from said distal end of said nozzle, and a second position, in which said needle is fully enclosed within said barrel;
a spring retainer operatively attached to said barrel;
a spring operatively supported by said spring retainer, wherein said spring mates with and biases said needle holder toward said second position;
a first latch latching said needle holder to said spring retainer to thereby maintain said spring in a compressed state, wherein said first latch is repositionable in response to contact with said plunger when said plunger is moved to said fully advanced position independently of said spring so that said plunger repositions said first latch without compressing said spring, whereby said needle holder is released from said spring retainer allowing said compressed spring to expand and thereby move said needle holder to said second position;
a second latch latching said plunger to said barrel in response to movement of said plunger to said fully advanced position thereby preventing movement of said plunger relative to said barrel after said plunger has moved to said fully advanced position; and a manual switch configured to release said first latch upon actuation of said switch by an operator of the syringe irrespective of said plunger movement.

14. A syringe assembly, comprising:

an elongated barrel with a nozzle at a distal end thereof, said barrel defining a longitudinally elongated cavity therein;

a resilient O-ring mounted within said nozzle;

a plunger defining a longitudinally elongated channel, wherein said plunger is movably arranged at least partially in said barrel to transition between a fully retracted position and a fully advanced position;

a needle;

a needle holder attached at a distal end thereof to said needle, wherein said needle holder is movably arranged at least partially in said channel of said plunger to move between a first position, in which said needle projects at least partially from said distal end of said nozzle, and a second position, in which said needle is fully enclosed within said barrel;

a spring retainer operatively attached to said barrel;

a spring operatively supported by said spring retainer, wherein said spring mates with and biases said needle holder toward said second position;

a first latch latching said needle holder to said spring retainer to thereby maintain said spring in a compressed state, wherein said first latch is repositionable in response to movement of said plunger to said fully advanced position, whereby said needle holder is released from said spring retainer allowing said compressed spring to expand and thereby move said needle holder to said second position;

a second latch latching said plunger to said barrel in response to movement of said plunger to said fully advanced position thereby preventing movement of said plunger relative to said barrel after said plunger has moved to said fully advanced position; and a manual switch configured to release said first latch upon actuation of said switch by an operator of the syringe irrespective of said plunger movement, wherein said manual switch includes first and second elongated plates joined at respective proximal ends by an actuator plate, wherein distal ends of said elongated plates selectively engage and thereby release said first latch.

15. The syringe of claim 14, wherein said first and second elongated plates extend longitudinally within said barrel between said plunger and said spring retainer.

16. A safety syringe assembly, comprising:

an elongated, generally-cylindrical barrel defining a longitudinally elongated cavity therein, said barrel forming a hollow nozzle at a distal end of said barrel, said nozzle opening into said cavity of said barrel;

a plunger defining a longitudinally elongated open channel and slidably mounted at least partially in said barrel cavity and configured to draw fluid into said barrel cavity when retracted in a first direction toward a fully retracted position, and to expel fluid from said barrel when advanced in a second direction toward a fully advanced position;

a resilient O-ring mounted within said nozzle;

a resilient cap attached to the distal end of said plunger and engaging an interior surface of said barrel;

a hollow needle;

a needle holder mounted at a distal end thereof to said needle, wherein said needle holder is slidably mounted inside said plunger channel and inside said barrel cavity for movement between an advanced position, in which said needle on the distal end of said needle holder projects out of said barrel from a distal end of said nozzle, and a retracted position, in which said needle and said needle holder are fully enclosed within said barrel;

a spring retainer positioned within said barrel cavity and locked to said barrel;

a compression spring positioned within said spring retainer and circumscribing said needle holder, wherein said spring urges said needle holder toward said retracted position;

a first latch latching said needle holder to said spring retainer to temporarily maintain said spring in a compressed state, wherein said first latch is releasable in response to contact with said plunger when said plunger is moved to said fully advanced position independently of said spring so that said plunger repositions said first latch without compressing said spring, whereby said needle holder is released from said spring retainer allowing said spring to expand and thereby move said needle holder to said retracted position; and a second latch latching said plunger to said barrel in response to said plunger sliding to said fully advanced position thereby preventing movement of said plunger relative to said barrel after said needle has been retracted within said barrel.

17. A syringe assembly, comprising:

a hollow barrel with a nozzle at a distal end of said barrel, said barrel defining at least one pair of apertures;

a plunger slidably movable within said barrel, said cap and said barrel at least partially defining a fluid chamber therebetween, wherein said plunger has at least two flanges protruding laterally outward therefrom;

a resilient cap attached to the distal end of said plunger and engaging an interior surface of said barrel;

a hollow needle in fluid communication with said fluid chamber and retractably mounted with respect to said barrel;

a spring retainer having a retainer body with at least one pair of projections each protruding laterally outward from said body into a respective one of said at least one pair of apertures thereby locking said spring retainer to said barrel, said spring retainer body defining a longitudinally elongated passage for receiving said plunger therethrough, said spring retainer and said plunger cooperatively defining a needle-retraction channel;

a needle retraction mechanism passing through said needle-retraction channel and operatively supported by said spring retainer, said needle retraction mechanism including a needle holder attached at a distal end thereof to said needle, and a spring circumscribing a portion of said needle holder and biasing said needle holder from an advanced position, in which said needle projects out of said barrel nozzle, to a retracted position, in which said needle and said needle holder are fully enclosed within said barrel;

wherein said spring retainer grips said needle holder thereby retaining said spring in a compressed state between said needle holder and said spring retainer, and releases said needle holder in response to said plunger sliding to a fully advanced position, whereby said spring is allowed to expand and thereby move said needle holder to said retracted position; and wherein said spring retainer defines at least two windows each configured to receive a projection respective one of said of at least two plunger flanges when said plunger reaches said fully advanced position, whereby said plunger is locked to said spring retainer.

18. The syringe assembly of claim 17, wherein said retainer body has a substantially semi-cylindrical anchoring portion at a proximal end thereof, said anchoring portion having an outer surface with a first diameter and said barrel having an inner surface with a second diameter substantially equal to said first diameter.

19. The syringe assembly of claim 18, wherein said anchoring portion has an inner peripheral surface configured to contact and thereby stabilize said plunger during movement of said plunger through said longitudinally elongated passage.

20. The syringe assembly of claim 19, wherein said at least two plunger flanges are configured to engage said inner peripheral surface of said anchoring portion.

21. The syringe assembly of claim 17, wherein said spring retainer body has a support bar at a distal end thereof, said support bar including a ring receiving therethrough and supporting at least a portion of said needle retraction mechanism.

22. The syringe assembly of claim 21, wherein said support bar is connected to said anchoring plate by first and second elongated columns.

23. The syringe assembly of claim 22, wherein said support bar defines a longitudinally elongated trough configured to mate with and maintain longitudinal alignment of said spring.

24. The syringe assembly of claim 17, wherein said spring retainer body has a central pressure plate with a projection extending inwardly therefrom and engaging a proximal end of said needle holder to thereby hold said spring in a compressed state.

25. The syringe assembly of claim 24, wherein the sides of said pressure plate are in constant contact with said plunger flanges when said plunger moves toward said fully advanced position, and wherein said plunger flanges deflect said pressure plate radially outward when said plunger reaches said fully advanced position.

26. The syringe assembly of claim 25, wherein said plunger flanges are in constant contact with said anchoring portion.

27. A retractable safety syringe, comprising:
a hollow barrel with locking means at a proximal end of said barrel and a hollow nozzle with an internally mounted o-ring at a distal end of said barrel;
a plunger with interlocking means at a proximal end thereof and a resilient sealing cap mounted at a distal end thereof, said plunger having two longitudinally extending parallel ribs that define a central retraction channel therebetween, each of said parallel ribs having an angled ramp on the edge of the rib;
a tubular retraction control module located inside said barrel and anchored at a proximal end thereof to said barrel by said locking means, said control module having a ring at a distal end thereof, said ring receiving therein and supporting a spring encircling a needle holder, said control module including a compression plate configured to selectively retain said needle holder to thereby compress said spring between said needle holder and said control module, wherein said spring is configured to bias said needle holder and a needle attached thereto into a retracted position within said barrel; and
wherein said plunger is selectively advanced longitudinally within said barrel from a fully retracted position, in which said cap is distal from said nozzle, to a fully advanced position, in which said cap is proximate to said nozzle, whereby fluid is expelled from said barrel, said plunger is locked to said control module via said interlocking means, and said compression plate is displaced radially outward via said angled ramps thereby releasing said needle holder and said spring and permitting expansion of said spring whereby said needle is retracted into said barrel.

28. An automatically-retractable hypodermic syringe assembly, comprising:
a generally-cylindrical hollow barrel with a nozzle at a distal end thereof, said barrel including an elastomeric O-ring mounted within said nozzle;
an elongated needle holder with a hollow needle attached at a distal end thereof;
a spring pressing against and biasing said needle holder toward a retracted position;
a spring retainer with a semicircular anchoring plate at a proximal end thereof, and a compression plate at a distal end of said spring retainer, said compression plate having a retaining projection configured to engage said needle holder and thereby compress said spring and force said needle to protrude out of said barrel nozzle, said spring retainer defining a pair of apertures at said proximal end;
an elongated plunger with two longitudinally extending parallel ribs defining a central cavity therebetween, each of said ribs having a ramp indexed to selectively contact said spring retainer compression plate, and a triangular projection jutting from a proximal portion of said rib, wherein each of said triangular projections is positioned to selectively engage with a respective one of said spring retainer apertures;
wherein moving said plunger towards said barrel nozzle to a predetermined advanced position within said barrel acts to:
engage said plunger ramps with said compression plate thereby deflecting said retaining projection outward and releasing said needle holder such that said spring expands and forces said needle to a retracted position entirely within said barrel; and
engage each of said plunger projections with a respective one of said spring retainer apertures and thereby interlock said plunger with said spring retainer and disable the syringe.

29. The syringe assembly of claim 28, further comprising a hollow catheter with a female luer end operatively attached onto said needle and said barrel nozzle, wherein said hollow catheter exhibits flashback confirmation in said barrel while puncturing veins, and whereby retraction of said needle leaves said hollow catheter in the vein to provide venous access.

30. The syringe assembly of claim 28, wherein engagement of said plunger with said spring retainer renders the syringe assembly spill-proof.

31. The syringe assembly of claim 28, further comprising a needle blocking shield installed on said nozzle to retain medicine pre-filled in said barrel through the proximal end of said barrel by a tube extending past said resilient cap, until injected in patient, by removing the said blocking shield.

32. The syringe assembly of claim 28, which includes a needle shield installed on said nozzle and forming an air-tight seal so that the air retained in said barrel prevents accidental and inadvertent retraction of said needle by preventing advancement of said plunger to said predetermined advanced position.

33. An auto-retracting safety syringe, comprising:
an elongated hollow barrel having a nozzle at a distal end thereof;
a plunger inserted through an opening in a proximal end of said barrel spaced from said plunger distal end, said plunger having an elongated body with a pair of parallel ribs cooperatively defining a retraction cavity, and a pair of triangular detents each protruding from an outer surface of a respective one of said ribs;

a resilient cap fixed to a distal end of said plunger;

an elongated needle holder with a hollow needle attached at a distal end thereof movably mounted within said barrel and at least partially within said retraction cavity;

a spring pressing against and biasing said needle holder into a retracted position;

a spring retainer fixed at a proximal end thereof to said proximal end of said barrel, said spring retainer temporarily retaining said spring in a compressed state such that said needle protrudes at least partially from said barrel nozzle, said spring retainer defining a plurality of cavities each configured to selectively receive a respective on of said plunger detents;

wherein pressing said plunger towards said nozzle acts to slide each of said triangular detents into a respective one of said spring retainer cavities once said plunger reaches a fully advanced position with respect to said nozzle.

34. A syringe, comprising a barrel with locking means at a proximal end and a nozzle with an o-ring at a distal end;

a needle holder with a hollow needle attached at a distal end and a head at a proximal end;

a spring encircling said needle holder, said spring pressing against and biasing said needle holder into a retracted position;

a plunger with interlocking means at a proximal end locking said plunger to said barrel, a resilient sealing cap fixed at a distal end, and a central retraction channel defined by two parallel ribs each carrying an angular projection on a margin in mid-portion and in proximity of said needle holder head when said plunger is fully advanced within said barrel, each of said ribs further including at least one projection protruding laterally outward from the plunger; and an elongated retraction control, anti-reuse module extending within said retraction channel, said module including a generally semicircular plate at a proximal end, said plate configured to mate with and stabilize said plunger ribs, said plate defining two windows configured to selectively receive and engage with said plunger projections and thereby anchor said plunger to said module, said module forming a support with a vertical compression plate having a radial projection pressing on said head of said needle holder to compress said spring supported on a margin of a ring at the end of the said module;

wherein said needle holder is retained via said module in a normal-use orientation whereat said needle protrudes at least partially from said barrel nozzle;

wherein advancing said plunger in said barrel toward said nozzle radially displaces said compression plate by said projections on said parallel ribs, releasing pressure on said needle holder head and compressed spring such that said spring instantaneously expands and retracts said needle and needle holder into said barrel; and wherein advancing said plunger in said barrel toward said nozzle obligates entry of said plunger into said module by rib compression, locking said projections in said apertures of said module thereby preventing re-use of the syringe.

* * * * *